(12) United States Patent
Beckham et al.

(10) Patent No.: US 10,017,792 B2
(45) Date of Patent: Jul. 10, 2018

(54) BIOMASS CONVERSION TO FUELS AND CHEMICALS

(71) Applicant: Alliance for Sustainable Energy, LLC, Golden, CO (US)

(72) Inventors: Gregg T. Beckham, Denver, CO (US); Christopher W. Johnson, Denver, CO (US); Derek R. Vardon, Lakewood, CO (US); Mary Ann Franden, Centennial, CO (US)

(73) Assignee: Alliance for Sustainable Energy, LLC, Golden, CO (US)

( * ) Notice: Subject to any disclaimer, the term of this patent is extended or adjusted under 35 U.S.C. 154(b) by 0 days.

(21) Appl. No.: 14/804,161

(22) Filed: Jul. 20, 2015

(65) Prior Publication Data
US 2016/0017381 A1    Jan. 21, 2016

Related U.S. Application Data

(60) Provisional application No. 62/062,224, filed on Oct. 10, 2014, provisional application No. 62/026,222, filed on Jul. 18, 2014.

(51) Int. Cl.
*C12P 7/44* (2006.01)
*C07C 51/47* (2006.01)
*C07C 51/43* (2006.01)
*C07C 51/36* (2006.01)
*C12N 9/88* (2006.01)

(52) U.S. Cl.
CPC ............... *C12P 7/44* (2013.01); *C07C 51/36* (2013.01); *C07C 51/43* (2013.01); *C07C 51/47* (2013.01); *C12N 9/88* (2013.01); *C12Y 113/11001* (2013.01); *C12Y 401/01063* (2013.01); *C12Y 402/01118* (2013.01)

(58) Field of Classification Search
None
See application file for complete search history.

(56) References Cited

U.S. PATENT DOCUMENTS

| | | |
|---|---|---|
| 1,594,389 A | 8/1926 | Thellier |
| 1,888,025 A | 11/1932 | Bent |
| 2,037,001 A | 4/1936 | Aronovsky |
| 2,042,705 A | 6/1936 | Dreyfus |
| 3,888,727 A | 6/1975 | Kenig |
| 3,932,207 A | 1/1976 | Fogarassy |
| 4,259,444 A | 3/1981 | Chakrabarty |
| 4,480,034 A | 10/1984 | Hsieh |
| 4,520,105 A | 5/1985 | Sinner et al. |
| 4,594,130 A | 6/1986 | Chang et al. |
| 4,731,328 A | 3/1988 | Maxwell |
| 5,487,987 A | 1/1996 | Frost et al. |
| 5,730,837 A | 3/1998 | Black et al. |
| 8,133,704 B2 | 3/2012 | Baynes et al. |
| 8,211,683 B2 * | 7/2012 | Mase ............... C12N 9/0008 435/183 |
| 9,206,445 B2 | 12/2015 | Yang et al. |
| 2014/0107381 A1 | 4/2014 | Beckham et al. |
| 2014/0186902 A1 | 7/2014 | Botes et al. |
| 2014/0193868 A1 | 7/2014 | Sabirova et al. |
| 2014/0273104 A1 | 9/2014 | Paripati et al. |
| 2014/0302573 A1 | 10/2014 | Burk et al. |
| 2016/0052949 A1 | 2/2016 | Beckham et al. |

FOREIGN PATENT DOCUMENTS

| | | |
|---|---|---|
| WO | WO 2011/017560 A1 | 2/2011 |
| WO | WO 2012/106257 A1 | 8/2012 |

OTHER PUBLICATIONS

Daniel R et al. Biochemistry of coenzyme B12-dependent glycerol and diol dehydratases and organization of the encoding genes. 1999. FEMS Microbiology Reviews. 22:553-566.*

Kelada SN et al. Gamma-aminolevulinic acid dehydratase genotype and lead toxicity: A huge review. 2001. American Journal of Epidemiology. vol. 154, No. 1. p. 1-13.*

Toraya T. Radical catalysis of B12 enzymes: structure, mechanism, inactivation, and reactivation of diol and glycerol dehydratases. 2000. Cell. Mol. Life Sci. 57:106-127.*

Abe T et al. A Tetrahydrofolate-Dependent O-Demethylase, LigM, Is Crucial for Catabolism of Vanillate and Syringate in Sphingomonas paucimobilis SYK-6. 2005. Journal of Bacteriology. vol. 187, No. 6. p. 2030-2037. (Year: 2005).*

Peters M et al. Acquisition of a Deliberately Introduced Phenol Degradation Operon, pheBA, by Different Indigenous Pseudomonas Species. 1997. Applied and Environmental Microbiology. vol. 63, No. 12. p. 4899-4906. (Year: 1997).*

GenBank AAC64901.1. Retrieved on Oct. 27, 2017. Published Jan. 12, 2007 (Year: 2007).*

GenBank ABQ80638.1. Retrieved on Oct. 27, 2017. Published Jun. 3, 2011 (Year: 2011).*

GenBank AAN69312.1. Retrieved on Oct. 27, 2017. Published on Mar. 5, 2010 (Year: 2010).*

GenBank BAA23629.1. Retrieved on Oct. 27, 2017. Published on Nov. 27, 1997 (Year: 1997).*

Alén et al., "Gas-liquid Chromatographic Separation of Hydroxy Monocarboxylic Acids and Dicarboxylic Acids on a Fused-silica Capillary Column", Journal of Chromatography A, 1984, vol. 301, pp. 273-276.

Alonso et al., "Bimetallic Catalysts for Upgrading of Biomass to Fuels and Chemicals", Chemical Society Reviews, 2012, vol. 41, pp. 8075-8098.

(Continued)

*Primary Examiner* — Paul J Holland
(74) *Attorney, Agent, or Firm* — John Stolpa; Michael A. McIntyre

(57) ABSTRACT

This disclosure relates to compositions and methods for converting biomass to various chemical intermediates and final products including fuels. Aspects include the depolymerization of lignin, cellulose, and hemicellulose to a wide slate of depolymerization compounds that can be subsequently metabolized by genetically modified bacterium, and converted to cis,cis-muconic acid. Other aspects include the use of monometallic catalysts for converting the cis,cis-muconic acid to commodity chemicals and fuels, for example adipic acid and/or nylon.

27 Claims, 27 Drawing Sheets

(56) References Cited

OTHER PUBLICATIONS

Anderson et al., "Occurrence, Metabolism, Metabolic Role, and Industrial Uses of Bacterial Polyhydroxyalkanoates" Microbial Reviews, Dec. 1990, vol. 54, No. 2, pp. 450-472.
Bang et al., "DO-Stat Fed-Batch Production of cis, cis-Muconic Acid from Benzoic Acid by Pseudomonas putida BM014", Journal of Fermentation and Bioengineering, 1995, vol. 79, No. 4, pp. 381-383.
Bechthold et al., "Succinic Acid: A New Platform Chemical for Biobased Polymers from Renewable Resources", Chemical Engineering and Technology, May 2008, vol. 31, No. 5, pp. 647-654.
Bonawitz et al., "Disruption of Mediator Rescues the Stunted Growth of a Lignin-deficient *Arabidopsis* Mutant", Nature, May 2014, vol. 509, pp. 376-380.
Bozell et al., "Solvent fractionation of renewable woody feedstocks: Organosolv generation of biorefinery process streams for the production of biobased chemicals", Biomass and Bioenergy, 2011, vol. 35, pp. 4197-4208.
Chen et al., "Lignin Modification Improves Fermentable Sugar Yields for Biofuel Production", Nature Biotechnology, Jul. 2007, vol. 25, No. 7, pp. 759-761.
Chundawat et al., "Deconstruction of Lignocellulosic Biomass to Fuels and Chemicals", Annual Reviews Chemical and Biomolecular Engineering, 2011, vol. 2, pp. 121-145.
Ciesielski et al., "Engineering Plant Cell Walls: Tuning Lignin Monomer Composition for Deconstructable Biofuel Feedstocks or Resilient Biomaterials", Green Chemistry, 2014, vol. 16, pp. 2627-2635.
DĄbrowski et al., "Adsorption of Phenolic Compounds by Activated Carbon—A Critical Review", Chemosphere, 2005, vol. 58, pp. 1049-1070.
Davis et al., "Process Design and Economics for the Conversion of Lignocellulosic Biomass to Hydrocarbons: Dilute-acid and Enzymatic Deconstruction of Biomass to Sugars and Biological Conversion of Sugars to Hydrocarbons", NREL Technical Report NREL/TP-5100-60223, Oct. 2013, pp. 1-147.
de Boer et al., "The tac promoter: A functional hybrid derived from the trp and lac promoters", Proceedings of the National Academy of Sciences of the United States of America, Jan. 1983, vol. 80, pp. 21-25.
Van de Vyver et al., "Emerging Catalytic Processes for the Production of Adipic Acid", Catalysis Science & Technology, 2013, vol. 3, pp. 1465-1479.
Draths et al., "Environmentally Compatible Synthesis of Adipic Acid from D-glucose", Journal of the American Chemical Society, 1994, vol. 116, No. 1, pp. 399-400.
Fort et al., Green Chemistry, "Can Ionic Liquids Dissolve Wood? Processing and Analysis of Lignocellulosic Materials with 1-n-butyl-3-methylimidazolium chloride", 2007, vol. 9, pp. 63-69.
Franz et al., "Effect of Chemical Surface Heterogeneity on the Adsorption Mechanism of Dissolved Aromatics on Activated Carbon", Carbon, 2000, vol. 38, pp. 1807-1819.
Fuchs et al. "Microbial degradation of aromatic compounds—from one strategy to four", Nature Reviews—Microbiology, Nov. 2011, vol. 9, pp. 803-816.
Torres Galvis et al., "Supported Iron Nanoparticles as Catalysts for Sustainable Production of Lower Olefins", Science, Feb. 2012, vol. 335, No. 6070, pp. 835-838.
Gomi et al., "Purification and Characterization of Pyrocatechase from the Catechol-assimilating Yeast Candida maltosa", Agricultural and Biological Chemistry, 1988, vol. 52, No. 2, pp. 585-587.
Gurrath et al., "Palladium Catalysts on Activated Carbon Supports Influence of Reduction Temperature, Origin of the Support and Pretreatments of the Carbon Surface", Carbon, 2000, vol. 38, pp. 1241-1255.
Harwood et al., "The β-Ketoadipate Pathway and the Biology of Self-Identity", Annual Review of Microbiology, 1996, vol. 50, pp. 553-590.
Hernández-Arranz et al., "The Translational Repressor Crc Controls the Pseudomonas putida Benzoate and Alkane Catabolic Pathways Using a Multi-tier Regulation Strategy", Environmental Microbiology, Jan. 2013, vol. 15, No. 1, pp. 227-241.
Himmel et al., "Biomass Recalcitrance: Engineering Plants and Enzymes for Biofuels", Science, Feb. 2007, vol. 315, No. 5813, pp. 804-807.
Ji et al., "Direct Catalytic Conversion of Cellulose into Ethylene Glycol Using Nickel-Promoted Tungsten Carbide Catalysts", Angewandte Chemie, Oct. 2008, vol. 120, No. 44, pp. 8638-8641.
Jiménez et al., "Genomic Analysis of the Aromatic Catabolic Pathways from Pseudomonas putida KT2440", Environmental Microbiology, Dec. 2002, vol. 4, No. 12, pp. 824-841.
Karp et al., "Alkaline Pretreatment of Corn Stover: Bench-Scale Fractionation and Stream Characterization", ACS Sustainable Chemistry Engineering, 2014, vol. 2, No. 6, pp. 1481-1491.
Korhonen et al., "Hydrophobic Nanocellulose Aerogels as Floating, Sustainable, Reusable, and Recyclable Oil Absorbent", ACS Applied Materials & Interfaces, May 2011, vol. 3, No. 6, pp. 1813-1816.
Li et al., "One Step Recovery of Succinic Acid from Fermentation Broths by Crystallization", Separation and Purification Technology, 2010, vol. 72, pp. 294-300.
Linger et al., "Lignin Valorization through Integrated Biological Funneling and Chemical Catalysis", Proceedings of the National Academy of Sciences of the United States of America, Aug. 2014, vol. 111, No. 33, pp. 12013-12018.
Luque et al., "Chemical Transformations of Succinic Acid Recovered from Fermentation Broths by a Novel Direct Vacuum Distillation-Crystallisation Method", Green Chemistry, 2009, vol. 11, pp. 193-200.
Madon et al., "Experimental Criterion for the Absence of Artifacts in the Measurement of Rates of Heterogeneous Catalytic Reactions", Industrial & Engineering Chemistry Fundamentals, 1982, vol. 21, No. 4, pp. 438-447.
Martínez et al., "Biodegradation of Lignocellulosics: Microbial, Chemical, and Enzymatic Aspects of the Fungal Attack of Lignin", International Microbiology, Sep. 2005, vol. 8, No. 3, pp. 195-204.
Marx, "Development of a Broad-host-range SacB-based Vector for Unmarked Allelic Exchange", BioMed Central Research Notes, 2008, vol. 1, pp. 1-8.
Morales et al., "The Pseudomonas putida Crc Global Regulator Controls the Expression of Genes from Several Chromosomal Catabolic Pathways for Aromatic Compounds", Journal of Bacteriology, Mar. 2004, vol. 186, No. 5, pp. 1337-1344.
Moreno et al., "The Pseudomonas putida Crc Global Regulator Controls the Hierarchical Assimilation of Amino Acids in a Complete Medium: Evidence from Proteomic and Genomic Analyses", Proteomics, Jun. 2009, vol. 9, No. 11, pp. 2910-2928.
Mu et al., "Lignin Pyrolysis Components and Upgrading—Technology Review", BioEnergy Research, Dec. 2013, vol. 6, No. 4, pp. 1183-1204.
Myung et al., "Disassembly and Reassembly of Polyhydroxyalkanoates: Recycling Through Abiotic Depolymerization and Biotic Repolymerization", Bioresource Technology, 2014, vol. 170, pp. 167-174.
Nelson et al., "Complete Genome Sequence and Comparative Analysis of the Metabolically Versatile Pseudomonas putida KT2440", Environmental Microbiology, Dec. 2002, vol. 4, No. 12, pp. 799-808.
Niu et al., "Benzene-Free Synthesis of Adipic Acid", Biotechnology Progress, 2002, vol. 18, No. 2, pp. 201-211.
Nordlund et al., "Complete Nucleotide Sequence and Polypeptide Analysis of Multicomponent Phenol Hydroxylase from *Pseudomonas* sp. Strain CF600", Journal of Bacteriology, Dec. 1990, vol. 172, No. 12, pp. 6826-6833.
Ornston et al., "Properties of an Inducible Uptake System for β-Ketoadipate in Pseudomonas putida", Journal of Bacteriology, Feb. 1976, vol. 125, No. 2, pp. 475-488.
Parsell et al., "Cleavage and Hydrodeoxygenation (HDO) of C—O Bonds Relevant to Lignin Conversion Using Pd/Zn Synergistic Catalysis", Chemical Science, 2013, vol. 4, pp. 806-813.

(56) References Cited

OTHER PUBLICATIONS

Polen et al., "Toward Biotechnological Production of Adipic Acid and Precursors from Biorenewables", Journal of Biotechnology, 2013, vol. 167, No. 2, pp. 75-84.

Prasomsri et al., "Effective Hydrodeoxygenation of Biomass-Derived Oxygenates into Unsaturated Hydrocarbons by MoO3 Using Low H2 Pressure", Energy & Environmental Science, 2013, vol. 6, pp. 1732-1738.

Ragauskas et al., "Lignin Valorization: Improving Lignin Processing in the Biorefinery", Science, 2014, vol. 344, No. 6185, 1246843.

Salis et al., "Automated Design of Synthetic Ribosome Binding Sites to Control Protein Expression", Nature Biotechnology, Oct. 2009, vol. 27, No. 10, pp. 946-950.

Schäfer et al., "Small Mobilizable Multi-purpose Cloning Vectors Derived from the *Escherichia coli* Plasmids pK18 and pK19: Selection of Defined Deletions in the Chromosome of Corynebacterium glutamicum", Gene, Jul. 22, 1994, vol. 145, No. 1, pp. 69-73.

Schweigert et al., "Chemical Properties of Catechols and their Molecular Modes of Toxic Action in Cells, from Microorganisms to Mammals", Environmental Microbiology, 2001, vol. 3, No. 2, pp. 81-91.

Sifontes Herrera et al., "Sugar Hydrogenation over a Ru/C Catalyst", Journal of Chemical Technology and Biotechnology, 2011, vol. 86, No. 5, pp. 658-668.

Simmons et al., "Advances in Modifying Lignin for Enhanced Biofuel Production", Current Opinion in Plant Biology, Jun. 2010, vol. 13, No. 3, pp. 312-319.

Sluiter et al., "Compositional Analysis of Lignocellulosic Feedstocks. 1. Review and Description of Methods", Journal of Agriculture and Food Chemistry, 2010, vol. 58, pp. 9043-9053.

Somorjai et al., "Advancing the Frontiers in Nanocatalysis, Biointerfaces, and Renewable Energy Conversion by Innovations of Surface Techniques", Journal of the American Chemical Society, 2009, vol. 131, No. 46, pp. 16589-16605.

Sturgeon et al., "A Mechanistic Investigation of Acid-Catalyzed Cleavage of Aryl-Ether Linkages: Implications for Lignin Depolymerization in Acidic Environments", ACS Sustainable Chemistry & Engineering, 2014, vol. 2, No. 3, pp. 472-485.

Urbanus et al., "Intensified Crystallization in Complex Media: Heuristics for Crystallization of Platform Chemicals", Chemical Engineering Science, 2012, vol. 77, pp. 18-25.

van Duuren et al., "Generation of a catR Deficient Mutant of P. putida KT2440 that Produces cis, cis-Muconate from Benzoate at High Rate and Yield", Journal of Biotechnology, 2011, vol. 156, pp. 163-172.

Vardon et al., "Hydrothermal Catalytic Processing of Saturated and Unsaturated Fatty Acids to Hyrdrocarbons with Glycerol for in situ Hydrogen Production", Green Chem, 2014, vol. 16, No. 3, pp. 1507-1520.

Weber et al., "Biosynthesis of cis, cis-Muconic Acid and Its Aromatic Precursors, Catechol and Protocatechuic Acid, from Renewable Feedstocks by *Saccharomyces cerevisiae*", Applied and Environmental Microbiology, Dec. 2012, vol. 78, No. 23, pp. 8421-8430.

Wu et al., "Microbial Synthesis of cis,cis-muconic Acid from Benzoate by *Sphingobaterium* sp. GCG Generated from Effluent of a Styrne Monomer (SM) Production Plant", Enzyme Microbial Technology, Dec. 2004, vol. 35, Nos. 6-7, pp. 598-604.

Wu et al., "Microbial Synthesis of cis,cis-muconic Acid from Benzoate by *Sphingobaterium* sp. Mutants", Biochemical Engineering Journal, 2006, vol. 29, Nos. 1-2, pp. 35-40.

Yoshida et al., "Regioselective carboxylation of catechol by 3,4-dihydroxybenzoate decarboxylase of Enterobacter cloacae P", Biotechnology Letters, 2010, vol. 32, No. 5, pp. 701-705.

Yu et al., "Review of Pt-Based Bimetallic Catalysis: From Model Surfaces to Supported Catalysts", Chemical Reviews, 2012, vol. 112, No. 11, pp. 5780-5817.

Zakzeski et al., "The Catalytic Valorization of Lignin for the Production of Renewable Chemicals", Chemical Reviews, 2010, vol. 110, pp. 3552-3599.

Kim et al., PHAs Produced by *Pseudomonas putida* and *Pseudomonas oleovorans* Grown with n-Alkanoic Acids Containing Aromatic Groups, Macromolecules, 1999, vol. 32, pp. 6058-6064.

* cited by examiner

| Primer | Sequence (5'-3') |
|---|---|
| LP29 | GCGACAGGAAGCTGTATAGCCCTGCCTATTG |
| LP30 | GCTATACAGCTTCGTGTCGCTCAAGGCG |
| LP31 | ACCTCGTATGTGTGAAATTGTTATCCGCTCAC |
| LP32 | AATTTCACACACAATACGAGTAAGCACGATG |
| LP33 | CCGCGGCCGCCATCATTGAGACGCGGCG |
| LP34 | CCGGGCCGCGGTGACATAACCTCGAACTCAG |
| LP48 | CAGGACATCATCAGCCCTCCTGCAACGC |
| LP49 | GGAGGGCTGATGATGTCCTGCGCAAGCC |
| LP50 | AACCTCGAACTCAGATGCGCTGAACAGG |
| LP51 | GCGCATCTGAGTTCGGAGGTTATGTCACTGTGATTTG |
| LP53 | ATCCCGGGTACCGAGCTCGAATTCATGACCGTGAAAATTTCCCACACTG |
| LP54 | CAGCTATGACCATGATTACGAATTCTTGAATGCCGGCAACCCG |
| oCJ100 | CCGAAAAGTGCCACCTGACGTCGCCTTGCTGCTGCAG |
| oCJ101 | GCCGCAGTCGAGATCTGGAATTGTGAGAACGCCTGG |
| oCJ102 | AGATCTCGAGCTGGGCGCGGTGAAGCTTGGGGCC |
| oCJ103 | GCTGGATCCTCTAGTGAGCTCACGATTCCCCATTGCCAG |
| oCJ165 | CCAGGGCGTTCTCACAATTCCAGATCTG |
| oCJ166 | GAGCGGGCCCCAAGCTTCACGGCCGGCGCTCACTTCTTGTCGCTGAACAGCTCTGG |

Figure 11

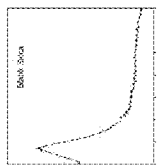
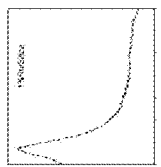
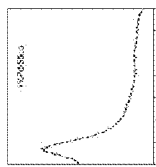
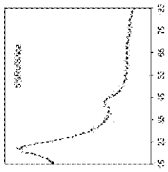
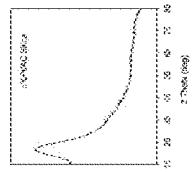
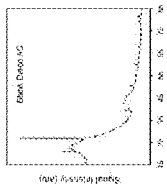
Figure 19a  Figure 19b  Figure 19c  Figure 19d  Figure 19e
Figure 19f  Figure 19g  Figure 19h  Figure 19i  Figure 19j

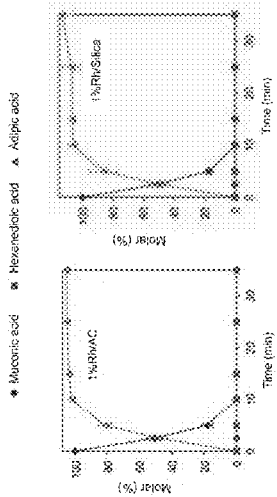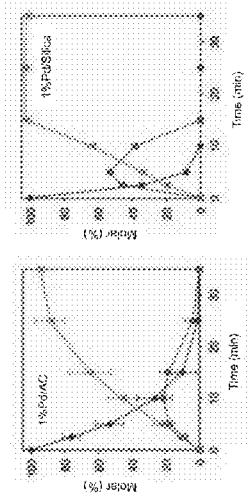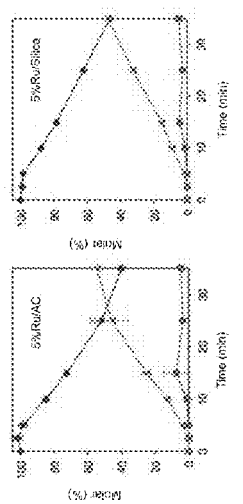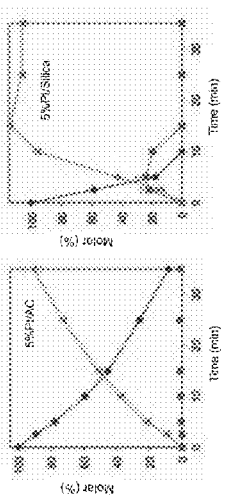
Figure 21a  Figure 21b  Figure 21c  Figure 21d  Figure 21e
Figure 21f  Figure 21g  Figure 21h  Figure 21i  Figure 21j

BIOMASS CONVERSION TO FUELS AND CHEMICALS

CROSS-REFERENCE TO RELATED APPLICATIONS

This application claims priority to and the benefit of U.S. Provisional Application No. 62/026,222, filed on Jul. 18, 2014, and U.S. Provisional Application No. 62/062,224, filed on Oct. 10, 2014, both entitled "Biomass Conversion to Fuels and Chemicals," and both of which are incorporated herein by reference in their entireties.

CONTRACTUAL ORIGIN

The United States Government has rights in this invention under Contract No. DE-AC36-08GO28308 between the United States Department of Energy and Alliance for Sustainable Energy, LLC, the Manager and Operator of the National Renewable Energy Laboratory.

REFERENCE TO SEQUENCE LISTING

This application contains a Sequence Listing submitted as an electronic text file entitled "14-04_ST25.txt," having a size in bytes of 141 kb and created on Jul. 20, 2015. Pursuant to 37 CFR § 1.52(e)(5), the information contained in the above electronic file is hereby incorporated by reference in its entirety.

BACKGROUND

Lignocellulosic biomass represents a vast resource for the production of renewable transportation fuels and chemicals to offset and replace current fossil fuel usage. For many decades, worldwide research efforts have focused on the development of cost-effective processes to selectively convert the polysaccharide components of plant cell walls, namely cellulose and hemicellulose, to fuels and chemicals through biological and chemical pathways. For example, in bioethanol production, biomass typically undergoes a mild thermochemical pretreatment step followed by enzymatic hydrolysis and fermentation to produce ethanol from the monomeric components of both cellulose and hemicellulose.

The lignin component of lignocellulosic biomass is an energy-dense, heterogeneous alkyl-aromatic polymer constructed from phenylpropanoid monomers used by plants for water transport and defense, and it is the second most abundant biopolymer on Earth after cellulose. Lignin is typically underutilized in most selective conversion processes for biofuel production. In the production of fuels and chemicals from biomass, lignin is typically burned for process heat because its inherent heterogeneity and recalcitrance make it difficult to selectively upgrade the monomers to value added products. This limited ability to utilize lignin, despite being the most energy dense polymer in the plant cell wall, is primarily due to its inherent heterogeneity and recalcitrance. Despite having a longer history of use as alternative renewable raw materials, cellulose and hemicellulose still remain important, high volume, readily available renewable raw materials, and next generation technologies that process these polysaccharides efficiently and economically are still needed. Thus, compositions, methods, and processes that can simultaneously and/or in parallel convert all of the substituent components of biomass, e.g. lignin, cellulose, and hemicellulose, to useful chemical intermediates, final chemical products (including fuels), is highly desirable to make steps towards lessening global dependency on petroleum.

However, in order to displace our current petrochemical consumption, an expanded renewable product slate is necessary, similar to the myriad of products currently derived from crude petroleum. This requires efficient and economically viable technology for converting all of the main constituents of biomass, cellulose, hemicellulose, as well as lignin, to useful final products, as well as chemical intermediates that can be converted to useful final products, utilizing either new technologies or existing technologies. The present application provides a suite of innovative technologies that may serve as cornerstones for future biomass-to-chemicals manufacturing plants, wherein these technologies focus on the first task of converting biomass to cis, cis-Muconic acid (hereinafter referred to as "muconic acid"), followed by the second task of converting the muconic acid to useful products including, but not limited to, adipic acid, 1,6-hexanediol, and hydrocarbon fuels.

Genetic engineering of microbial organisms is most commonly known due to the landmark Supreme Court case of Diamond v. Chakrabarty, wherein the court validated Chakrabarty's U.S. Pat. No. 4,259,444, directed to a *Pseudomonas putida* strain that had been engineered to degrade various oil derivatives, including octane and naphthalene.

Since then, researchers have pursued engineered microorganisms for biologically converting various biomass components to numerous chemical intermediates and products, including muconic acid, followed by conversion to adipic acid. Annual world-wide production of adipic acid in 1989 was estimated at 4.2 billion pounds and production has continued to grow since then. With U.S. production at 1.75 billion pounds in 1992, adipic acid consistently ranks as one the top fifty chemicals produced domestically. Nearly 90% of domestic adipic acid is used to produce nylon-6,6. Other uses for adipic acid include production of lubricants and plasticizers. Thus, there is a large economic driver behind the development of improved methods for muconic acid production, especially for the development of improved production methods that utilize renewable resources.

For example Koppisch et al. ("Koppisch") describe the use of engineered prokaryotic organisms for converting D-glucose to catechol and muconic acid (WO 2012/106257). This includes the introduction of exogenous decarboxylase genes, including aroY from *Klebsiella pneumoniae*, and the introduction of exogenous dioxygenase genes for converting catechol to muconic acid, for example catA.

U.S. Pat. No. 5,487,987 to Frost et al. ("Frost") describes the production of adipic acid through a metabolic pathway producing the cis, cis-muconic acid intermediate, also utilizing D-glucose as the starting material, and *Escherichia coli* genetically engineered to include genes endogenous to *Klebsiella pneumoniae* and *Acinetobacter calcoaceticus*.

Burk et al. ("Burk") describes the use of engineered microbial microorganisms to produce terephthalate through a muconic acid intermediate comprising trans,trans-muconate and/or cis, trans-muconate, starting with succinyl-CoA as a starting material (WO 2011/017560).

U.S. Pat. No. 8,133,704 to Baynes et al. ("Baynes") describes the use of genetically engineered microorganisms including *E. coli*, *C. glutanicum*, *B. flavum*, and *B. lactofermentum* for the eventual production of adipic acid, utilizing carbohydrate starting materials.

Weber et al. describe a genetically modified *Saccharomyces cerevisiae* to produce cis, cis-muconic acid utilizing aromatic amino acid pathways (Applied and Environmental Microbiology (2012) 78(23), 8421-8430).

*Pseudomonas putida* has been of particular interest recently, especially since completion of the genomic sequencing of *Pseudomonas putida* KT2440 (Environmetal Microbiology (2002) 4(12), 799-808). Jimenez et al. have characterized four of the main pathways in the KT2440 strain, including the protocatechuate and catechol branches of the β-ketoadipate pathway, the homogentisate pathway, and the phenylacetate pathway (Environmental Microbiology (2002) 4(12), 824-841).

Even before its genomic sequencing, scientists attempted to use *P. putida* as an organism for producing muconic acid. For example, U.S. Pat. Nos. 4,480,034 and 4,731,328 describe converting toluene to muconic acid, utilizing engineered microorganisms including *Pseudomonas putida*.

More recently, Bang et al. ("Bang") describe the use of a *P. putida* strain (BM014) for the production of cis, cis-muconic acid utilizing benzoic acid as a starting material (Journal of Fermentation and Bioengineering (1995) 79(4), 381-383). J. van Duuren et al. describe the use of *P. putida* KT2440 for the production of cis, cis-muconic acid utilizing benzoate as a starting material (Journal of Biotechnology (2011) 156, 163-172).

Thus, a review of the literature illustrates that a significant need remains for improved, flexible, reliable, economical technologies that are capable of converting a wide variety of biomass to industrially relevant chemical intermediates and final products, especially technologies that are capable of converting all of the key constituents of biomass; e.g. lignin, cellulose, and hemicellulose. To achieve this goal, robust genetically modified microorganisms, and/or mixtures of microorganisms are required that are capable of funneling chemical compounds through multiple metabolic pathways to common a common precursor or precursors, that can be subsequently converted to useful chemical intermediates and final products. In addition, novel upstream and downstream processing techniques are needed to assist with biomass fractionation, lignin and polysaccharide depolymerization, and precursor conversion to chemical intermediates and final products. The concepts presented herein provide some technologies that address these and other needs.

SUMMARY

An aspect of the present invention is a genetically modified microorganism that includes at least one exogenous gene addition, wherein the at least one added gene encodes at least one of a decarboxylase, a dehydratase, or a monooxygenase. In some embodiments of the present invention, a genetically modified microorganism may have at least one deleted gene that encodes at least one of a dioxygenase, a muconate lactonizing enzyme, or muconolactone isomerase. In some embodiments of the present invention, a microorganism may over-express at least one demethylase gene. In some embodiments of the present invention, a microorganism may include a deletion of at least one catabolite repression control gene.

In some embodiments of the present invention, the at least one exogenous gene may encode a decarboxylase from *Enterobacter cloacae*. In some embodiments of the present invention, the exogenous gene may be at least one of aroY, ecdB, or ecdD. In some embodiments of the present invention, the at least one exogenous gene may encode a dehydratase from *Bacillus cereus* or from P. pneumonia. In some further embodiments of the present invention, the exogenous gene may be at least one of aroZ or asbF. In some further embodiments of the present invention, the at least one exogenous gene may encode a monooxygenase from *Pseudomonas putida* CF600. In still further embodiments of the present invention, the exogenous gene may be at least one of dmpK, dmpL, dmpM, dmpN, dmpO, dmpP, or pheA. In still further embodiments of the present invention, the at least one deleted gene may be at least one of pcaH or pcaG. In some embodiments of the present invention, the at least one deleted gene from a microorganism may be at least one of catB or catC. In some embodiments of the present invention, the demethylase gene may be at least one of vanA, vanB, or ligM.

In some embodiments of the present invention, the microorganism may be at least one of a fungi, a prokaryote, or a prokaryotic microorganism. In some embodiments of the present invention, the microorganism may be a prokaryote or prokaryotic microorganism from the genus *Pseudomonas*. In some embodiments of the present invention, the microorganism may be a strain of *P. putida, P. fluorescens*, or *P. stutzeri*. In some further embodiments of the present invention, the microorganism may be a strain of *P. putida* KT2440.

A further aspect of the present invention is a process for producing muconic acid, where the process includes contacting a culture broth containing lignin depolymerization compounds with any of the genetically modified microorganism disclosed within this specification. In some embodiments of the present invention, the lignin depolymerization compounds may include at least one of p-coumaric acid, ferulic acid, benzoic acid, phenol, coniferyl alcohol, caffeic acid, vanillin, or 4-hydroxybenzoic acid, and at least a portion of the lignin depolymerization compounds are converted to catechol, and at least a portion of the catechol is converted to muconic acid.

A further aspect of the present invention is a process for producing adipic acid, where the process includes separating muconic acid from a culture broth comprising muconic acid, impurities, and microorganisms, purifying the separated muconic acid, and hydrogenating at least a portion of the purified muconic acid to produce the adipic acid or other chemicals. In some embodiments of the present invention, the separating may include at least one of centrifugation and/or filtration to produce muconic acid that is substantially free of the microorganism. In some embodiments of the present invention, the purifying may include contacting the separated muconic acid with an adsorbent, wherein the adsorbent removes at least a first portion of the impurities from the separated muconic acid.

In some embodiments of the present invention, the adsorbent may include activated carbon. In some embodiments of the present invention, the impurities removed may include at least one of benzoic acid, protocatechuic acid or 4-hydroxybenzoic acid. In some embodiments of the present invention, the purifying may include crystallizing at least a portion of the muconic acid from the separated muconic acid to form a muconic acid precipitate and a liquid that contains at least a portion of the impurities.

In some embodiments of the present invention, the purifying may include dissolving the muconic acid precipitate in a solvent, resulting in a liquid phase that includes muconic acid and a solid phase that includes at least a portion of the impurities, and separating the liquid phase from the solid phase. In some embodiments of the present invention, the separating may be by at least one of filtration or centrifugation. In some embodiments of the present invention, the hydrogenation may include contacting the liquid phase that includes muconic acid and diatomic hydrogen with a metallic catalyst. In some embodiments of the present invention, the metallic catalyst may include at least one of palladium, platinum, ruthenium, or rhodium. In some embodiments of the present invention, the at least one of palladium, platinum, ruthenium, or rhodium may be supported by activated carbon or silica. In some embodiments of the present invention, the metallic catalyst may include rhodium supported by activated carbon.

In addition to the exemplary aspects and embodiments described above, further aspects and embodiments will become apparent by reference to the drawings and by study of the following descriptions.

BRIEF DESCRIPTION OF DRAWINGS

The accompanying drawings are incorporated into and form a part of the specification to illustrate examples of how the aspects, embodiments, or configurations can be made and used and are not to be construed as limiting the aspects, embodiments, or configurations to only the illustrated and described examples. Further features and advantages will become apparent from the following, more detailed description of the various aspects, embodiments, or configurations.

FIG. 11 tabulates primer sequences used to genetically engineer some of the P. putida strains engineered for improved muconic acid production, according to exemplary embodiments of the present invention. Depicted are LP29 (SEQ ID NO:39), LP30 (SEQ ID NO:40), LP31 (SEQ ID NO:41), LP32 (SEQ ID NO:42), LP33 (SEQ ID NO:43), LP34 (SEQ ID NO:44), LP48 (SEQ ID NO:45), LP49 (SEQ ID NO:46), LP50 (SEQ ID NO:47), LP51 (SEQ ID NO:48), LP53 (SEQ ID NO:49), LP54 (SEQ ID NO:50), oCJ100 (SEQ ID NO:51), oCJ101 (SEQ ID NO:52), oCJ102 (SEQ ID NO:53), oCJ103 (SEQ ID NO:54), oCJ165 (SEQ ID NO:55), and oCJ166 (SEQ ID NO:56).

FIGS. 19a-j summarize XRD spectra of virgin catalysts used for batch reactor screening experiments and after metal loading and catalyst reduction, according to exemplary embodiments of the present invention. Spectra were also provided for blank powdered silica and activated carbon supports for reference (a, b).

FIGS. 21a-j summarize data from batch reactor catalyst activity screening for muconic acid hydrogenation), according to exemplary embodiments of the present invention. Reactions were performed in a minimum of duplicate batch reactors, with error bars indicating standard deviations.

Reaction conditions were as follows: temperature 24° C., muconic acid 200 mg, catalyst loading 15 mg, hydrogen pressure 24 bar, ethanol solvent 19.8 g.

Figure 22:
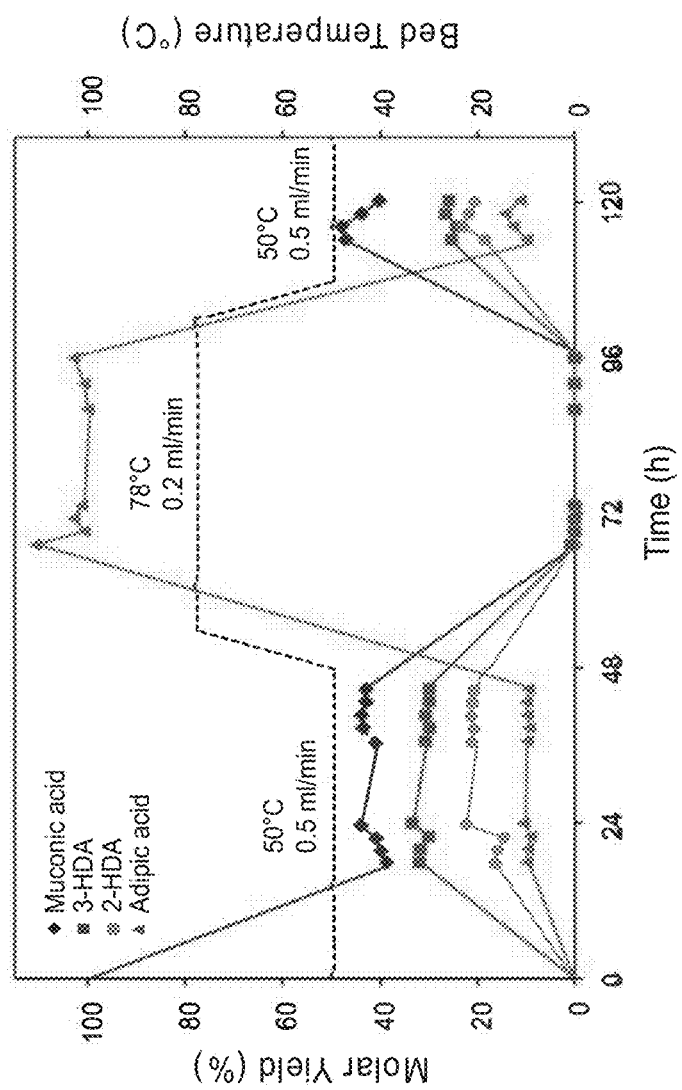

FIG. 22 illustrates product molar yields, catalyst bed temperature, and liquid feed rate during the 100-h time-on-stream stability test of 1% Rh/AC for muconic acid hydrogenation, according to exemplary embodiments of the present invention. Reaction conditions were as follows: muconic acid 1 wt % in ethanol, temperature and liquid flow rate as indicated, hydrogen 200 sccm at 24 bar, catalyst loading 1100 mg.

Figure 23:
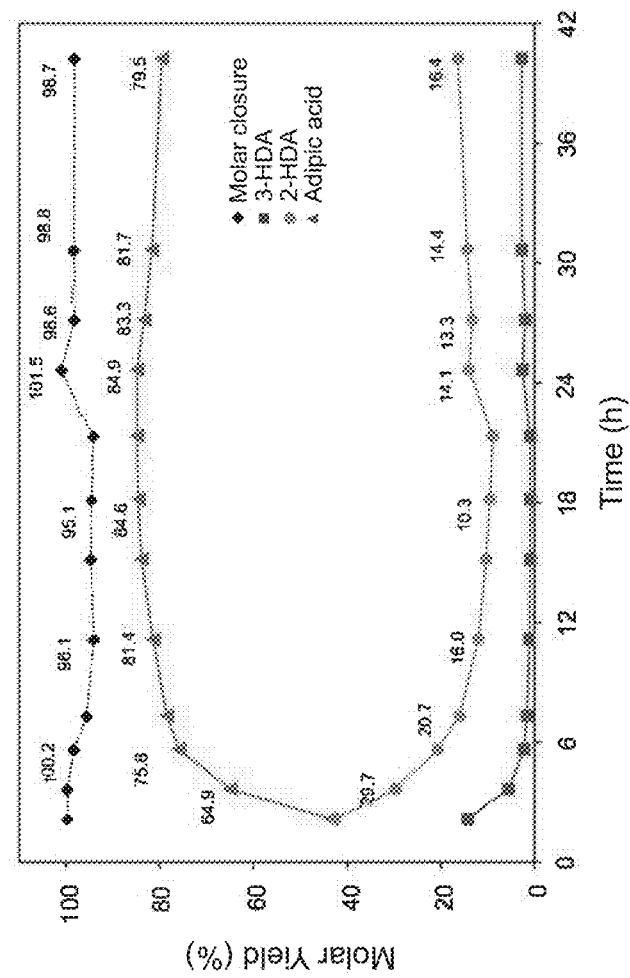

FIG. 23 illustrates preliminary trickle bed reactor results with 1% Pd/AC granules, demonstrating ~12 h to reach stead-state activity, according to exemplary embodiments of the present invention. Reaction conditions were as follows: muconic acid 1 wt % in ethanol, liquid flow rate 0.5 mL/min, catalyst bed temperature 72° C., hydrogen 200 sccm at 24 bar, and catalyst loading 200 mg of 1% Pd/AC granules.

Figure 24:
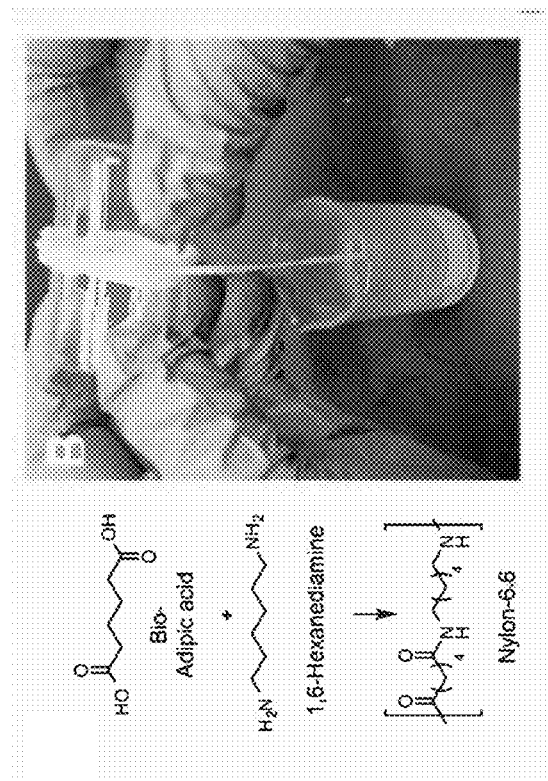

FIG. 24 illustrates a polymerization scheme for reacting bio-adipic acid with 1,6-hexanediamine to produce Nylon-6,6 (left), according to exemplary embodiments of the present invention. This method using bio-adipic acid produced from the catalytic hydrogenation of muconic acid (right). Adipic acid was initially reacted with thionyl chloride and dissolved to cyclohexane, prior to adding the solution to a basic 1,6-hexanediamine aqueous solution. Nylon "rope" was then pulled from the biphasic solution interface for subsequent characterization.

Figure 25:
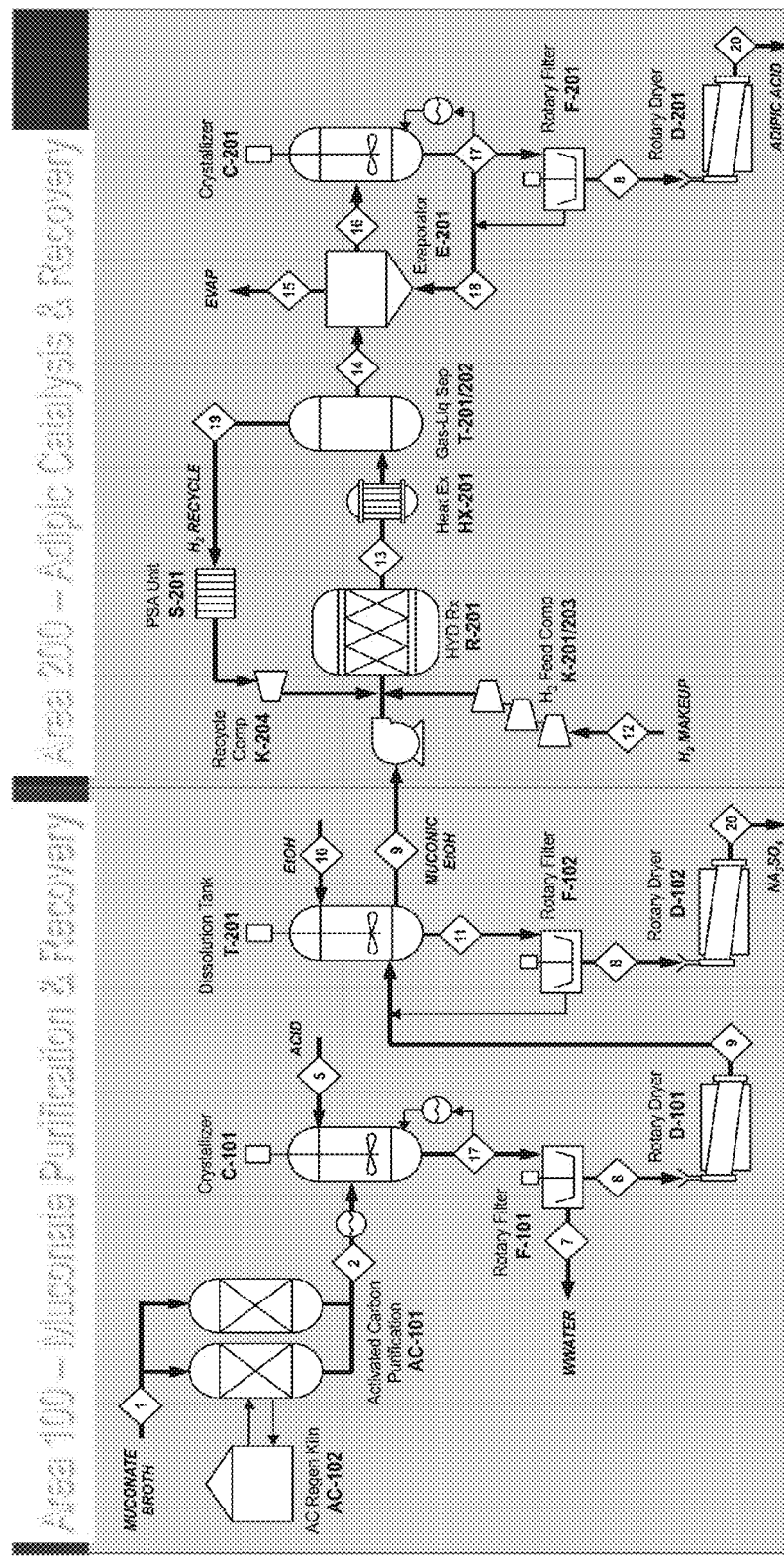

FIG. 25 illustrates a flow diagram for the separation/purification and upgrading areas of a biorefinery for the conversion of lignocellulosic materials to muconic acid and subsequently to adipic acid, according to exemplary embodiments of the present invention.

REFERENCE NUMBERS

| | |
|---|---|
| 100 | biorefinery |
| 110 | lignocellulosic biomass |
| 120 | pretreatment-fractionation |
| 130 | lignin depolymerization |
| 135 | polysaccharide depolymerization |
| 140 | microbial catalysis |
| 150 | separation/purification |
| 160 | catalytic hydrogenation |
| 170 | upgrading |
| 200 | bioreactor |
| 210 | muconic acid containing culture broth |
| 220 | purified muconic acid |
| 230 | final products |

DETAILED DESCRIPTION OF EXEMPLARY EMBODIMENTS

The following detailed description illustrates the invention by way of example and not by way of limitation. This description will clearly enable one skilled in the art to make and use the invention.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all molecular weight or molecular mass values given for nucleic acids or polypeptides are approximate, and are provided for description. Although methods and materials similar or equivalent to those described herein can be used in the practice or testing of this disclosure, suitable methods and materials are described below. The term "comprises" means "includes". In addition, the materials, methods, and examples are illustrative only and not intended to be limiting.

References in the specification to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

Those skilled in the art will understand that the genetic alterations, including metabolic modifications exemplified herein, are described with reference to a suitable host microorganism such as species from the *Pseudomonas* genus and their corresponding metabolic reactions or a suitable source microorganism for desired genetic material such as genes for a desired metabolic pathway. However, given the complete genome sequencing of a wide variety of microorganisms and the high level of skill in the area of genomics, those skilled in the art will readily be able to apply the teachings and guidance provided herein to essentially all other microorganisms. For example, the *Pseudomonas* metabolic alterations exemplified herein can readily be applied to other species by incorporating the same or analogous encoding nucleic acid from species other than the referenced species. Examples of other species include *Sphingobium* species (sp.) SYK-6, *Rhodococcus jostii*, *Cupriavidus necator*, *Acinetobacter* sp. ADP1, *Amycolatopsis* sp. ATCC 39116, *E. coli*, *S. cerevisae*, and/or fungi. Such genetic alterations include, for example, genetic alterations of species homologs, in general, and in particular, orthologs, paralogs or nonorthologous gene replacements.

Disclosed herein are methods for the integrated production of fuels, chemicals or materials from biomass, including lignin, cellulose, and hemicellulose, via catabolic pathways in bacteria. These methods enable a biological funneling approach for heterogeneous aromatic streams, thus opening a new route to produce renewable chemicals and fuels from biomass. Methods to couple this biological funneling to upstream lignin, cellulose, and/or hemicellulose depolymerization and downstream catalytic upgrading processes, thereby enabling a versatile, general approach to valorize lignin are also disclosed.

The methods presented herein may include the steps of lignin, cellulose, and/or hemicellulose depolymerization, biological funneling to a desired intermediate, followed by recovery and transformation to a value-added product. There is significant versatility in each step of this process such that it can be adapted to various feedstocks (e.g. raw materials), unit operations, and targeted fuel and chemical portfolios.

Figures 1A, 1B:
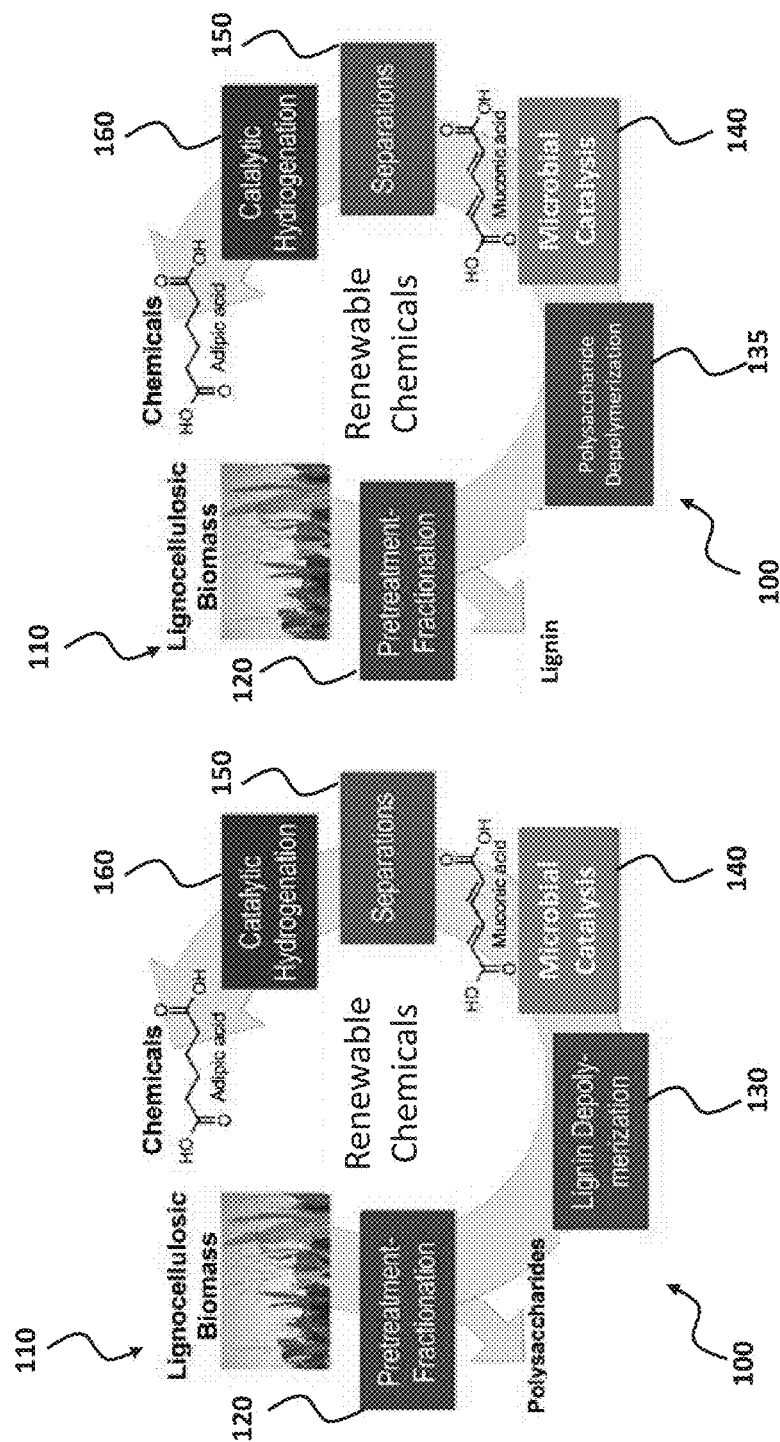
FIGS. 1a-c illustrate biorefinery processes for the conversion of biomass to chemical intermediates and final products, according to exemplary embodiments of the present invention.

FIG. 1a illustrates an exemplary biorefinery 100 that utilizes lignocellulosic biomass 110 to produce a high volume, commodity chemical, in this case adipic acid. FIG. 1a illustrates corn and/or corn stover as the lignocellulosic biomass 100 raw material (the carbon, oxygen, and hydrogen source). However, other examples of lignocellulosic biomass 110 that may be processed by such a biorefinery 100 include wheat straw, bagasse, wood, wood chips, bark, grass, municipal solid waste, and any other common and/or high volume biomass source characterized by a high content of cellulose, hemicellulose, lignin, or combinations thereof. In some embodiments, the biomass utilized may include at least one of wood, wood chips, bark, sawdust, wood pellets, wood briquettes, forestry waste, pine, poplar, willow, *Eucalyptus, Nothofagus*, sycamore, ash, *miscanthus*, switchgrass, reed canary grass, rye, giant reed, hemp, bamboo, sugar cane, bagasse, corn, corn stover, wheat, wheat straw, sugar beets, sorghum, rapeseed, waste vegetable oil, palm oil, algae, municipal solid waste, and/or yard clippings.

The biomass feed stream may be provided by mechanical conveyor and/or pneumatically. One skilled in the art will recognize that some preprocessing of the biomass may be required to enable the providing step. Examples of preprocessing include size reduction, screening, filtering, washing, and combinations thereof. Size reduction may be accomplished by chopping, cutting, grinding, and combinations thereof, using for example, a hammer-mill and/or knife-mill.

After receiving the lignocellulosic biomass, FIG. 1a illustrates that one or more pretreatment-fractionation operations 120 may pretreat and then separate the lignocellulosic biomass 110 into its component building blocks; e.g. lignin, cellulose, and hemicellulose. FIG. 1a also illustrates that the polysaccharide components may be separated from a main processing stream, resulting in a lignin-rich stream. The polysaccharides may then be directed to separate and independent processing operations for conversion to, for example, sugars, chemicals, and/or fuels by dedicated processing operations (not shown). The lignin stream may be subsequently directed through various processing operations that may include lignin depolymerization operations 130 and microbial catalysis operations 140, resulting in the production of useful chemical intermediates, for example muconic acid. The intermediate chemicals produced may then be processed through one or more separation/purification operations 150 to yield purified intermediate components (e.g. muconic acid), after which the intermediates may be packaged and/or stored for delivery and sale, or directed to down-stream processing, for subsequent upgrading to higher value chemicals and/or fuels. FIG. 1a illustrates an exemplary upgrading operation that includes catalytic hydrogenation 160, to convert muconic acid to adipic acid. Thus, biological funneling of lignin-derived monomers by engineered microorganisms may be combined with downstream upgrading to facilitate the development of an immense range of products.

Any pretreatment, fractionation, or depolymerization method that generates a lignin-containing stream is suitable for use in the methods described herein. Referring again to FIG. 1a, pretreatment and/or fractionation operations 120 of a lignocellulosic biomass 110 such as corn stover may include contacting the lignocellulosic biomass with an alkaline compound or biological or chemical catalyst to generate a soluble lignin-containing stream. Exemplary processing conditions include treatment with a base such as sodium hydroxide for a time ranging from several minutes to several hours at a temperature ranging from about 50° C. to about 200° C. at a solids loading of about 5 wt % to about 10 wt % solids in a mixer. These conditions may be varied by one skilled in the art, commensurate with the biomass source, the chemical or biological catalyst used, and other process and physical property parameters. Some embodiments of the present invention include lignin-polysaccharides separations using separation methods known to one skilled in the art. Some examples of lignin-polysaccharide separation methods which may be used in the present invention are described in U.S. Pat. Nos. 5,730,837; 2,037,001; 1,594,389; 1,888,025; 2,042,705; 3,932,207; 4,520,105; and 4,594,130, all of which are incorporated herein by reference in their entirety. Should definition discrepancies arise between publications incorporated herein by reference and the present written description and claims, the definitions provided herein shall over rule any other external definitions.

Referring again to FIG. 1a, lignin depolymerization operations 130 to low molecular weight aromatics may be achieved via thermal, biological, and/or catalytic processing. For example, white rot fungi and some bacteria may depolymerize lignin to its monomeric constituents using powerful oxidative enzymes. Lignin is composed of three monomeric phenylpropanoid units that differ in their degree of methoxylation, which are polymerized by carbon-carbon and carbon-oxygen bonds formed during lignin biosynthesis via radical coupling reactions. Thus, lignin depolymerization operations 130 may include a broad range of catalytic, thermal, and biological routes, and may yield a chemically heterogeneous pool of depolymerization intermediates, which may include for example, p-coumaric acid, ferulic acid, benzoic acid, phenol, coniferyl alcohol, caffeic acid, vanillin, and/or 4-hydroxybenzoic acid.

Referring again to FIG. 1a, microbial catalysis 140 may include biological funneling of one or more lignin depolymerization products/intermediates to produce molecules from acetyl-CoA, the tricarboxylic acid cycle, and beyond in carbon metabolism. In aerobic systems, a microbial catalysis operation 140 may utilize aromatic-catabolizing microorganisms that involve the use of "upper pathways". These "upper pathways" may employ a diverse battery of enzymes to funnel aromatic monomers and oligomers to key central intermediates, such as catechol and protocatechuic acid. From these central intermediates, dioxygenase enzymes may oxidatively cleave carbon-carbon bonds in the aromatic rings to produce ring-opened species that may then be "funneled" to central carbon metabolism routes, which may then ultimately lead to the tricarboxylic acid cycle. These catabolic pathways may enable engineered microorganisms to utilize a broad range of both natural and xenobiotic aromatic molecules as carbon and energy sources. In terms of chemicals and/or biofuels production, these metabolic pathways offer a direct, powerful means to biologically 'funnel' the heterogeneous slate of molecules produced from lignin depolymerization into either fuels or chemicals. An example of a useful intermediate chemical resulting from a microbial catalysis operation 140 (via biological funneling), as described above, is muconic acid.

The separation/purification operations 150 of the fuels, chemicals, and/or intermediates resulting from the microbial catalysis operation 140 may include a variety of unit operations. The selection of one or more specific unit operations for the separation/purification operation 150 will depend on the on the design criteria and operating conditions of the upstream processing; e.g. type of lignocellulosic biomass 110 utilized, and pretreatment-fractionation operation 120 efficiency and yield, and the species targeted for removal from the lignin stream. The separation/purification operation 150 needed may also depend on the details of the microbial catalysis operation 140; e.g. type of microorganism used, culture broth composition, etc. However, examples of unit operations for the separation/purification operation 150 may include filtration, centrifugation, distillation, vacuum distillation, adsorption, membrane separations, cross-flow membrane filtration, crystallization, and/or any other suitable separation/purification unit operations. For example, culture broth containing muconic acid from microbial catalysis 140 may be centrifuged and/or filtered to produce a solids stream (e.g. liquid stream with a relatively high concentration of cell matter) and a substantially solids-free liquid stream containing muconic acid. The muconic acid containing stream may then be treated by one or more unit operations, e.g. adsorption, crystallization, to produce a relatively pure muconic acid stream capable of downstream upgrading to value-added final products (e.g. chemicals, fuels, etc.)

Alternatively, a biorefinery 100 may also be designed to utilize predominantly the cellulosic components of the lignocellulosic biomass 110 to produce useful fuels and chemicals, as illustrated in FIG. 1b. In this example, lignin may be separated from the polysaccharides to form a polysaccharide-rich stream. The lignin may then be directed to separate and independent processing operations for conversion to lignin depolymerization products, for example aromatic compounds. The polysaccharide stream may be subsequently directed through various processing operations that may include polysaccharide depolymerization operations 135 and microbial catalysis operations 140, resulting in the production of useful chemical intermediates, for example muconic acid. The microbes (microorganisms) utilized for the microbial catalysis operation 140 may be engineered in this example to funnel polysaccharide degradation products (e.g. glucose, xylose, arabinose) to protocatechuic acid and/or catechol and subsequently to muconic acid. The muconic acid containing stream from the microbial catalysis operation 140 of FIG. 1b, may then be subsequently separated and/or purified in a separation/purification operation 150 operations. These operations for polysaccharide-based products may be significantly different from the separation/purification operations 150 utilized for the processing of the lignin-based products of FIG. 1a, because the microorganisms engineered to metabolize lignin depolymerization products may be significantly different from the microorganisms engineered to metabolize polysaccharide depolymerization products, as may be the culture media/broth and culture conditions. Thus, another biorefinery example may begin with something like the biorefinery of FIG. 1a, where the polysaccharide stream removed by the pretreatment-fractionation 120 operations may be fed to a polysaccharide depolymerization operation 130 operation like that of FIG. 1b. In so doing, both the polysaccharide stream and the lignin stream may have their own dedicated depolymerization operation, microbial catalysis operation, separation/purification operation, and upgrading operation (e.g. catalytic hydrogenation).

Figure 1C:
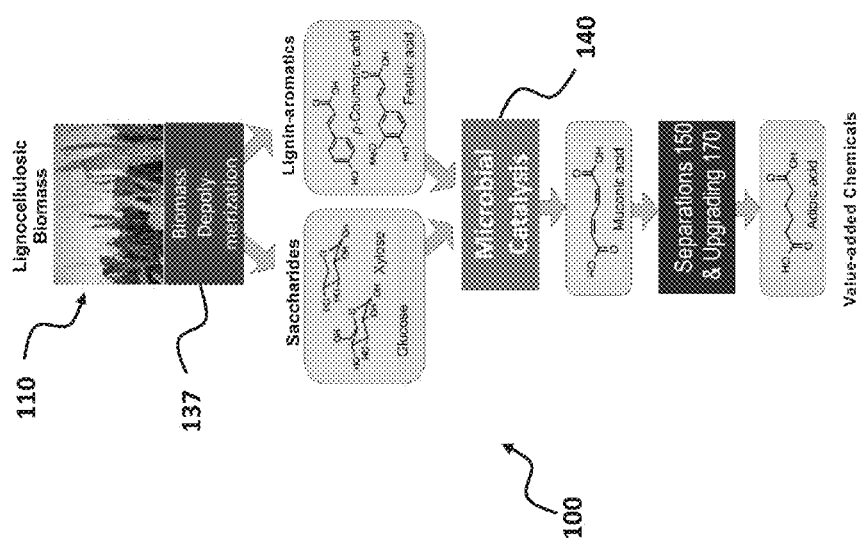

Alternatively, one or more microorganisms may be engineered to process both lignin depolymerization products and polysaccharide depolymerization products in a single microbial catalysis step. This option is illustrated in FIG. 1c. Thus, FIG. 1c combines FIG. 1a and FIG. 1b into a single series of operations wherein removal of a constituent biomass component (e.g. lignin or polysaccharides) does not occur. Instead, any pretreatment-fractionation steps (not shown) may be limited to, for example, washing steps for removing debris, metal removal steps, etc. Thus, biomass depolymerization 137 of lignin and cellulose/hemicellulose may occur simultaneously in a single processing step. Similarly, microbial catalysis 140 of the resultant lignin and polysaccharides depolymerization products may occur simultaneously in a single processing step (e.g. in a single bioreactor). Simultaneous culturing of the lignin and polysaccharides depolymerization products may include one biocatalyst/microorganism that has been engineered to process both lignin and polysaccharide depolymerization products to produce useful products (e.g. muconic acid). Alternatively, one or more biocatalysts/organisms may be engineered and/or optimized for the conversion of lignin depolymerization products to useful chemical intermediates and one or more additional biocatalysts/microorganisms may be engineered and/or optimized for the conversion of polysaccharides to useful chemical intermediates, with the various microorganisms used together in one or more culturing steps. Once the microbial catalysis 140 produces muconic acid, the resultant culture broth containing the muconic acid will be treated in a separations/purification operation 150 to produce a muconic acid stream of sufficient purity and quality to allow subsequent upgrading 170 (e.g. hydrogenation) to final products; e.g. adipic acid and/or nylon-6,6.

This disclosure will focus next on details and examples regarding the microbial catalysis 140 portion of the biorefinery 100 and will return later to the separation/purification operation 150 and the upgrading 170 portions of the biorefinery 100.

Microbial Catalysis

Microorganisms engineered and/or modified to funnel lignin depolymerization products and/or polysaccharide depolymerization products to useful molecules (e.g. chemicals and/or fuels) may include prokaryotes such as bacteria or eukaryotes such as yeasts or fungi. Further examples include *Pseudomonas* sp., *Sphingobium* sp. SYK-6, *Rhodococcus jostii*, *Cupriavidus necator*, *Acinetobacter* sp. ADP1, *Amycolatopsis* sp. ATCC 39116, *E. coli*, *S. cerevisae*, bacterial species from the genera *Streptomyces* or *Bacillus*, and/or fungi. Another example of a genetically modified bacterium may include the genus *Pseudomonas*. In some cases, the genetically modified microorganism may include at least one *Pseudomonas* species such as *aeruginosa*, *chlororaphis*, *fluorescens*, *pertucinogena*, *putida*, *stutzeri*, *syringae*, and/or *incertai sedis*. In other cases, the genetically modified microorganism may include at least one of *P. putida*, *P. fluorescens*, and/or *P. stutzeri*. In still other cases, the genetically modified microorganism may include at least one strain of *Pseudomonas putida* KT2440.

In some embodiments, the genetically modified microorganism may include at least one of *P. putida* group, including at least one of *P. cremoricolorata*, *P. entomophila*, *P. fulva*, *P. monteilii*, *P. mosselii*, *P. oryzihabitans*, *P. parafulva*, *P. plecoglossicida*, and/or *P. putida*. In some embodiments, the genetically modified microorganism may include at least one of the *P. fluorescens* group, including at least one of *P. antarctica*, *P. azotoformans*, *P. brassicacearum*, *P. brenneri*, *P. cedrina*, *P. corrugate*, *P. fluorescens*, *P. gessardii*, *P. libanensis*, *P. mandelii*, *P. marginalis*, *P. mediterranea*, *P. meridian*, *P. migulae*, *P. mucidolens*, *P. orientalis*, *P. panacis*, *P. protegens*, *P. proteolytica*, *P. rhodesiae*, *P. synxantha*, *P. thivervalensis*, and/or *P. tolaasii*.

As used herein, "exogenous" refers to something originating from another genetic source or species. So, as used herein, a genetically modified bacterium refers to a bacterium wherein the genetic modification is either the addition of genetic material from another species and/or the deletion of a portion of its own endogenous genetic material. So, as used herein, "endogenous" refers to native or naturally occurring genetic material of the microorganism itself.

As used herein, "gene" and "genetic source" and "genetic material" refer to a segment of nucleic acid that encodes an individual protein or RNA molecule (also referred to as a "coding sequence" or "coding region") and may include non-coding regions ("introns") and/or associated regulatory regions such as promoters, operators, terminators and the like, that may be located upstream or downstream of the coding sequence.

Genetic modifications and/or engineering to a microorganism to enable and/or improve the funneling of lignin depolymerization products and/or polysaccharide depolymerization products to useful intermediate compounds and/or useful fuels and/or chemicals may include at least one exogenous gene addition, at least one endogenous gene deletion, and/or the over-expression of at least one endogenous and/or exogenous gene. Such additions may be genomic and/or include the addition of plasmids that contain the desired gene.

Figure 2:
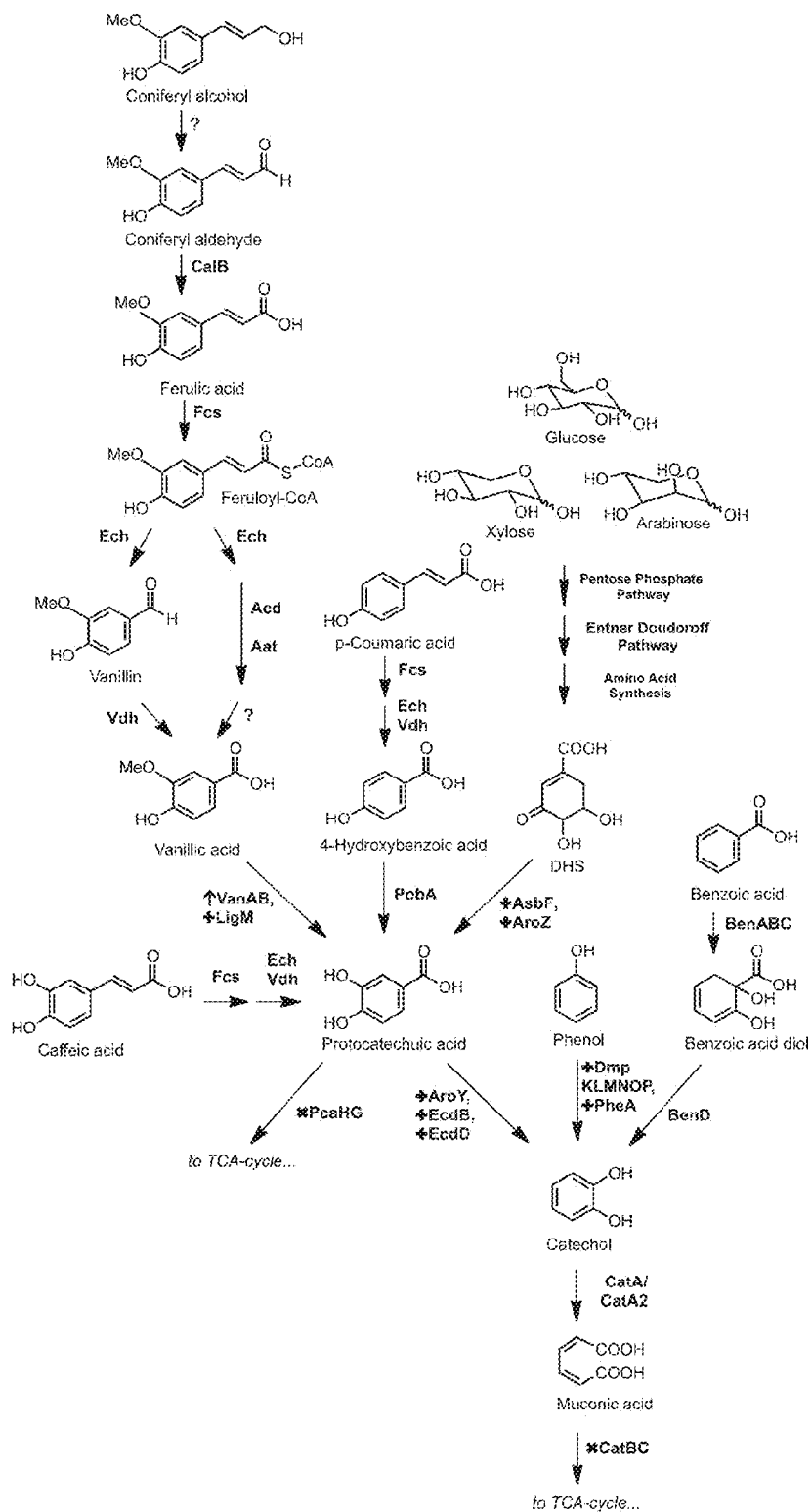
FIG. 2 illustrates engineered metabolic pathways in P. putida for converting both lignin depolymerization products and polysaccharide depolymerization products to muconic acid, according to exemplary embodiments of the present invention.

FIG. 2 illustrates exemplary engineered pathways for enabling an engineered microorganism to metabolize at least one of lignin, cellulose, hemicellulose, lignin depolymerization products, cellulose depolymerization products, and/or hemicellulose depolymerization products, to produce muconic acid. In this example, a strain of *P. putida* may include pathways for metabolizing lignin depolymerization products (e.g. aromatic compounds) and for metabolizing polysaccharide depolymerization products (e.g. glucose, xylose, arabinose, mannose, galactose, and/or rhamnose) to maximize the production of muconic acid. Referring again to FIG. 2, the exemplary genetically modified microorganism may convert coniferyl alcohol to coniferyl aldehyde and/or the genetically modified microorganism may convert the coniferyl aldehyde to ferulic acid and/or the genetically modified microorganism may convert the ferulic acid to at least one of vanillin and/or vanillic acid. A genetically modified microorganism may convert the vanillin to vanillic acid and/or the genetically modified microorganism may convert the vanillic acid to protocatechuic acid. A genetically modified microorganism may convert p-coumaric acid to 4-hydroxybenzoic acid and/or the genetically modified microorganism may convert 4-hydroxybenzoic acid to protocatechuic acid. A genetically modified microorganism may convert at least one of glucose, xylose, and/or arabinose to 3-dehydroshikimate (DHS) and/or the genetically modified microorganism may convert DHS to protocatechuic acid. A genetically modified microorganism may convert protocatechuic acid to catechol. A genetically modified microorganism may convert phenol to catechol. A genetically modified microorganism may convert benzoic acid to benzoic acid diol. A genetically modified microorganism may convert benzoic acid diol to catechol. A genetically modified microorganism may convert the catechol to muconic acid. In some examples, a genetically modified microorganism may be engineered to complete one or more of the reactions described above.

FIG. 2 illustrates that various genes coding a number of different enzymes may be manipulated, for example removed, added, over-expressed, and/or under-expressed to genetically engineer a microorganism (e.g. *P. putida*) to maximize the yield and/or selectivity of the target product molecule (e.g. muconic acid). For example, a microorganism may be engineered such that one or exogenous genes may be added to the microorganism. For example, a microorganism may be engineered such that one or more genes encoding exogenous decarboxylases may be added to the microorganism. A microorganism may be engineered such that one or more genes encoding exogenous monooxygenases may be added to the microorganism. A microorganism may be engineered such that one or more exogenous genes encoding dehydratases may be added to the microorganism. A microorganism may be engineered such that one or more genes encoding one or more exogenous monooxygenases, decarboxylases, and/or dehydratases may be added to the microorganism. Gene additions may be genomic additions or through the use of plasmids. Genes may be provided by any suitable and compatible microorganism for example *Enterobacter cloacae, Pseudomonas* sp., and/or *Bacillus cereus*. A microorganism may be engineered such that one or more genes encoding endogenous demethylases may be over-expressed by the microorganism.

In some embodiments, a microorganism may be engineered for optimized muconic acid production such that one or more endogenous genes may be removed from the microorganism. For example, a microorganism may be engineered such that one or more genes encoding catabolite repression control proteins may be removed, for example the gene encoding the Crc protein (see SEQ ID NO:13 and SEQ ID NO:14). A microorganism may be engineered such that one or more endogenous genes encoding dioxygenases may be removed from the microorganism. A microorganism may be engineered such that one or more endogenous genes encoding muconating lactonizing enzymes may be removed from the microorganism. A microorganism may be engineered such that one or more endogenous genes encoding muconolactone isomerases may be removed from the microorganism. In some embodiments, a microorganism may be engineered such that at least one gene encoding a catabolite repression control protein, a dioxygenase, a muconating lactonizing enzyme, and/or a muconolactone isomerase are removed from the microorganism.

A microorganism may be optimized for muconic acid production by the addition of several genes. For example, an exogenous decarboxylase that may be added to a microorganism may include 3,4-dihydroxybenzoate decarboxylase from *Enterobacter cloacae* subsp. *cloacae* (ATCC 13047). Such an exogenous decarboxylase may be encoded by an aroY gene (see SEQ ID NO:17 for the DNA sequence with the corresponding amino acid sequence shown by SEQ ID NO:18). In some embodiments, an exogenous dehydratase added to a microorganism may be from at least one of *Klebsiella pneumoniae, K. oxytoca, K. planticola, K. ornithinolytica, K. terrigena, Enterobacter cloacae, Enterobacter cancerogenus, Enterobacter hormaechei, Enterobacter mori* or combinations thereof. In some embodiments, an exogenous dehydratase may be engineered into a microorganism, where the exogenous dehydratase may be encoded by an aroZ gene. A microorganism may be modified by the addition of at least one exogenous monooxygenase encoded by at least one gene of dmpK (see SEQ ID NO:23 and SEQ ID NO:24), dmpL (see SEQ ID NO:25 and SEQ ID NO:26), dmpM (see SEQ ID NO:27 and SEQ ID NO:28), dmpN (see SEQ ID NO:29 and SEQ ID NO:30), dmpO (see SEQ ID NO:31 and SEQ ID NO:32), and/or dmpP (see SEQ ID NO:33 and SEQ ID NO:34) from the microorganism *Pseudomonas* sp. CF600 or the gene pheA from *Pseudomonas* sp. EST1001 (SEQ ID NO:35 and SEQ ID NO:36). For example, a microorganism may be modified to include the addition of each of dmpK, dmpL, dmpM, dmpN, dmpO, and dmpP, where such a modification is referred to herein as the addition of dmpKLMNOP. In some embodiments, at least one exogenous decarboxylase may be engineered into a microorganism, where the at least one exogenous decarboxylase may further include at least one gene of ecdB (see SEQ ID NO:19 and SEQ ID NO:20) and/or ecdD (see SEQ ID NO:21 and SEQ ID NO:22). At least one exogenous dehydratase may be engineered into a microorganism, where the exogenous dehydratase may be encoded by asbF (see SEQ ID NO:15 and SEQ ID NO:16). At least one endogenous demethylase may be over-expressed in an microorganism, where the demethylase may be encoded by at least one of vanA (see SEQ ID NO:5 and SEQ ID NO:6), vanB (see SEQ ID NO:7 and SEQ ID NO:8), or ligM (SEQ ID NO:37 and SEQ ID NO:38).

A microorganism may be optimized for muconic acid production by the deletion of at least one gene encoding a muconate lactonizing enzyme and/or a muconolactone isomerase, such as catB (see SEQ ID NO:1 and SEQ ID NO:2) and/or catC (see SEQ ID NO:3 and SEQ ID NO:4). In some examples, a microorganism may be manipulated to maximize muconic acid production by the removal of at least one dioxygenase, where the dioxygenase may be encoded by at least one gene of pcaH (see SEQ ID NO:9 and SEQ ID NO:10) and/or pcaG (see SEQ ID NO:11 and SEQ ID NO:12).

In some examples, at least one endogenous gene deletion to modify a microorganism for improved muconic acid production may include the deletion of at least one gene that encodes at least one enzyme that metabolizes muconic acid to a different molecule. In some embodiments, at least one endogenous gene deletion from a microorganism may include the deletion of at least one gene that encodes at least one enzyme in the β-ketoadipate pathway that metabolizes muconic acid to a different molecule.

In still further embodiments, the modified (e.g. engineered) microorganism may include at least one exogenous gene addition that encodes at least one enzyme of the pentose phosphate pathway and the addition of at least one gene that encodes at least one enzyme of a glycolytic pathway, such as the Embden-Meyerhof-Parnas pathway or the Entner-Doudoroff pathway. For example, some of the exogenous genes that may be added to a microorganism for improved muconic acid production may encode enzymes from the pentose phosphate pathway, such as at least one of glucose-6-phosphate dehydrogenase, gluconolactonase, 6-phosphogluconate dehydrogenase, ribulose-5-phosphate isomerase, ribulose-5-phosphate-3-epimerase, transketolase, and/or transaldolase. As another example, some of the exogenous genes that may be added to a microorganism for improved muconic acid production may encode enzymes from the Glycolysis pathway, such as at least one of hexokinase, phosphofructokinase, fructose-bisphosphate aldolase, triosephosphate isomerase, glyceraldehyde 3-phosphate dehydrogenase, phosphoclycerate kinase, phosphoglycerate mutase, enolase, and/or pyruvate kinase. In further embodiments, the modified microorganism may include at least one endogenous gene deletion where at the gene deleted encodes an enzyme for converting 3-dehydroshikimate (DHS) to an amino acid.

As used herein, the term "homologous" sequences of nucleic acids and proteins refer to sequences that have a statistically significant degree of similarity. In some embodiments of the present invention, any of the genes and the proteins and/or enzymes that they encode, e.g. dehydratases, decarboxylases, dioxygenases, monooxygenases, genes and enzymes from the pentose phosphate pathway, genes and enzymes from the Glycolysis pathway, may include nucleic acid and/or amino acid sequences that are homologous to the specific examples given in that the homologs have nucleic acid and/or amino acid sequences that are at least 70%, 75%, 85%, 90%, 91%, 92%, 93%, 94%, 95%, 96%, 97%, 98%, or 99% homologous to or identical to the sequences of the exemplary enzymes provided above. Nucleic acid sequences that do not show a high degree of identity may nevertheless encode similar amino acid sequences, due to the degeneracy of the genetic code. It is to be understood that changes in nucleic acid sequence can be made using this degeneracy to produce multiple nucleic acid sequences that each encode substantially the same protein.

As a result of at least one of the genetic modifications described above, a genetically engineered microorganism may be used to metabolize at least one of lignin, cellulose, hemicellose, or combinations thereof, to produce useful final products, chemicals, and chemical intermediates. Further, a modified microorganism may be used to metabolize at least one of the intermediations of lignin depolymerization, cellulose depolymerization, hemicellose depolymerization, or combinations thereof, to produce useful final products, chemicals, and chemical intermediates. For example, a modified microorganism (e.g. a bacterial strain such as $P.$ $putida$) may be engineered to metabolize at least one of carbohydrates, cellobiose, polysaccharides, C5 sugars, C6 sugars, and/or lignin depolymerization products. Sugars that may be metabolized in some embodiments by modified microorganisms described herein may include at least one of xylose, glucose, galactose, arabinose, mannose, or combinations thereof. Lignin depolymerization products that may be metabolized by some embodiments of the modified microorganisms described herein may include least one of phenylpropanoid units, coniferyl alcohol-derived constituents, syringyl structures, coniferyl structures, p-coumaryl groups, or mixtures thereof. In still further embodiments, compounds that may be metabolized by some examples of the modified microorganisms as described herein may include at least one of p-coumaryl alcohol, syringyl alcohol, coniferyl alcohol, coniferyl aldehyde, ferulic acid, feruloyl-CoA, vanillin, vanillic acid, caffeic acid, or mixtures thereof. Other chemical compounds that may be metabolized by some examples of the genetically engineered microorganisms described herein include at least one of 3-dehydroshikimate, p-coumeric acid, 4-hydroxybenzoic acid, phenol, benzoic acid, benzoic acid diol, or mixtures thereof. In some embodiments, a modified microorganism as described herein, engineered to metabolize at least one of lignin, cellulose, hemicellulose, and their respective depolymerization products, may achieve this metabolism by use of at least one of the β-ketoadipate pathway, the Embden-Meyerhof-Parnas pathway, the Entner-Doudoroff pathway, the pentose phosphate pathway, and/or an amino acid synthesis pathway.

Referring again to FIG. 2, several organic acids are shown: e.g. ferulic acid, vanillic acid, caffeic acid, protocatechuic acid, p-coumaric acid, 4-hydroxybenzoic acid, benzoic acid, etc. Organic acids in aqueous solutions will reach an equilibrium concentration/ratio of the conjugate acid (e.g., muconic acid) with the conjugate base (e.g., muconate). The relationships defining these equilibrium concentrations and ratios are controlled at least by the acid dissociation constant and solution pH and often both the acid and base form will be present in an aqueous solution (e.g. culture broth). Thus, for simplification purposes, as used herein reference to either the conjugate acid form (e.g., muconic acid) or the conjugate base form (e.g., muconate) of a molecule means both forms of molecule are present unless specified otherwise.

Figure 3:
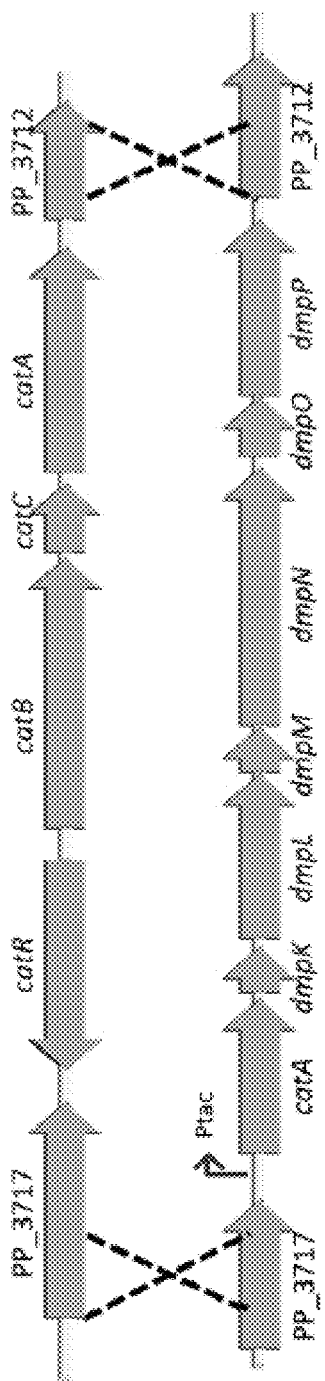
FIG. 3 summarizes engineered modifications to the genome of a P. putida strain to increase the production of muconic acid, followed by conversion to chemical intermediates, according to exemplary embodiments of the present invention.
Figure 4:
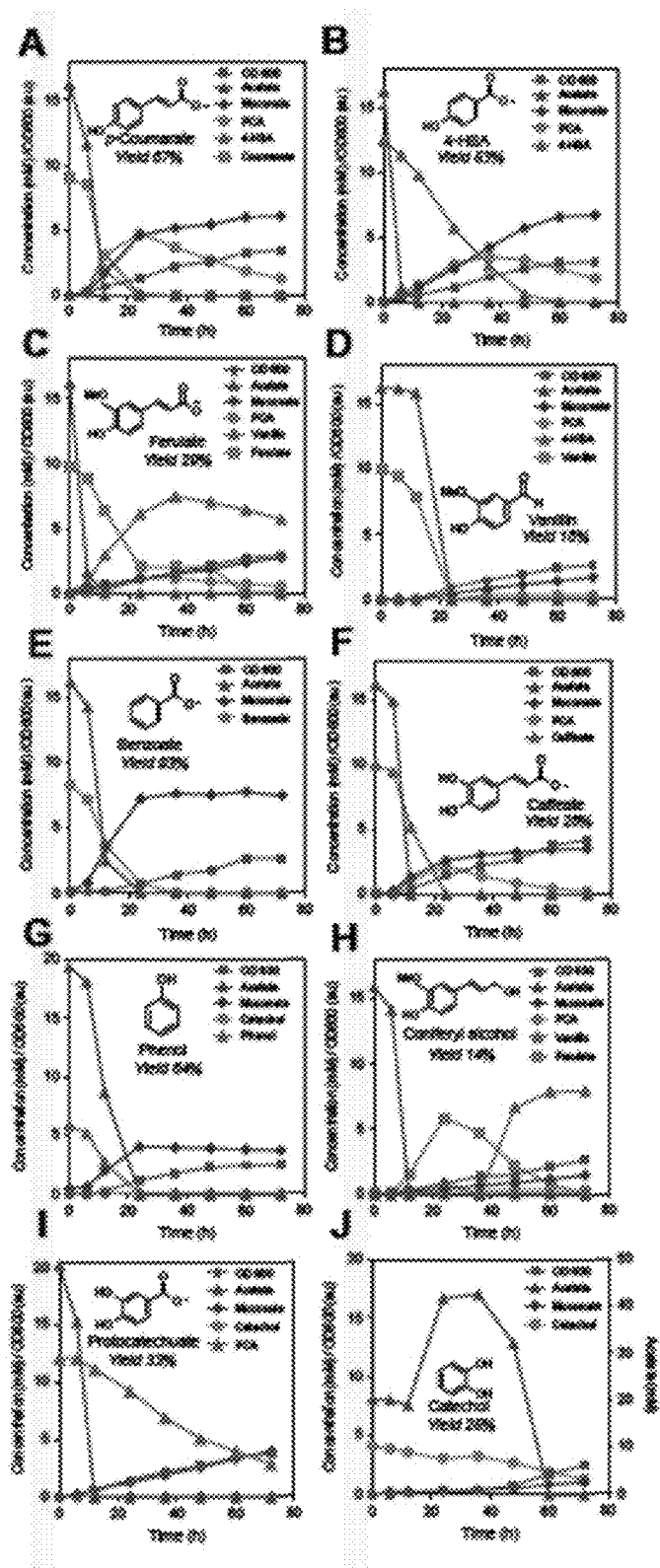
FIG. 4 summarizes experimental culture results obtained using an engineered strain of Pseudomonas putida metabolizing various substrates for their conversion to muconic acid, according to exemplary embodiments of the present invention.

FIG. 4 summarizes experimental results from an engineered $P.$ $putida$ KT2440 strain. For this example, the strain was modified to capture aromatic species metabolized through protocatechuic acid. This was accomplished by replacing the gene pcaHG encoding a protocatechuate 3,4 dioxygenase with aroY encoding a protocatechuate decarboxylase from *Enterobacter cloacae*. This enabled the conversion of protocatechuic acid and upstream metabolites to catechol while simultaneously eliminating further catabolism of protocatechuic acid to β-ketoadipate via the TCA-cycle (see FIG. 2, β-ketoadipate not shown). The same *P. putida* strain was then further engineered to expand substrate utilization and to eliminate further metabolism of muconic acid. This was accomplished be removing CatA and CatB by removing a genomic section containing catR, catBC, and the promoter for catBCA and replacing it with the Ptac promoter, which allowed the constitutive expression of catA. Lastly, as phenol is a commonly derived lignin intermediate, the genes encoding the phenol monooxygenase from *Pseudomonas* sp. CF600, dmpKLMNOP were integrated into the genome downstream of catA to form an operon driven by the Ptac promoter (see FIG. 3).

The metabolic performance of the engineered *P. putida* strain (called KT2440-CJ103) was then evaluated in shake-flask experiments to demonstrate substrate utilization and production of muconic acid from model lignin-derived monomers, using acetate as a carbon and energy source. FIG. 4 illustrates the metabolism of benzoate (benzoic acid), p-coumarate, phenol, 4-hydroxybenzoic acid (4-HBA), ferulate (ferulic acid), protocatechuate (protocatechuic acid), vanillin, caffeate (caffeic acid), coniferyl alcohol, and catechol by KT2440-CJ103. KT2440-CJ103 successfully produced muconic acid from catechol, phenol, and benzoate via the catechol branch (see FIG. 2), as well as from protocatechuate, coniferyl alcohol, ferulate, vanillin, caffeate, p-coumarate, and 4-hydroxybenzoate via the protocatechuate branch. Muconic acid yields ranged from about 14% using coniferyl alcohol as a substrate to about 93% utilizing benzoate. Compounds metabolized through vanillate (see FIG. 2; e.g. coniferyl alcohol, ferulate, and vanillin) demonstrated lower yields with accumulation of the intermediate vanillate. In contrast, compounds metabolized through the catechol branch (see FIG. 2; e.g. phenol, catechol, benzoate), as well as p-coumarate and 4-HBA, provided higher yields.

Figure 5:
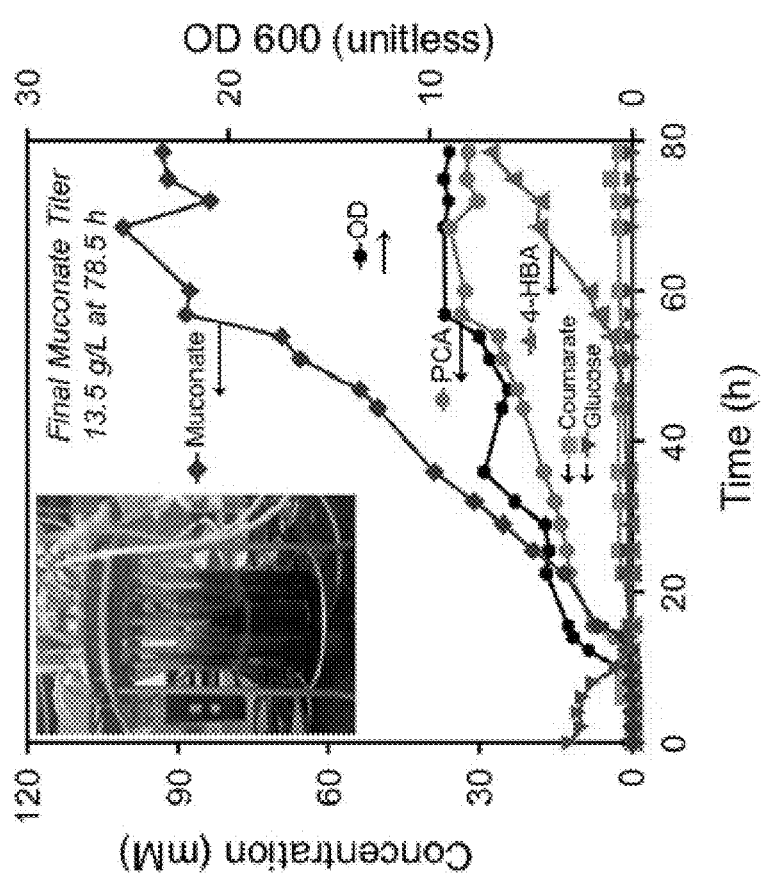
FIG. 5 summarizes experimental results from a DO-stat fed-batch experiment utilizing an engineered strain of P. putida (KT2440-CJ103) to convert p-coumarate to muconic acid, according to exemplary embodiments of the present invention.

The performance of the engineered *P. putida* strain (KT2440-CJ103) was also studied in a fed-batch bioreactor experiment to understand the effects increased aeration, pH control, and a metered dosing of substrates on *P. putida* growth and the conversion of substrate to muconic acid. The results are illustrated in FIG. 5. Dissolved oxygen static (DO-stat) fed-batch biological conversion by KT2440-CJ103 yielded a muconic acid titer of about 13.5 g/L after about 78.5 hours using p-coumarate as a model lignin monomer substrate, over 15 times greater than the shake flask results shown in FIG. 4. Preliminary experiments indicated that muconic acid production from p-coumarate was significantly inhibited by the presence of excess glucose or acetate, potentially due to catabolite repression control or other regulatory inhibition. Therefore, DO-stat was used to maintain glucose levels below 1 mM while co-feeding p-coumarate and ammonium sulfate. During the course of cultivation, protocatechuate (protocatechuic acid) buildup occurred. Moreover, as the cultivation progressed past 60 hours, muconic acid concentrations plateaued and 4-HBA, a metabolite upstream of protocatechuic acid, accumulated.

Figure 6:
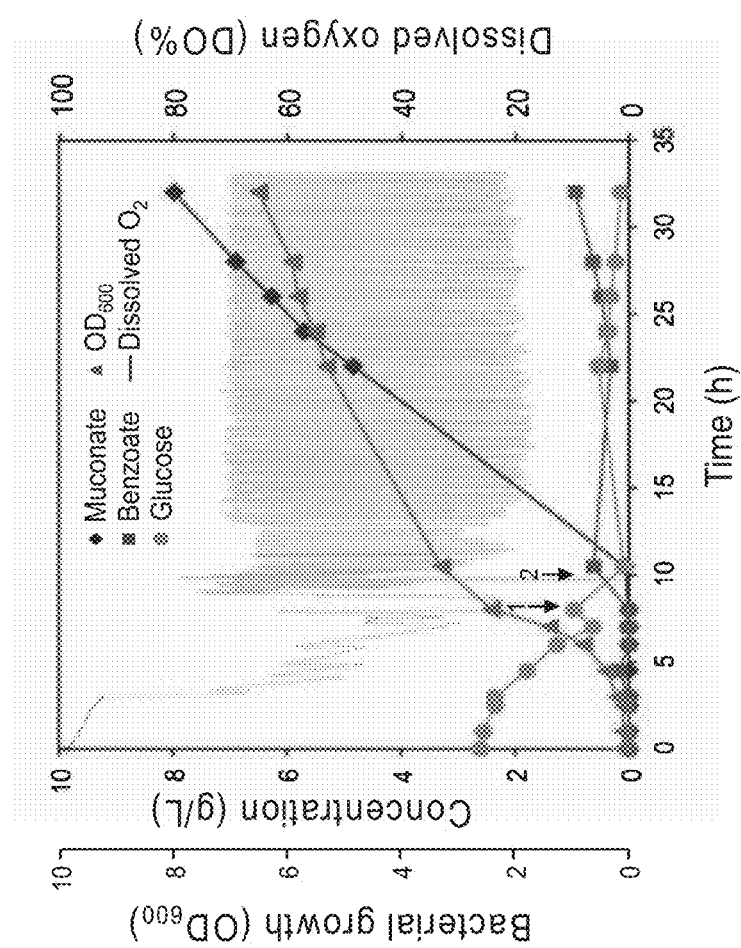
FIG. 6 summarizes experimental results from a DO-stat fed-batch experiment utilizing an engineered strain of P. putida (KT2440-CJ103) to convert benzoate to muconic acid, according to exemplary embodiments of the present invention.

FIG. 6 illustrates another set of fed-batch results where the *P. putida* KT2440-CJ103 strain was used to convert benzoate (benzoic acid) to muconic acid. In this example, glucose was used as a carbon source to support biological growth and function. Benzoate feeding was based on DO stat control, while pH was controlled using NaOH, resulting in sodium muconate as the predominant species at a pH of about 7. Muconate was produced at a titer of about 7.97 g/L after about 32 hours, while residual benzoic acid was present at about 0.94 g/L. After terminating the fed-batch run, cells were removed by centrifugation and filtration for subsequent broth processing.

Numerous other strains of *P. putida* KT2440 have been engineered and tested for their ability to convert lignin depolymerization products to muconic acid, several examples of which follow below.

Example 1

Co-expression of decarboxylase subunits, EcdB and EcdD, to enhance the activity of the protocatechuate decarboxylase, AroY and, subsequently, increase production of muconic acid from aromatic molecules metabolized through protocatechuate.

As mentioned above, some experiments with *P. putida* KT2440-CJ103 for producing muconic acid from aromatic molecules metabolized through protocatechuate (PCA), including p-coumarate, 4-hydroxybenaote (4-HBA), ferulate, and vanillin, demonstrated an accumulation of protocatechuate that reduced muconic acid yields. This suggested that the activity of the heterologously expressed protocatechuate decarboxylase that converts protocatechuate to catechol, AroY, may be insufficient. In an attempt to eliminate this bottleneck, enzymes from *Enterobacter cloacae* subsp. *cloacae* (ATCC 13047), EcdB and EcdD along with AroY (also from *Enterobacter cloacae* subsp. *cloacae* (ATCC 13047)) were engineered into a *P. putida* strain that was otherwise engineered to produce muconic acid from aromatic molecules. Metabolism of p-coumarate with the co-expression of AroY with EcdB (FIG. 7b) or with EcdB and EcdD (FIG. 7c), exhibited increased activity relative to AroY alone (FIG. 7a), which ultimately resulted in reduced accumulation of protocatechuate and greater production of muconic acid from p-coumarate.

Figure 7A:
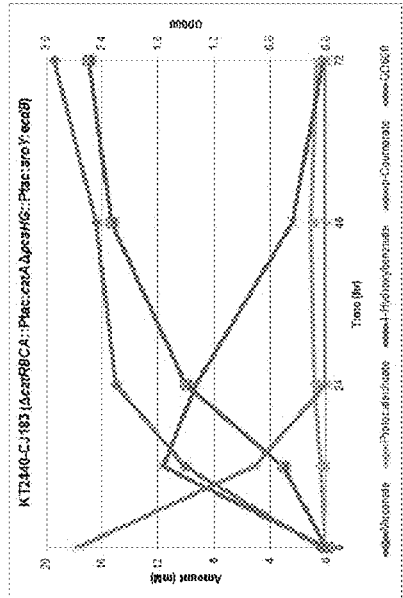
FIGS. 7a-c summarize experimental results obtained from an engineered strain of P. putida that coexpresses decarboxylase subunits, EcdB and EcdD, to enhance the activity of the protocatechuate decarboxylase, AroY, according to exemplary embodiments of the present invention.
Figure 7B:
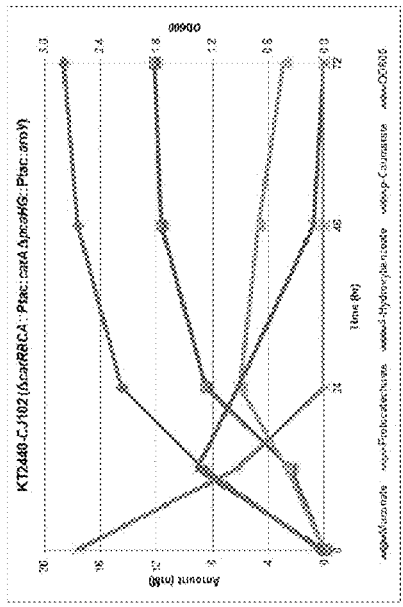
Figure 7C:
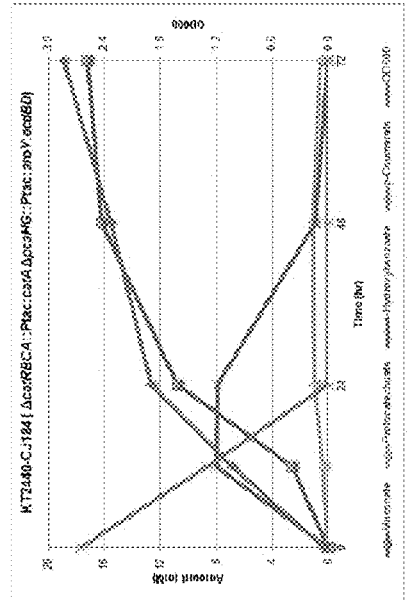

Referring to FIG. 7a which illustrates the performance of *P. putida* strain KT2440-CJ102, the text in parenthesis, ΔcatRBCA::Ptac:catA ΔpcaHG::Ptac:aroY, means the following. First, the gene or genes immediately following a Δ symbol have been deleted from the genome. The double-colon following the deleted gene(s) refers to replacing the deleted gene(s) with the genetic element, gene or genes that immediately follow the double-colon. Finally, the single colon refers to genetic fusion of the gene before the colon to the gene following the colon. Thus, two genetic modifications were made to strain KT2440 to produce new strain KT2440-CJ102 (see FIG. 7a). First, the catRBCA genes were deleted and replaced by a DNA fragment comprising the Ptac promoter upstream of the catA gene and second, the pcaHG genes were deleted and replaced with a DNA fragment comprising the Ptac promoter upstream of the and aroY gene. Referring to FIG. 7b, the KT2440-CJ183 strain was constructed by modifying the KT2440 strain: first, the catRBCA genes were deleted and replaced by a DNA fragment comprising the Ptac promoter upstream of catA and second, the pcaHG genes were deleted and replaced with a DNA fragment comprising the Ptac promoter upstream of aroY and ecdB. Referring to FIG. 7c, the KT2440-CJ184 strain was constructed by modifying the KT2440 strain: first, the catRBCA genes were deleted and replaced with a DNA fragment comprising the Ptac promoter upstream of catA and second, the pcaHG genes were deleted and replaced with a DNA fragment comprising the Ptac promoter upstream of aroY, and ecdBD (ecdB and ecdD).

Example 2

Over-expression of VanAB for enhanced conversion of vanillate (aromatic pathways) to protocatechuate and, subsequently, increased production of muconic acid from coniferyl alcohol pathway metabolites.

Figure 8B:
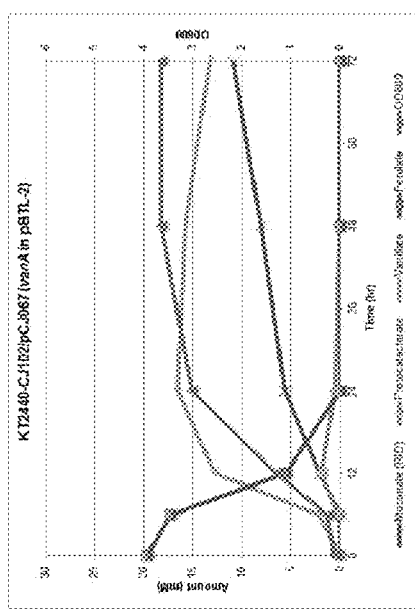
FIGS. 8a-d summarize experimental results obtained from an engineered strain of P. putida that over-expresses VanAB for enhanced conversion of vanillate to protocatechuate to enable enhanced muconic acid production, according to exemplary embodiments of the present invention.
Figure 8A:
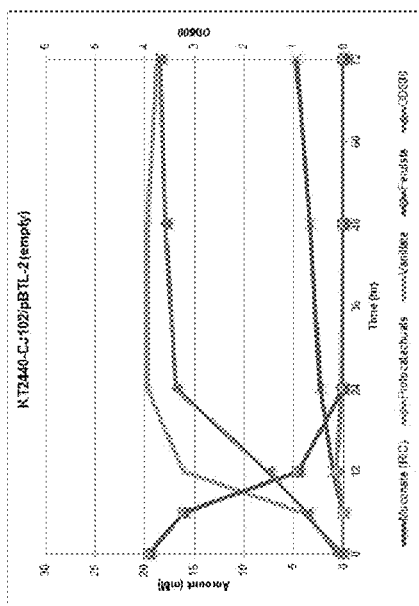
Figure 8D:
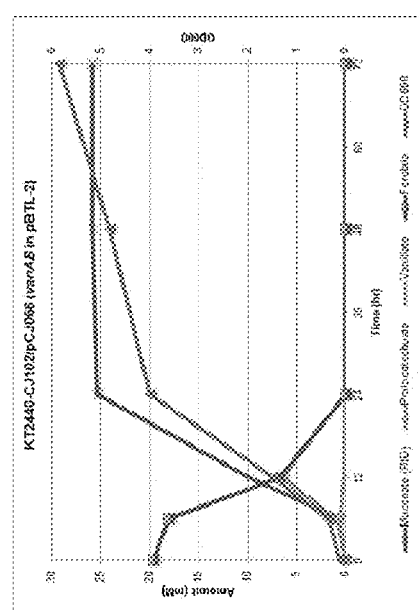
Figure 8C:
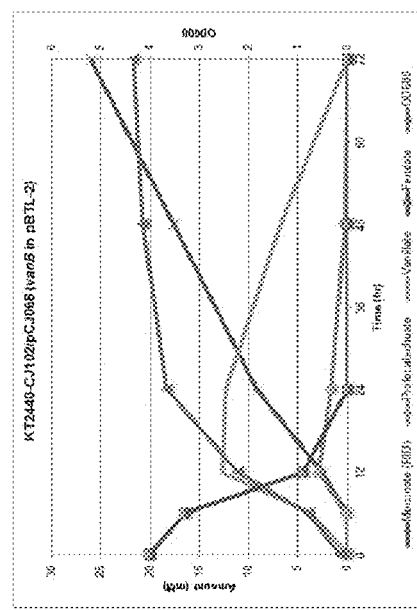
Figure 9A:
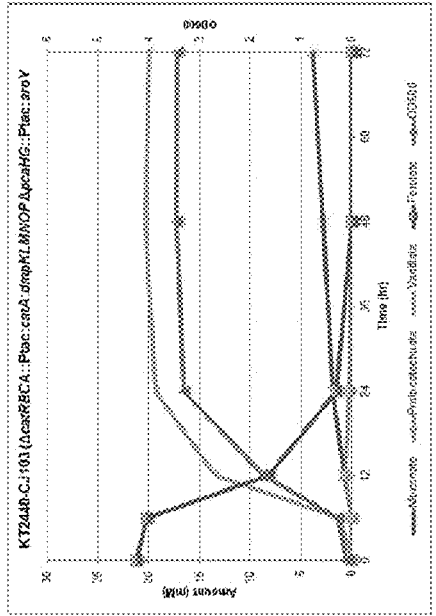
FIGS. 9a-h summarize experimental results obtained from an engineered strain of P. putida with deregulation of Carbon Catabolite Repression to enhance aromatic catabolism and, subsequently, increase production of muconic acid from aromatic molecules, according to exemplary embodiments of the present invention.
Figure 9C:
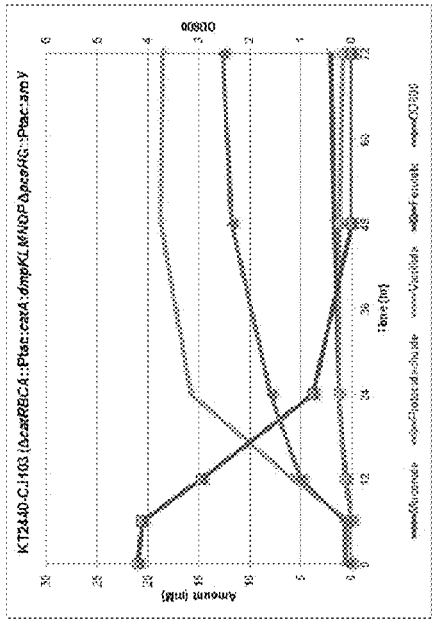
Figure 9E:
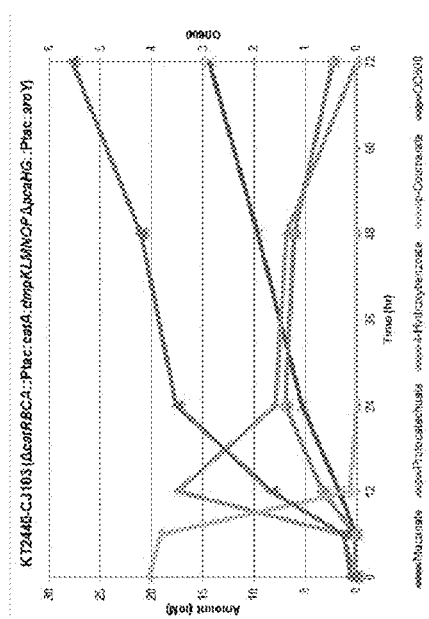
Figure 9G:
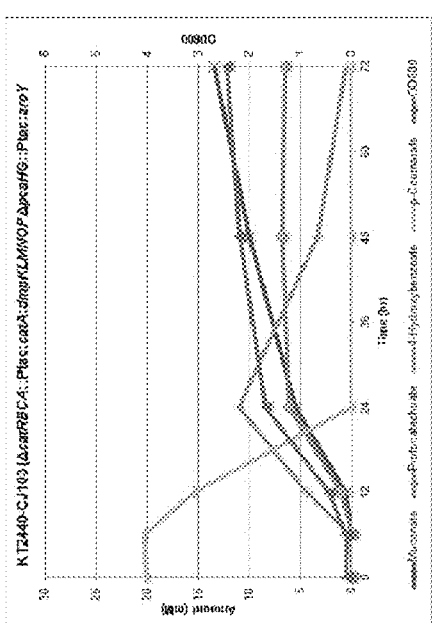
Figure 9B:
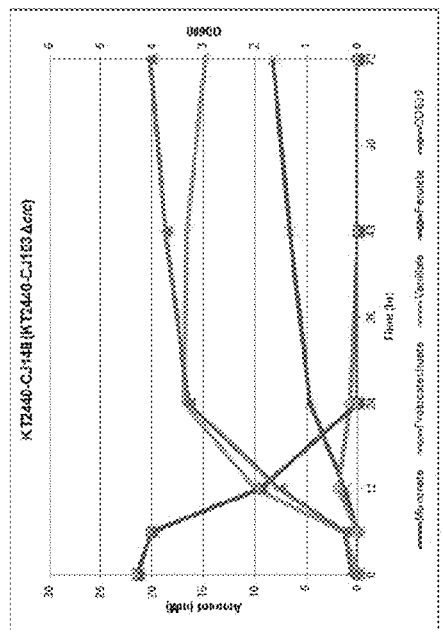
Figure 9D:
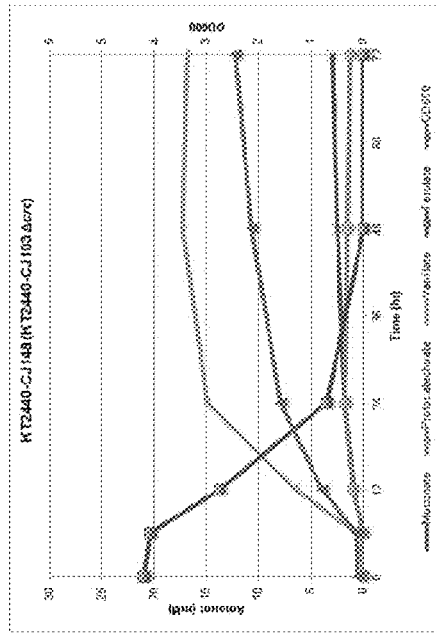
Figure 9F:
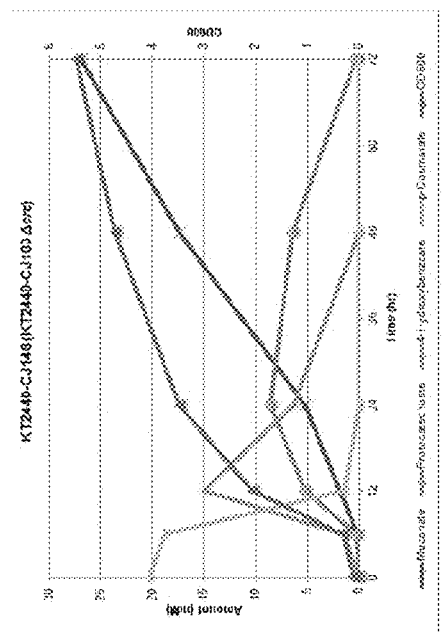
Figure 9H:
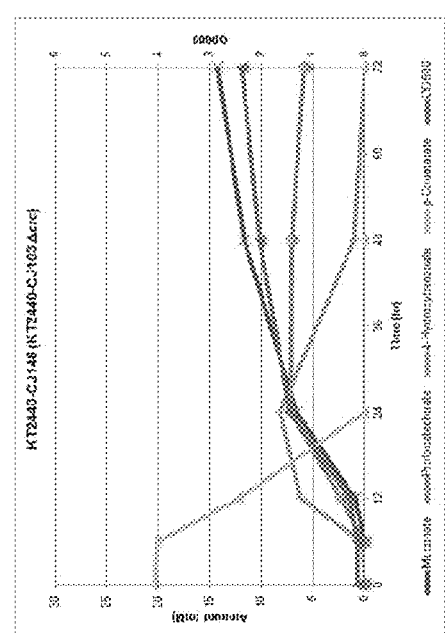

In addition to the AroY "bottleneck" described above, a considerable accumulation of vanillate was observed in the *P. putida* KT1440-CJ103 when metabolites from the coniferyl alcohol degradation pathway including coniferyl alcohol, ferulate, and vanillin were used as substrates for the production of muconic acid. This resulted in a reduction in the amount of muconic acid produced. FIGS. 8*b-d* illustrate the performance results of strains successfully engineered to remove this bottleneck, as demonstrated by reduced accumulation of vanillate and, thus, increased production of muconic acid relative to the empty vector control strain (FIG. 8*a*). A *P. putida* strain with increased expression of VanA is shown in FIG. 8*b*, a *P. putida* strain with increased expression of VanB is shown in FIG. 8*c*), and a third *P. putida* strain with increased expression of both VanA and VanB is shown in FIG. 8*d*. Unlike, the strains described above which involve genomic gene additions, VanA and VanB were added to the *P. putida* KT1440 strain by cloning the genes that encode these proteins into a broad-host range plasmid, pBTL-2, and transforming the resulting plasmids into *P. putida* KT2440-CJ102, where expression of these genes were driven constitutively by the Plac promoter in pBTL-2.

Example 3

Deregulation of Carbon Catabolite Repression to enhance aromatic catabolism and, subsequently, increase production of muconic acid from aromatic molecules.

In Pseudomonads such as *P. putida* KT2440, the Catabolite Repression Control (Crc) protein binds targeted RNAs encoding proteins involved in catabolism and, thereby, may inhibit their translation and, thus, their activity. Pathways that enable catabolism of less preferred substrates are inhibited by Crc until preferred substrates, those which provide more carbon and/or energy, have been depleted. Among the targets of Crc regulation is catabolism of aromatic molecules. As shown in FIGS. 9*a-h*, deletion of Crc from *P. putida* KT2440-CJ102, resulted in less accumulation of intermediates from aromatic degradation, including 4-hydroxybenzoate and vanillate, which in turn resulted in higher production of muconic acid (see FIGS. 9*b*, 9*d*, 9*f*, and 9*h*), relative to the equivalent strain expressing Crc (see FIGS. 9*a*, 9*c*, 9*e*, and 9*g*). Thus, deletion of Crc represents a novel way to enhance the catabolism of aromatic molecules derived from lignin depolymerization and the subsequent production of molecules derived from them, such as muconic acid.

Example 4

Expression of 3 dehydroshikimate dehydratase, AsbF, and the protocatechuate decarboxylase, AroY, for production of muconic acid from sugars.

Figure 10B:
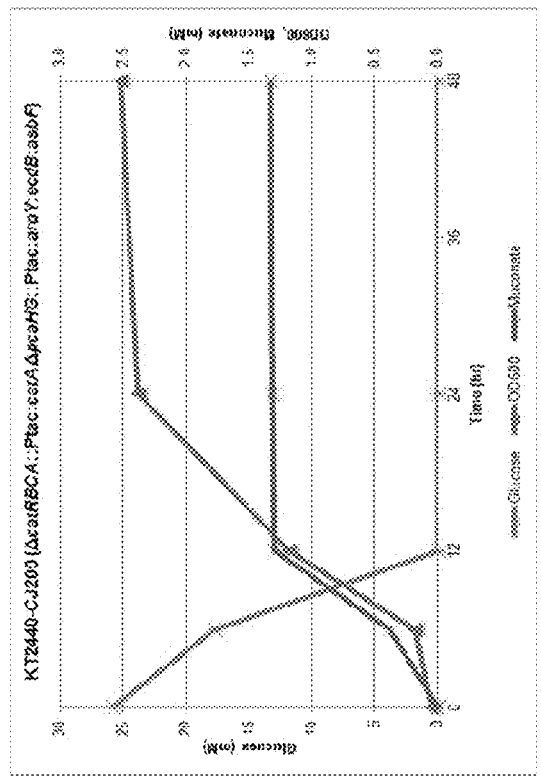
FIGS. 10a-b summarize experimental results obtained from an engineered strain of P. putida modified to express 3 dehydroshikimate dehydratase, AsbF, the protocatechuate decarboxylase, AroY, and the protocatechuate subunit, EcdB, for enhanced production of muconic acid from sugars, according to exemplary embodiments of the present invention.
Figure 10A:
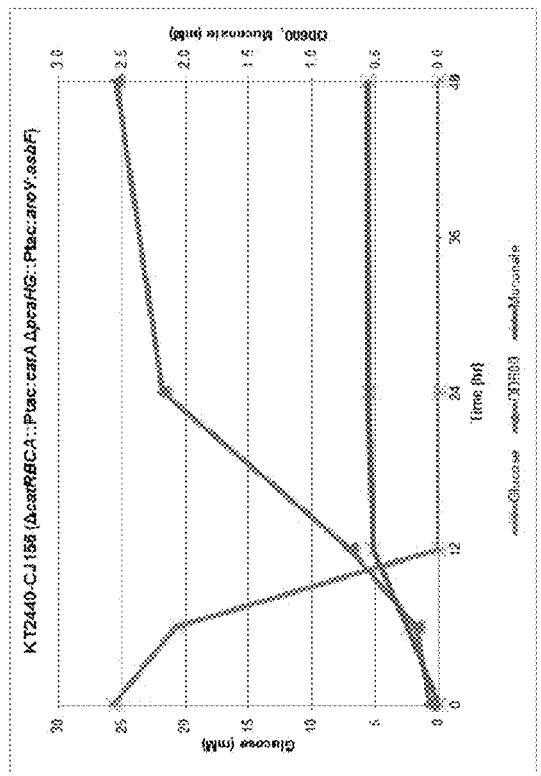

Heterologous expression of a 3 dehydroshikimate (3-DHS) dehydratase, a protocatechuate decarboxylase, and a catechol dioxygenase may convert 3-DHS, an intermediate in the biosynthesis of aromatic amino acids, to protocatechuate, which may then be converted to catechol and cleaved to form muconic acid. FIGS. 10*a-b* demonstrate the production of muconic acid from glucose (FIG. 10*a*) by the engineered *P. putida* strain KT2440-CJ156 and KT2440-CJ200.

Referring to FIG. 10*a*, two genetic modifications were made to *P. putida* strain KT2440 to produce new *P. putida* strain KT2440-CJ156. First, the catRBCA genes were deleted and replaced by a DNA fragment comprising the Ptac promoter upstream of catA and second, the pcaHG genes were deleted and replaced with a DNA fragment comprising the Ptac promoter upstream of aroY from *Enterobacter cloacae* subsp. *cloacae* (ATCC 13047) and asbF from *Bacillus cereus* (ATCC 14579). Referring to FIG. 10*b*, two genetic modifications were made to *P. putida* strain KT2440 to produce new *P. putida* strain KT2440-CJ200. First, the catRBCA genes were deleted and replaced with a DNA fragment comprising the Ptac promoter upstream of catA and second, the pcaHG genes were deleted and replaced with a DNA fragment comprising the Ptac promoter upstream of aroY from *Enterobacter cloacae* subsp. *cloacae* (ATCC 13047), ecdB from *Enterobacter cloacae* subsp. *cloacae* (ATCC 13047), and asbF from *Bacillus cereus* (ATCC 14579). Such engineered *P. putida* KT2440 strains have several advantages over less stress-tolerant, plasmid-bearing hosts such as *E. coli* or *Saccharomyces cerevisiae*. In addition, expression of ecdB more than doubled the amount of muconic acid produced from glucose (see FIG. 10*b*), by increasing the activity of AroY. This pathway may be used to produce muconic acid from cellulose or hemicellulose-derived sugars such as glucose or xylose (or, for example, arabinose, mannose, galactose or rhamnose) as well as other bio-mass relevant feedstocks including, but not limited to acetate, and glycerol.

Example 5

Strains, plasmid construction, and gene replacement methods. The example presented here illustrates the methods used to genetically modify *P. putida* KT2440 to construct the various modified *P. putida* strains described above.

Competent NEB (New England Biolabs, Inc., Ipswich, Mass.) C2925 and Life Technologies (Grand Island, N.Y.) TOP10 was used for plasmid construction of cis,cis-muconate (muconic acid) producing and phenol utilizing strains, respectively. NEB 5-alpha F'I$^q$ *E. coli* was used for all remaining plasmid constructions and were grown shaking at 225 rpm, 37° C., in LB Broth (Lennox) containing 10 g/L tryptone, 5 g/L yeast extract, 5 g/L NaCl or on LB plates containing 15 g/L agar, with either 10 µg/mL tetracycline or 50 µg/mL kanamycin. *E. coli* was transformed according to the manufacturer's instructions.

Q5® Hot Start High-Fidelity 2× Master Mix (NEB) and primers synthesized by IDT (Integrated DNA Technologies, Inc., Iowa) were used in all PCR amplification for plasmid construction. Primer sequences are shown in FIG. 11. Plasmids were assembled using Gibson Assembly® Master Mix (NEB) according to the manufacturer's instructions. The sequences of all plasmid inserts were confirmed using Sanger sequencing Plasmids for gene replacement were constructed in pCM433 (Addgene Inc., Cambridge, Mass.)1 or pK18mobsacB from ATCC (American Type Culture Collection, Manassas, Va.), both of which are unable to replicate in *P. putida* and contain antibiotic resistance genes to select for integration of the plasmid into the genome by homologous recombination and sacB to counterselect for recombination of the plasmid out of the genome. Plasmids for expression of vanA and/or vanB were constructed in pBTL-2 (Addgene Inc., Cambridge, Mass.), which is able to replicate in *P. putida.*

The pCM433-based integration vector used to replace catRBCA with Ptac:catA (pMFL22) was constructed by Gibson assembly of three PCR products: LP29 and LP33 were used to amplify the targeting region upstream from catA, LP30 and LP31 were used to amplify the Ptac promoter from Sigma pFLAG-CTC, LP32 and LP34 were used to amplify the entire coding region of catA including its native RBS. After assembly, the 2.2 kb fragment was amplified by PCR using primers LP29 and LP34, and cloned into the pCM433 vector using NotI sites.

The pK18mobsacB-based plasmid for integration of the phenol monooxygenase genes (pMFL56) was constructed by Gibson assembly of three PCR fragments using primers LP53 and LP48 to amplify the catA targeting region, LP49 and LP50 for amplification of six phenol monooxygenase genes, dmpKLMNOP using pVI1261 as the template (provided by Dr. Victoria Shingler from the Department of Molecular Biology at timed University), and primers LP51 and LP54 for amplification of the targeting region downstream from catA. Fragments were then cloned into pK18-mob vector using NotI sites.

In the plasmid for replacement of pcaHG with Ptac:aroY (pCJ023), the aroY gene (ADF69416) from *Enterobacter cloacae* ATCC13047 was optimized for expression in *P. putida* KT2440 using DNA 2.0's Gene Designer software and synthesized in two overlapping DNA fragments by IDT. The first fragment also contained the Ptac promoter, which was separated from the initiating ATG by a ribosome binding site with the sequence AGAGGAGGGAGA. These fragments were then assembled by Gibson assembly and Ptac:aroY was amplified from this assembly with primers oCJ165 and oCJ166. Approximately 1 kb regions upstream and downstream of pcaHG were amplified using oCJ100/oCJ101, and oCJ102/oCJ103, respectively. The upstream targeting region, Ptac:aroY, and the downstream targeting region were then assembled into pCM433 linearized with restriction enzymes AatII and SacI (NEB).

Gene replacement plasmids were transformed into *P. putida* strains by electroporation. LB broth was inoculated to an OD600 of about 0.02 and incubated shaking at 225 rpm, 30° C., until an OD600 of 0.5-0.7 was reached. Cells were then centrifuged at 4° C., washed twice in ice-cold water and once in ice-cold 10% glycerol or 3 mM potassium phosphate (KPi), pH 7.0, before being resuspended in 1/100 of the culture's original volume of 10% glycerol (or 3 mM KPi). Cells were then stored at −80° C. or transformed by electroporation immediately. For transformation, 5 μL (200 ng-2 μg) of plasmid DNA was added to 50 μL of the electrocompetent cells, transferred to a chilled 0.1-cm electroporation cuvette, and electroporated at 1.6 kV, 25 uF, 200 ohms. 450 μL SOC outgrowth medium (NEB) was added to the cells immediately after electroporation and the resuspended cells were incubated shaking at 225 rpm, 30° C., for one hour. The entire transformation was plated on LB agar plates containing appropriate antibiotics (30 μg/mL tetracycline for pCM433-based plasmids, 50 μg/mL kanamycin for pK18mobsacB-based plasmids) and incubated at 30° C. overnight. Transformants were restreaked for single colonies on LB agar and incubated at 30° C. overnight to reduce the possibility of untransformed cells being transferred. For sucrose counter-selection, restreaked transformants were streaked for single colonies on YT+20 or 25% sucrose plates (10 g/L yeast extract, 20 g/L tryptone, 250 g/L sucrose, 18 g/L agar) and incubated at 30° C. overnight. *P. putida* KT2440 containing the sacB gene can grow, although very slowly, on YT+20% or 25% sucrose media. Therefore, colonies presumed to have recombined the sacB gene out of the genome—those colonies that were larger than most—were restreaked on YT+25% sucrose plates and incubated at 30° C. overnight to reduce the possibility that cells that had not recombined would be carried along with sucrose resistant isolates. Colonies from the second YT+25% sucrose plates were subjected to colony PCR to check for gene replacement at both junctions. These isolates were also plated on LB plates containing appropriate antibiotics to ensure that they had lost antibiotic resistance and, thus, represented pure gene replacements.

Figure 12A:
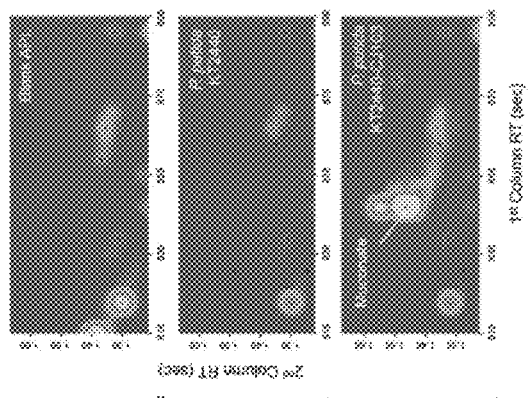
FIGS. 12a-c show experimental results comparing muconic acid production of a genetically engineered strain to the starting strain, according to exemplary embodiments of the present invention.
Figure 12B:
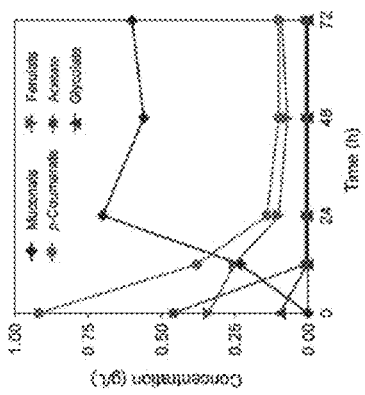
Figure 12C:
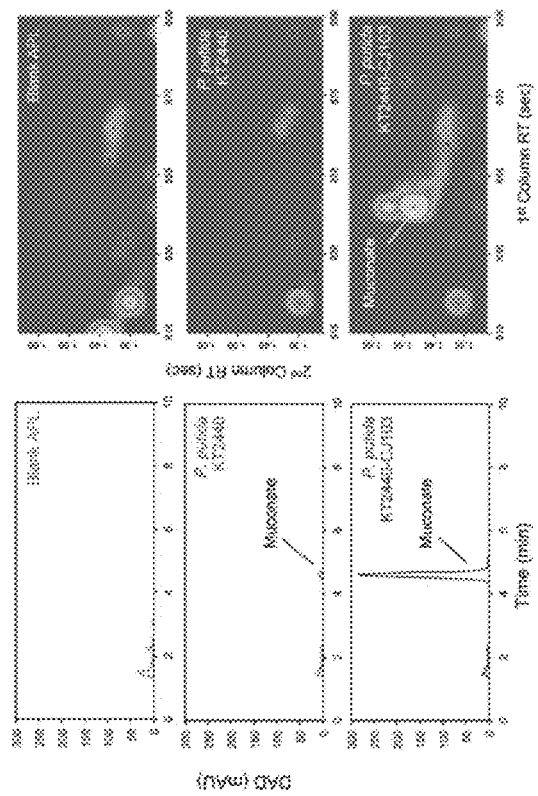

Referring to FIGS. 12*a-c*, these figures provide experimental data obtained from "proof of concept" tests to show the viability of utilizing engineered microorganisms to metabolize lignin-derived raw materials to produce muconic acid. In this example, alkaline pretreatment with NaOH and anthraquinone (AQ) was applied to corn stover at 70 mg NaOH/g dry biomass with an AQ concentration of 0.2 wt % of dry stover. The resulting alkaline pretreated liquor (APL) stream contains a substantial amount of lignin-derived aromatics such as p-coumarate and ferulate as well as acetate, biomass extractives, and very minor concentrations of sugars (<0.5 g/L of any monomeric sugar). The pH of APL was reduced to about 7 with the addition of $H_2SO_4$. The liquor was then filtered through a 0.2 μm filter for sterilization and to remove residual solids.

Flasks containing 25 mL of M9 minimal medium supplemented with 0.9×APL were inoculated with *P. putida* KT2440 or KT2440-CJ103 and cultured for three days. Following biological conversion, cells were removed by centrifugation and activated carbon (12.5 wt/vol %) was added to the remaining culture media to remove non-target aromatics and facilitate analysis by HPLC. Analysis by HPLC detected significant levels of muconic acid in cultures grown with *P. putida* KT2440-CJ103, while no significant quantities were detected in the blank APL control sample or with the native *P. putida* KT2440 (see FIG. 12*a*). Likewise, analysis of derivatized acids in unpurified culture samples by GCxGC-TOFMS (time-of-flight mass spectrometry) confirmed the identity of muconic acid and displayed comparable trends in concentration, as shown in of FIG. 12*b*.

To track the conversion of primary aromatic and nonaromatic components in APL during shake flask cultivation, GCxGC-TOFMS was also employed. Analysis of APL determined that p-coumarate and ferulate were initially present at significant levels (0.92 g/L and 0.34 g/L, respectively), in addition to the short chain acids glycolate and acetate (0.46 g/L and 0.10 g/L, respectively), as shown in FIG. 12*c*. Other aromatic acids, including benzoate, caffeate, vanillate, and 4-hydroxybenzoate, were not detected in significant levels (>0.01 g/L). During shake flask cultivations, *P. putida* KT2440-CJ103 rapidly consumed glycolate and acetate, which can be used as sources of carbon and energy for growth. The primary aromatic components, p-coumarate and ferulate, were converted to 0.70 g/L of muconate after 24 hours (see FIG. 12*c*). Based on the consumption of these two major aromatic acids, the molar yield to muconate was 67%.

Example 5: Strains, Media, and Growth Conditions

*P. putida* KT2440 (ATCC 47054) and its derivatives were grown shaking at 225 rpm, 30° C., in LB Broth or LB plates. During gene replacement, sucrose selection was performed on YT+25% sucrose plates (10 g/L yeast extract, 20 g/L tryptone, 250 g/L sucrose, 18 g/L agar). Shake flask and bioreactor experiments were performed using modified M9 minimal media containing 13.56 g/L disodium phosphate, 6 g/L monopotassium phosphate, 1 g/L NaCl, 2 g/L NH4Cl, 2 mM Mg504, 100 mM CaCl2, and 18 mM Fe504.

Example 6: Shake Flask Experiments with Model Monomers and APL

Fed batch and shake flask experiments were performed using 125 mL baffled flasks containing 25 mL modified M9 media supplemented with 10 mM sodium benzoate, coniferyl alcohol, ferulate, vanillin, caffeate, p-coumarate, 4-hydroxybenzoate or 5 mM phenol and 20 mMsodium acetate or 10 mMglucose. For shake flask experiments in which cells were grown on alkaline pretreated liquor (APL), modified M9 medium was supplemented with APL at a concentration of 0.9×. Cultures were inoculated with cells washed in modified M9 medium to $OD_{600}$ 0.05, then incubated shaking at 30° C., 225 rpm. Every 12 hours cultures were sampled for HPLC, $OD_{600}$, and pH measurement. For cultures at pH>7.4 or <6.6, the pH was adjusted to 7.0 by adding 1 N HCl or 1 N NaOH. 20 mM sodium acetate or 10 mM glucose was added before returning the cultures to the incubator.

Example 7: Fed-Batch Cultivation

A seed batch culture of *P. putida* KT2440-CJ103 was started in a shake flask and grown overnight in LB, 30° C., 225 rpm. The next morning, cells were centrifuged 3800× g, 10 minutes and washed once with modified M9 medium containing 10 mM glucose. Cultures were transferred to 700 mLs of the same medium in a 2 L Applikon (Applikon Biotechnology, Inc.) EZ Control 2 L bioreactor, starting at an initial $OD_{600}$ of 0.2. Base pH was controlled by 2 N NaOH to pH 7. The temperature was maintained at 30° C. Mixed air was used to deliver oxygen at a flow rate of 2 L/min. DO saturation was manually adjusted to ~50% by varying stirrer speed, from 250 to 650 rpm, and then maintained at 650 rpm for the duration of the experiment. At 5 hours, 2 mM p-coumarate was added. When glucose was consumed at ~11.5 h, a large spike in DO was observed, indicating that glucose was depleted and confirmed by YSI analysis. A separate pump was computer programmed to deliver for 30 seconds (~2.4 mL) a p-coumarate:glucose:ammonium sulfate (68.4:36.5:9 g/L) feed when DOT (dissolved oxygen tension) levels reached ≥75%. The feed caused a temporary drop in DOT to ~50%, until glucose concentrations fell again. As expected, DOT oscillations proceeded at similar frequencies, until the p-coumarate:glucose:ammonium sulfate feed was terminated at 75.5 hours and the bioreactor was shut down at 78.5 hours.

Muconic Acid Separation, Purification, and Upgrading

Referring again to FIGS. 1a-c, microbial catalysis operations 140 are only one part of a fully-integrated biorefinery 100. Once a production-scale culture has successfully produced muconic acid, several processing steps remain to obtain a purified muconic acid stream and/or final product(s) that may be manufactured from muconic acid; e.g. adipic acid, nylon-6,6. As discussed previously, one or more separation operations 150 may be required to generate a purified and usable muconic acid stream.

Separation/purification operations 140 are needed to generate a usable muconic acid stream for a number of reasons. For example, a wide variety of impurities may be introduced during the biological production of muconic acid, similar to the challenges faced with other target bio-derived molecules (e.g., ethanol, succinic acid, lactic acid). These impurities may include fermentation salts, nutrients and media to support growth, unconverted substrate, extracellular proteins and lysed cell contents, as well as the buildup of non-target metabolites. Accumulation of these constituents in culture broth may vary greatly depending on the microorganism, substrate used for conversion, biological growth conditions and bioreactor design, and broth pretreatment. Likewise, utilization of monomer streams derived from complex lignocellulosic biomass may vary greatly depending on the biomass fraction of interest (e.g., cellulose, hemicellulose, lignin), choice of feedstock (e.g., herbaceous, hardwoods, softwoods), and depolymerization technology.

Figure 13:
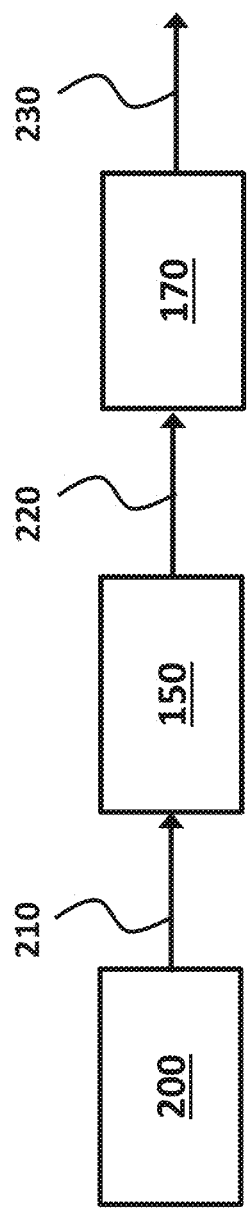
FIG. 13 illustrates post-biocatalysis steps to produce purified muconic acid and subsequently final produces, according to exemplary embodiments of the present invention.

Therefore, a culture broth containing a target muconic acid titer will need to be processed before any final products may be manufactured. So, referring to FIG. 13, a muconic-acid containing culture broth 210 may be fed from a bioreactor 200 to a separation/purification operation 150 to produce a purified muconic acid stream of sufficient quality that it may then subsequently be fed to an upgrading 170 section of the biorefinery. Upgrading may include, for example, catalytic hydrogenation of the purified muconic acid to produce adipic acid. The adipic acid may then be further reacted to produce nylon-6,6. In some embodiments of the present invention, the process for producing muconic acid from biomass may further comprise at least one initial separation step that produces the at least one biomass feed stream, wherein the separation step comprises receiving a biomass raw material comprising at least two substituents comprising at least two of lignin, cellulose, hemicellulose, or mixtures thereof, and separating at least two of the substituents to produce the at least one biomass feed stream. In some embodiments of the present invention, the separation separates lignin from polysaccharides to produce a first biomass feed stream comprising lignin, and a second biomass feed stream comprising polysaccharides. The polysaccharide stream may comprise at least one of cellulose, hemicellulose, and mixtures thereof.

Some exemplary technologies that may be utilized in the separation/purification operation 150 include at least one of affinity chromatography, ion exchange chromatography, solvent extraction, liquid-liquid extraction, distillation, filtration, centrifugation, electrophoresis, hydrophobic interaction chromatography, gel filtration chromatography, reverse phase chromatography, chromatofocusing, differential solubilization, preparative disc-gel electrophoresis, isoelectric focusing, HPLC, and/or reversed-phase HPLC.

Figure 14:
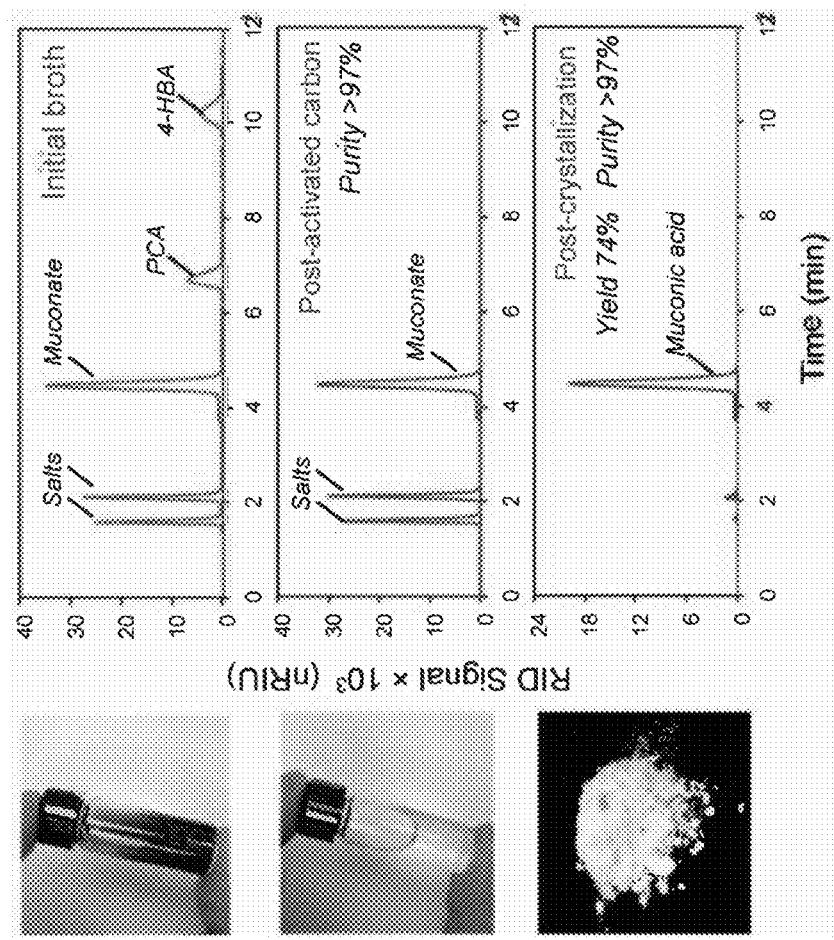
FIG. 14 illustrates experimental results quantifying the components present in a culture broth before treatment with activated carbon, after treatment with activated carbon, and after crystallization, according to exemplary embodiments of the present invention.

Cell removal from the broth may be achieved by a variety of solid removal unit operations. Some examples include filtration, centrifugation, and combinations thereof. Once the microorganism cell matter has been removed, further impurity removal operations may be utilized. For example, the biological ring opening of muconate allows for *facile* purification from culture media containing non-target aromatic metabolites (e.g., unreacted protocatechuic acid and 4-hydroxybenzoic acid) using activated carbon due to the high adsorption affinity of oxygenated aromatics in comparison to aliphatic acids. FIG. 14 illustrates a comparison of an initial broth (from FIG. 5) and the same broth after treatment with activated carbon. In this example, activated carbon was added to the culture media at about 12.5% (wt/vol) and the resultant mixture was stirred for about 1 hour. This treatment step resulted in nearly complete removal (below detectable limit by HPLC) of protocatechuic acid and 4-hydroxybenzoic acid, while the majority of the muconic acid (89% of initial culture media concentration, mass/vol) remained in solution.

The activated-carbon-treated muconic acid was then crystallized by reducing the pH and temperature, which is enabled due to the strong pH and temperature dependence of dicarboxylic acids. At a pH of about 2 and temperature of about 5° C., muconic acid readily precipitated from solution and the muconic acid crystals were recovered by vacuum filtration. This method recovered 74% of the muconic acid initially present in the activated-carbon-treated muconic acid stream, with a high degree of purity (>97%), as shown in the bottom plot of FIG. 14.

The activated carbon treatment of cell-free, muconic acid containing broth was tested a second time, this time on the broth resulting from culture shown in FIG. 6. The separation process initially consisted of activated carbon purification to remove soluble organic broth impurities and pH/temperature shift crystallization to precipitate muconic acid from purified broth solution and recover solid crystals for drying, similar to what was described above. However, in this example, an additional step, ethanol dissolution and microfiltration was utilized to remove bulk inorganic salts. Purity results for separation tests completed on muconic acid generated by biocatalysis compared to commercial grade muconic acid are summarized in the table below.

TABLE 1

Purity of commercial muconic acid (chemical origin) and biologically derived muconic acid after sequential treatment.

| Sample Origin | AC Treated | pH 2 Crystallized | EtOH Dissolved | Purity (%) |
|---|---|---|---|---|
| Commercial Chemical | N | N | N | 97.83 ± 0.07% |
| Biological Conversion | Y | Y | N | 97.86 ± 0.05% |
| Biological Conversion | Y | Y | Y | 99.76 ± 0.04% |

[a]Standard deviation values reported for triplicate sample measurements.

An activated carbon loading of about 2 wt/vol % was needed to remove residual benzoate from this culture broth to below detectable limits (as determined by high performance liquid chromatography diode array detection. Color compounds in the broth were also removed to a significant extent, turning the broth from a coffee-colored appearance to semi-clear; however, non-selective adsorption of resulted in a 16% reduction in muconic acid broth concentration (6.86 g/L).

Figure 15:
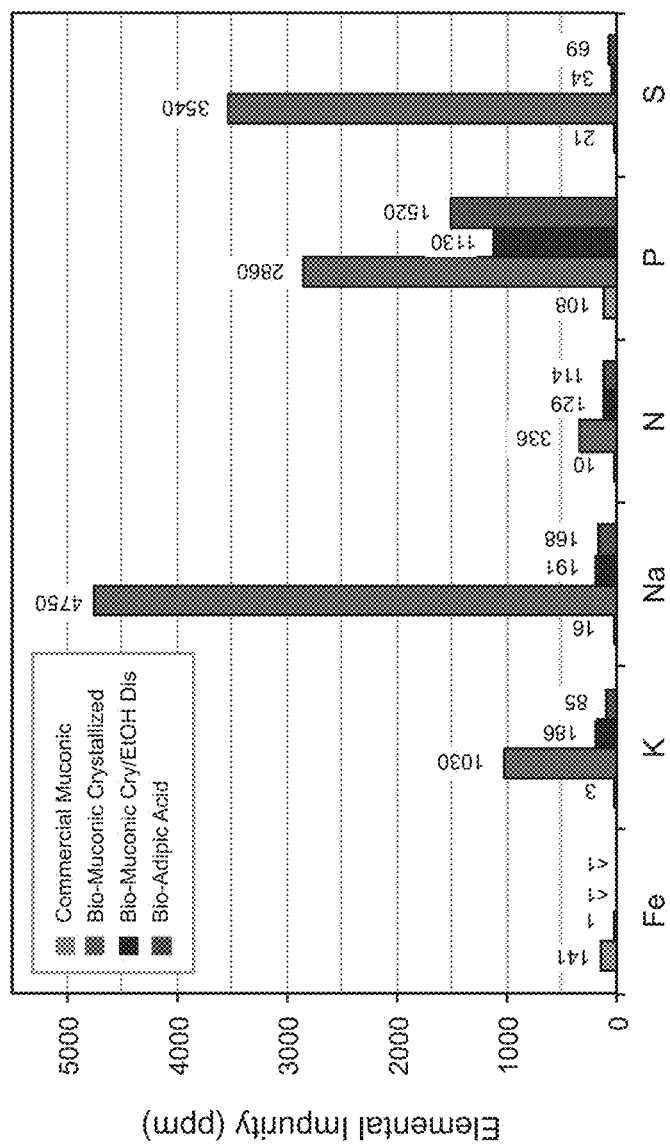
FIG. 15 compares the elemental content of commercially available muconic acid biocatalysis-derived muconic acid at various purification/separation steps, according to exemplary embodiments of the present invention.

Following the activated carbon treatment, muconic acid was precipitated from the broth by pH/temperature shift crystallization. By adjusting the broth pH to 2 with sulfuric acid and reducing the temperature to 5° C., muconic acid readily precipitated. Precipitated muconic acid crystals were then vacuum filtered (0.2-μm PES) and dried in a vacuum oven for about 48 hours. Purity analysis by differential scanning calorimetry (DSC) melting point analysis determined the muconic acid crystals were about 97.83±0.05% pure at this stage. Combustion analysis of muconic acid crystals at 700° C. measured a sample ash content of 1.44% (wt/wt), and elemental analysis by ICP-MS and nitrogen chemiluminescence identified major impurities as sodium (4750 ppm), sulfur (3540 ppm), phosphorus (2860 ppm), potassium (1030 ppm), and nitrogen (336 ppm), as shown in FIG. 15. As shown in FIG. 15, the elemental impurities identified in biologically derived muconic acid differed significantly compared to the impurities observed in chemically derived muconic acid obtained from Sigma Aldrich, with the latter being much lower in sodium, sulfur, phosphorous, potassium, and nitrogen, but higher in iron and chloride. The major inorganic impurities identified in the bio-derived muconic acid are known poisons to platinum group metals, requiring removal strategies prior to catalysis. Likewise, polymer-grade adipic acid requires trace levels of iron (<0.2 ppm) and nitrogen (<20 ppm N), necessitating further treatment.

Figures 16A, 16B, 16C, 16D, 16E, 16F:
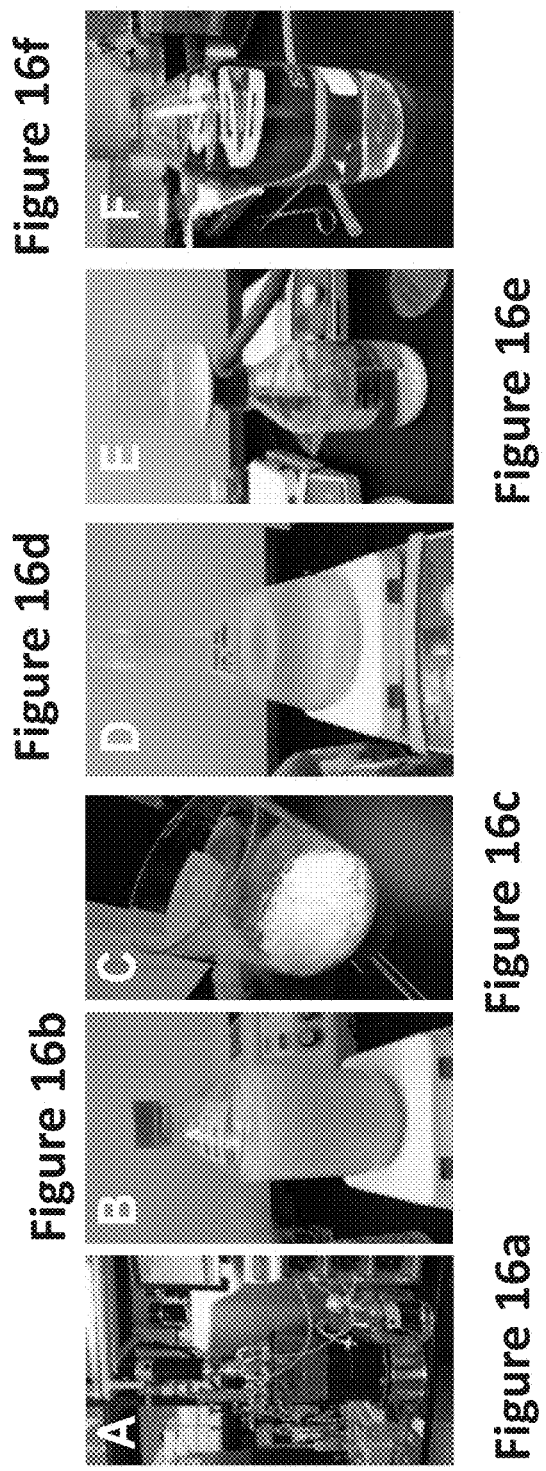
FIGS. 16a-f illustrate purification of muconic acid biological culture media by activated carbon treatment, pH/temperature shift crystallization, and ethanol dissolution with microfiltration, according to exemplary embodiments of the present invention.

In order to reduce the level of inorganic impurities in the bio-derived muconic acid and generate a feed stream with sufficient purity and quality to enable successful downstream upgrading, the muconic acid crystals produced in the previous steps were dissolved in ethanol and filtered through a 0.2-μm PES membrane. Upon ethanol dissolution, the muconic acid-ethanol solution was initially cloudy due to insoluble salts, whereas after filtration the solution was very clear (see FIGS. 16a-f). The initial muconic acid culture broth appeared dark coffee colored (FIG. 16a). Activated carbon treatment of the broth significantly removed color compounds, while adjustment to a pH of about 2 initiated crystal formation (FIG. 16b). Filtration and drying of the purified broth produced a white crystal solid, with a purity of 97.86±0.05% by DSC melting point analysis (FIG. 16c). Muconic acid crystals dissolved in ethanol resulted in a cloudy solution (FIG. 16d), that upon 0.2-μm microfiltration (FIG. 16e) resulted in a clear solution (FIG. 16f) with a final muconic acid purity of 99.76±0.04% upon drying. Analysis of filtered and dried muconic acid after ethanol dissolution revealed an overall DSC-purity of 99.76±0.04% as shown in Table 1 above, with a significant reduction in elemental impurities.

Analysis by ICP-MS determined that sodium was reduced by 96%, sulfur by 99%, phosphorous by 60%, potassium by 82%, and nitrogen by 62% (see FIG. 14), consistent with reductions in low-concentration elements (<100 ppm aluminum, chlorine, magnesium) (results not shown). Biocatalysis-derived muconic acid iron levels were much lower (<1 ppm) compared to muconic acid of chemical origin (141 ppm). Nitrogen levels in bio-muconic acid were still above the polymer precursor specification of 20 ppm, due to residual fermentation proteins that were not removed during activated carbon treatment and microfiltration.

Referring again to FIG. 13, the details provided above demonstrate that biomass-derived muconic acid can be successfully produced by genetically engineered microorganism modified to funnel both lignin depolymerization products and polysaccharide depolymerization products to muconic acid with high yield and selectivity in a bioreactor 200. The muconic acid containing broth 210 can then be successfully treated in a separation/purification operation 150 to produce a purified muconic acid stream 220. This purified muconic acid stream 220 can then be used in an upgrading operation 170 to produce value-added final products, including fuels and commodity chemicals.

Figure 17A:
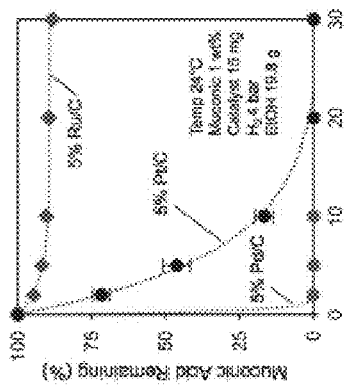
FIGS. 17a-d summarize data from experiments evaluation catalytic hydrogenation of muconic acid to adipic acid, according to exemplary embodiments of the present invention.
Figure 17B:
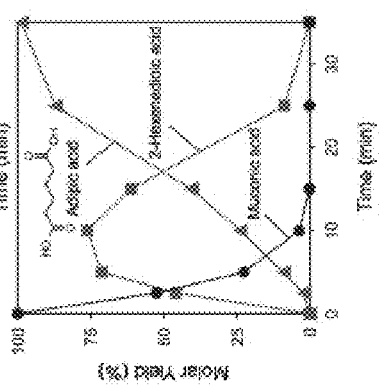
Figure 18:
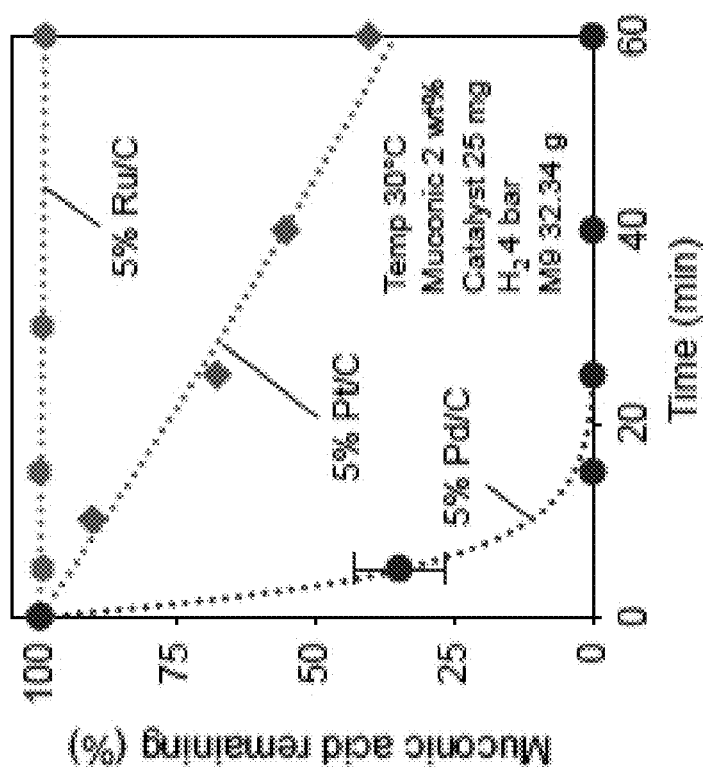
FIG. 18 illustrates experimental data obtained screening catalysts for hydrogenating muconic acid to adipic acid using noble metal catalysts, according to exemplary embodiments of the present invention.

As described above, a high volume intermediate that may made from muconic acid is adipic acid, which may then be further converted to nylon-6,6. To evaluate the feasibility of converting bioderived muconic acid to adipic acid, catalyst screening experiments were conducted to identify highly active materials for muconic acid hydrogenation at low temperature and pressure. Commercial noble metal catalysts supported on carbon were initially tested at 5 wt % loading, including palladium, platinum, and ruthenium. Characterization of the virgin catalyst materials (see FIG. 17a and FIG. 18) revealed the metals were dispersed as small crystallites, with comparable support surface areas (705-1075 $m^2/g$), pore volumes (0.51-0.71 mL/g), and a wider range of exposed active metal areas (22-51% dispersion). Screening experiments found that Pd/C was by the most active catalyst, with consistent activity trends when using M9 culture media (aqueous solution containing salts to support biological growth) or ethanol, as a representative protic polar organic solvent. During the course of the reaction, 2-hexenedioc acid was observed as the primary intermediate, likely due to the low temperature conditions that minimized competing non-selective reaction pathways. For reactions that went to completion with Pd, selectivity to adipic acid was >97% (mol/mol) (See FIG. 17b).

Figure 17C:
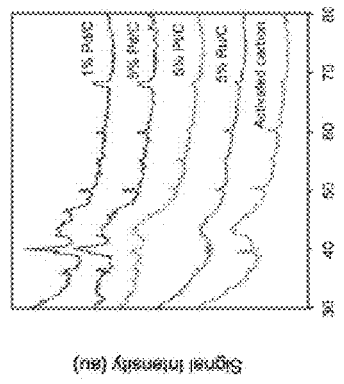
Figure 17D:
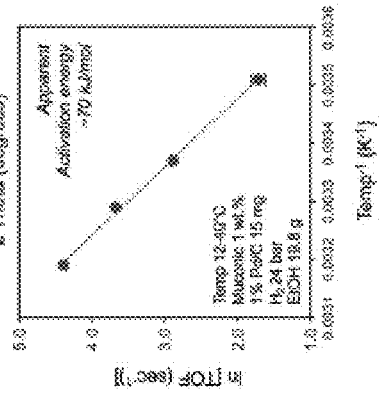

Additional hydrogenation conditions were examined with Pd/C to (i) determine its activity under surface reaction controlling conditions, (ii) evaluate the apparent activation energy for muconic acid reduction, and (iii) demonstrate its utility with muconic acid recovered from fed-batch biological conversion. Experiments conducted at two different Pd loadings (1 wt % and 2 wt % Pd/C) exhibited comparable turn over frequencies (TOF; 23±6/s and 30±6/s, respectively, at 24 bar of hydrogen and 24° C. in ethanol, 15 mg catalyst, stirring at 1600 rpm), supportive of surface reaction controlling conditions. Experiments to measure the hydrogenation rate of muconic acid at varying temperatures estimated an apparent activation energy of ~70 kJ/mol (see FIG. 17c), significantly above values indicative of mass transfer limitation (<20 kJ/mol). Hydrogenation with Pd/C was then demonstrated with muconic acid obtained from fed-batch biological conversion of p-coumarate after activated carbon purification and crystallization. Hydrogenation at room temperature progressed rapidly in a series reaction (see FIG. 17d, muconic acid TOF 25±3 sec$^{-1}$), resulting in high purity adipic acid as the final product (>97% mass/mass). After the reaction, analysis of the ethanol solvent indicated that leaching of Pd occurred to a minor extent (7 mg/L, 0.8% of the loaded metal), which may occur due to the acidic liquid phase conditions employed.

Additional studies were completed to evaluate the hydrogenation of bioderived muconic acid to adipic acid. Batch reactor catalyst screening experiments were conducted with platinum group metals to evaluate their activity and stability against leaching during muconic acid hydrogenation. Catalysts were synthesized using powdered Darco activated carbon (AC) and Davisil silica supports sieved to >270 mesh (<53 μm) to minimize the impact of mass transfer during batch conditions. Metals precursors were loaded onto their respective supports, and catalysts were reduced in hydrogen prior to characterization to determine their metal loading and dispersion, support surface area, pore volume and pore diameter, and x-ray diffraction (XRD) spectra, as shown in Table 2 and FIGS. 19a-j.

TABLE 2

Properties of virgin activated carbon (AC) and silica powdered catalysts used in batch screening reactions for muconic acid hydrogenation.

| Catalyst (nominal) | $S_{BET}$ (m$^2$ g$^{-1}$) | Pore vol.$^a$ (cm$^3$ g$^{-1}$) | Pore dia.$^a$ (Å) | Dispersion$^b$ (%) |
|---|---|---|---|---|
| 1% Pd/AC | 768 | 0.514 | 9.71 | 13 |
| 1% Rh/AC | 971 | 0.708 | 9.83 | 69 |
| 5% Ru/AC | 590 | 0.588 | 9.69 | 10 |
| 5% Pt/AC | 882 | 0.657 | 9.71 | 60 |
| 1% Pd/SiO$_2$ | 466 | 0.774 | 9.74 | 28 |
| 1% Rh/SiO$_2$ | 480 | 0.804 | 9.81 | 62 |
| 5% Ru/SiO$_2$ | 428 | 0.686 | 9.75 | 17 |
| 5% Pt/SiO$_2$ | 454 | 0.811 | 9.79 | 47 |

High surface areas were observed for both AC (590-971 m$^2$ g$^{-1}$) and silica (428-480 m$^2$/g) supported catalysts, with higher metal loading materials generally showing lower surface areas. Support pore volumes (AC 0.514-0.708 cm$^3$/g, silica 0.686-0.811 cm$^3$/g) and pore diameters (AC 9.69-9.83 Å, silica 9.74-9.81 Å) were also comparable. Elemental analysis determined metal loadings were near their nominal values and XRD analysis confirmed the absence of sharp prominent peaks due to large metal crystallites. Chemisorption analysis measured dispersions were within the range of 10-62%, likely due to differing metal precursor and support material interactions during synthesis. Due to varying active metal crystallite surface areas, observed catalyst activities for muconic acid hydrogenation were normalized to dispersion values to allow for turn-over-frequency (TOF) comparisons between metals (e.g., moles of compound reacted per second, divided by the moles of surface metal atoms measured by dispersion).

Figures 20A, 20B:
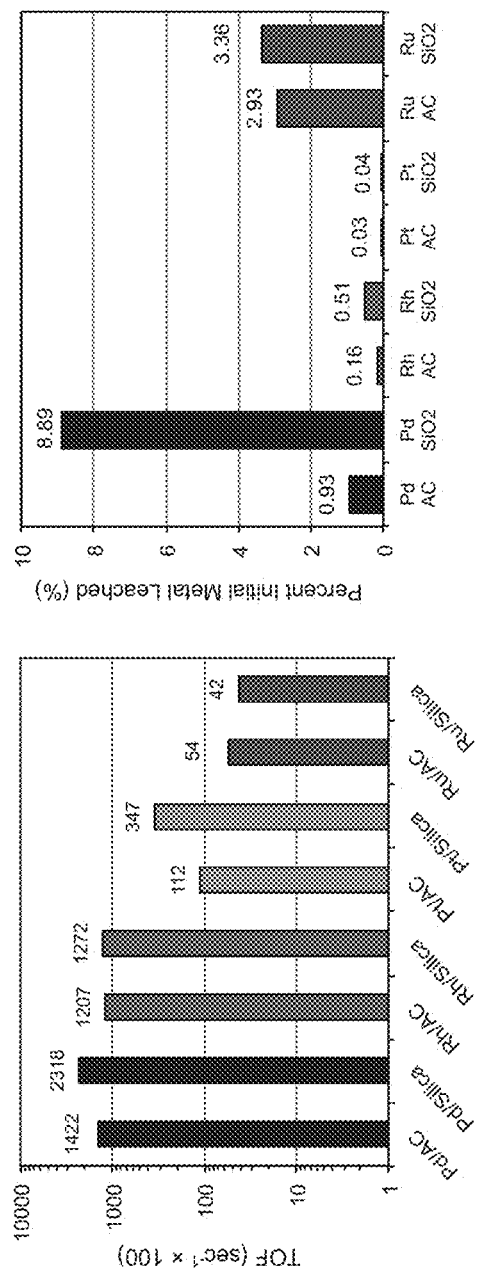
FIGS. 20a-b illustrate muconic acid hydrogenation activity for platinum group metals (PGM) on powder activated carbon and silica supports in batch (a), and PGM leaching after 35 min exposure to reaction conditions (b), according to exemplary embodiments of the present invention.

As shown in FIG. 20a, pronounced differences were observed in the muconic acid hydrogenation activity between the platinum group metals tested during batch reactor screening experiments (see FIGS. 21a-h for conversion profiles). Pd and Rh displayed highest TOF for muconic acid hydrogenation on both AC and silica supports, with Pd ranging from 14-23 sec$^{-1}$ and Rh ranging from 7-8 sec$^{-1}$. In comparison, Pt displayed a TOF ranging from 1-3 sec$^-$, while Ru ranged from 0.4-0.5 sec$^{-1}$. For batch reactions tested at room temperature, 2-hexenedioic acid was the primary intermediate observed, with trace levels of 3-hexenedioc acid identified on occasion (Scheme 1). For all catalysts screened in the batch system, mass balance closure was typically within +/−10%, with adipic acid as the only product observed upon completion of the reaction.

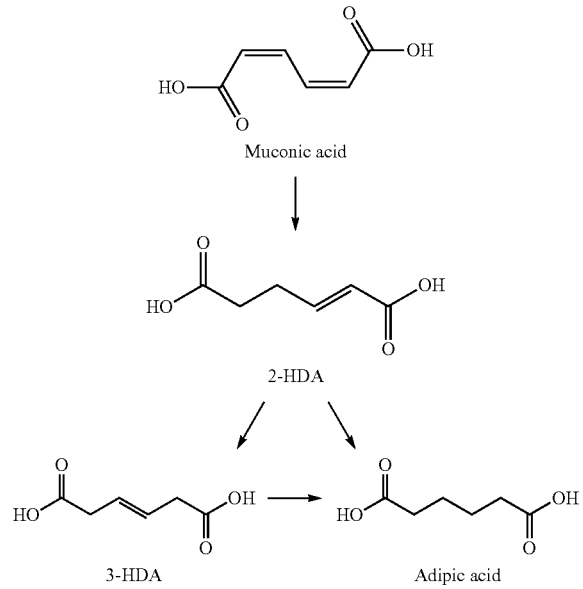

Scheme 1: Reaction network for the hydrogenation of muconic acid via the intermediate hexenedioic acid (HDA) to produce adipic acid. For room temperature batch reactions, 2-HDA was the primary intermediate, while for higher temperature (≥50° C.) 3-HDA was observed as the primary intermediate.

In addition to differing hydrogenation activity, catalyst metal leaching also varied significantly based on both the metal and choice of support, as shown in FIG. 20b. Despite exposure to reaction conditions for only 35 min, 1% Pd/SiO$_2$ displayed the greatest amount of leaching on a percent of initial metal loading basis (8.89%), while 1% Pd/AC leached to a lesser extent (0.93%). Leaching was also observed for 5% Ru/AC (2.93%) and 5% Ru/SiO$_2$ (3.36%) with muconic acid. In contrast, metal leaching for 1% Rh/AC and 1% Rh/SiO$_2$ was at trace levels, at 0.51% and 0.16%, respectively, while leaching was negligible for both 5% Pt/SiO$_2$ (0.04%) and 5% Pt/AC (0.03%). Based on the high activity for muconic acid hydrogenation and stability against leaching, Rh/AC was chosen for further time-on-stream testing in a continuous trickle-bed reactor.

Based on the activity and stability of Rh during batch reactions, continuous trickle bed reactor studies were conducted to determine its 100-h time-on-stream stability, as shown in FIG. 22. Initially, a 1% Rh/AC catalyst was prepared on Norit AC granules crushed and sieved between 100-80 mesh (150-180 μm) to minimize the catalyst bed pressure drop. The catalyst was characterized to determine its virgin and post-reaction properties, as shown in Table 3. Characterization of the virgin 1% Rh/AC catalyst showed high surface area (1029 m$^2$ g$^{-1}$), with comparable pore volume (0.455 cm$^3$ g$^{-1}$) and average pore diameter (9.69 Å) to the powder Rh/AC catalyst. XRD analysis confirmed the absence of sharp, prominent peaks due to large metal crystallites. Distinct differences were observed in XRD spectra of the powder and granule AC supports, likely due to different vendor carbon sources and/or activation techniques. The metal crystallite dispersion of the granule 1% Rh/AC catalyst was also lower (11.2%) compared to the powder catalyst.

TABLE 3

Properties of virgin and post-reaction 1% Rh/AC granule catalyst used in the 100-h time-on-stream stability test for muconic acid hydrogenation.

| Catalyst (nominal) | ICP (%) | $S_{BET}$ (m$^2$ g$^{-1}$) | Pore vol.[a] (cm$^3$ g$^{-1}$) | Pore dia.[a] (Å) | Dispersion[b] (%) |
|---|---|---|---|---|---|
| Virgin 1% Rh/AC | 0.8 | 1029 | 0.46 | 9.69 | 14% |
| Post Reaction 1% Rh/AC | 0.9 | 1130 | 0.52 | 11.43 | 21% |

[a] Pore volume and pore diameter (average) determined by BJH desorption.
[b] Dispersion calculated based on chemisorption and ICP measured metal loading.

The 100-hour time-on-stream stability test of 1% Rh/AC was then evaluated in a sequential fashion, with partial conversion of muconic acid for the first two days to confirm steady state operation, demonstration of complete conversion to adipic acid for days three and four, and lastly a return to partial conversion conditions on day five to observe any changes compared to the initial reactor performance. Sampling of the reactor was not performed during the first 12 hour overnight, since preliminary experiments showed comparable time was required to reach steady conversion once the liquid feed was introduced (see FIG. 23).

During the first 48-hours of time-on-stream (50° C., 0.5 mL min$^{-1}$ liquid flow rate), muconic acid was partially converted (57.7±1.9% average molar conversion) to hexenedioic acid (HDA) and adipic acid as the only observed products. Product identities were confirmed by gas chromatography mass spectroscopy. The moderately higher reaction temperature (50° C.) resulted in isomerization to 3-HDA as the predominant species (30.9±1.2% molar yield), in comparison to 2-HDA for room temperature batch screening reactions. Moderate amounts of 2-HDA (19.7±2.9% molar yield) and adipic acid (9.7±1.2% molar yield) were also produced, with an average molar closure of 102.7±4.9%, supporting steady state conversion during the first 48 hours. Variability in molar closure was assumed to be primarily due to solvent evaporation and error introduced during the sampling of knockout pot, with concentrations of individual species throughout the 100-h run reported in Table 4 below.

TABLE 4

Time-on-stream results for the trickle bed hydrogenation of muconic acid.[a] Compounds were monitored by HPLC-RID.

| Time (h) | Temp (° C.) | Liq. flow (mL/min) | Muconic (g/L) | 2-HDA (g/L) | 3-HDA (g/L) | Adipic (g/L) |
|---|---|---|---|---|---|---|
| 18 | 50 | 0.5 | 2.98 | 1.30 | 2.50 | 0.79 |
| 20 | 50 | 0.5 | 3.12 | 1.26 | 2.48 | 0.77 |
| 22 | 50 | 0.5 | 3.20 | 1.16 | 2.35 | 0.72 |
| 24 | 50 | 0.5 | 3.44 | 1.78 | 2.60 | 0.83 |
| 37 | 50 | 0.5 | 3.21 | 1.68 | 2.40 | 0.78 |
| 39 | 50 | 0.5 | 3.36 | 1.64 | 2.34 | 0.74 |
| 41 | 50 | 0.5 | 3.38 | 1.69 | 2.40 | 0.77 |
| 43 | 50 | 0.5 | 3.31 | 1.67 | 2.34 | 0.79 |
| 45 | 50 | 0.5 | 3.31 | 1.65 | 2.34 | 0.75 |
| 67 | 78 | 0.2 | 0.00 | 0.00 | 0.00 | 8.78 |
| 69 | 78 | 0.2 | 0.00 | 0.00 | 0.00 | 7.97 |
| 71 | 78 | 0.2 | 0.00 | 0.00 | 0.00 | 8.14 |
| 73 | 78 | 0.2 | 0.00 | 0.00 | 0.00 | 8.02 |
| 88 | 78 | 0.2 | 0.00 | 0.00 | 0.00 | 7.92 |
| 92 | 78 | 0.2 | 0.00 | 0.00 | 0.00 | 7.97 |
| 96 | 78 | 0.2 | 0.00 | 0.00 | 0.00 | 8.14 |
| 114 | 50 | 0.5 | 3.63 | 1.45 | 1.99 | 0.78 |
| 116 | 50 | 0.5 | 3.70 | 1.80 | 1.91 | 1.00 |
| 118 | 50 | 0.5 | 3.38 | 1.71 | 2.07 | 1.14 |
| 120 | 50 | 0.5 | 3.10 | 1.63 | 2.03 | 0.89 |

[a] Reaction conditions were as follows: Muconic acid 1 wt % in ethanol, liquid flow rate and temperature as indicated, H$_2$ flow 200 sccm, system pressure 24 bar, 1100 mg 1% Rh/AC granules.

Multiple factors can influence the observed reaction rates in trickle bed reactors, including the gas-liquid flow rate ratio, liquid film thickness due to shear, interparticle and intraparticle wetting, and catalyst particle size, shape, and packing geometry. Based on the liquid feed rate flow rate and conversion observed during the first 48 hours, the muconic acid hydrogenation TOF was calculated to be 0.022 sec$^{-1}$ at 50° C., which was ~1/1000$^{th}$ of the rate observed for powder Rh/AC in batch reactor screening experiments at 24° C. (TOF 7 sec$^{-1}$), indicating external and intraparticle diffusion likely influenced the observed rate due to larger particle sizes required for trickle-bed reactor experiments. Varying the catalyst bed temperature from 50-72° C. resulted in an apparent activation energy of 60.7 kJ mol$^{-1}$ for the 1% Rh/AC granule catalyst, well above typical barriers observed under solely mass transfer limiting conditions (<20 kJ mol$^{-1}$) and comparable to batch reactor results for powder 1% Pd/AC (70 kJ/mol). However, the focus was on examining alterations to the catalyst material properties after time-on-stream rather than a detailed kinetic analysis.

To demonstrate complete conversion of muconic acid to adipic acid, the temperature was increased and liquid flow rate reduced (78° C., 0.2 mL min$^{-1}$) for day three and four of operation. No peaks from HDA were observed by HPLC-DAD, which was highly sensitive to the presence of olefin bonds, supporting near complete conversion of muconic acid to adipic acid. Lastly, reaction conditions were returned to partial conversion conditions for day five to compare the catalyst conversion and selectivity to the first 48 hour of time-on-stream. Mass balance and product distribution perturbations were observed when altering the liquid flow rate, with a trend toward increasing conversion as time continued. For day five, the average muconic acid molar conversion was 55.2±3.6%, comparable to values observed during the first 48 h of time-on-stream (57.7±1.9%). Product distribution molar yields were also comparable, with average molar closure of 103.5±4.6%.

The following provides further disclosure regarding the solid catalysts describe above for the hydrogenation reaction to convert muconic acid to adipic acid. As used herein, "solid" refers to a solid material that is used as a catalyst and/or as a physical support for one or more catalytic elements. Thus, a solid may provide catalytic activity itself, may provide a structure upon which to build and physically support catalytic elements, or both. Examples of solids used in some embodiments of the present invention include, but are not limited to, carbonaceous materials, oxides, polymers, carbonates, sulfates, and clays. A non-limiting example of a carbonaceous solid is activated carbon. Examples of oxide solids include, but are not limited to, alumina, silica, titanium dioxide, and aluminosilicates. In some embodiments, a carbonaceous material or a silica-containing material may be used as a solid support and/or a solid catalyst for the catalytic conversion of muconic acid to adipic acid.

As used herein, "active site" or "active material" refers to a physical and/or chemical feature that catalyzes a reaction. A catalyst is a substance, structure, element, composition, compound, molecule, or combination thereof that accelerates a chemical reaction without itself being consumed. Examples of active sites include, but are not limited to, one or more elements in their pure form, or in mixtures to form covalently bond molecules, salts, ions, and mixtures thereof. Thus, catalytic active sites may be placed on a solid material. Such active sites may be incorporated into the solid structure itself, for example, by reaction to form covalent bonds that chemically attach at least some of the active sites to the solid. In some embodiments, at least one metal may be combined with a solid to provide a catalyst for the conversion of muconic acid to adipic acid.

In some embodiments, a metallic catalyst comprising a solid may include at least one active site either incorporated into the solid or deposited on the solid, wherein the at least one active site is at least one noble metal, or mixtures thereof. In some cases, a metallic catalyst including a solid may have at least two active sites either incorporated into the solid or deposited on the solid, wherein the at least two active sites are at least two noble metals, or mixtures thereof. As used herein, a "noble metal" refers to at least one of ruthenium, rhodium, palladium, silver, osmium, iridium, platinum, and/or gold. In some further embodiments, a metallic catalyst that includes a solid may have at least one active site either incorporated into the solid or deposited on the solid, wherein the at least one active site is at least one of a noble metal, mercury, rhenium, and/or copper. In some examples, a metallic catalyst including a solid may have at least two active sites either incorporated into the solid or deposited on the solid, wherein the at least two active sites are at least two of a noble metal, mercury, rhenium, and/or copper.

A metallic catalyst that includes a solid may be constructed from solid carbon and at least one of palladium, platinum, and/or ruthenium. At least one metal of a bimetallic catalyst may be at least one of palladium, platinum, and/or ruthenium, may be present in metallic form and/or as a salt. Palladium may be in the 0, +1, +2, +3, +4 oxidation state, or mixtures thereof. Platinum may be in the 0, +1, +2, +3, +4 oxidation state, or mixtures thereof. Ruthenium may be in the −2, 0, +1, +2, +3, +4, +5, +6, +7, +8 oxidation state, or mixtures thereof. Furthermore, a solid used as a support for a metallic catalyst may be at least one of carbon nanotubes, graphene, and/or activated carbon. A bimetallic catalyst may be constructed from intermetallic/core shell nanoparticles. Thus, a bimetallic catalyst comprising two metals and a solid may be utilized to catalyze the hydrogenation reaction of cis,cis-muconic acid with diatomic hydrogen to form at least one of adipic acid, 1,6-hexanediol, or mixtures thereof.

Example 8: Catalyst Synthesis

Commercial monometallic noble metal catalysts were screened for their hydrogenation activity with muconic acid. Catalysts at 5 wt % loading on activated carbon were obtained from Sigma Aldrich (Pt, Pd, and Ru) and 1 wt % Pd/C was obtained from Alfa Aesar. Virgin catalyst materials were initially characterized to determine their average crystallite size and long-range order by X-ray diffraction, support surface area and pore volume by nitrogen physisorption, and active metal surface area by hydrogen chemisorption, with details described elsewhere. Due to the high sensitivity of Pd dispersion with temperature, Pd samples were reduced under flowing hydrogen (50 mL/min, 10% $H_2$ in Ar) at moderate temperature (125° C., 3° C./min) and held for 1 hour. Following reduction, Pd samples were purged for 1 hour under Ar and cooled to 45° C. prior to $H_2/O_2$ titration. For calculations of Pd dispersion, the amount of hydrogen uptake that followed the second oxygen titration was used. A stoichiometry of 0.667 Pd sites per $H_2$ molecule was assumed to remove oxidized Pd—O species in the form of water and form the reduced Pd—H species.

Example 9: Catalyst Synthesis

Platinum group metal catalysts (Pt, Rh, Ru, Pd) were synthesized on powder carbon and silica supports to evaluate their activity and stability for muconic acid hydrogenation. For batch reaction studies, Darco activated carbon (Sigma Aldrich) and Davisil Grade 633 high surface area silica (Sigma Aldrich) were used. Supports were initially sieved >270 mesh (<53 μm) to minimize the impact of mass transfer on observed kinetics. The silica support was calcined at 500° C. in air prior to loading metals, while the activated carbon support was used as received. Catalysts were prepared with the following metal salt precursors: palladium acetate (Sigma Aldrich), rhodium nitrate hydrate (Sigma Aldrich), ruthenium chloride hydrate (Sigma Aldrich), chloroplatinic acid (CPA) (Sigma Aldrich), and ammonium tetraammineplatinum nitrate (PTA) (Sigma Aldrich). Pd, Ru, and Rh catalysts were prepared by incipient wetness, while Pt catalysts were prepared by strong electrostatic adsorption (SEA) to improve dispersion due to the low activity. For SEA catalyst synthesis, 1.9 g of support was added to 50 mL of DI water, and the pH was adjusted to facilitate protonation/deprotonation of the support (pH 12 with NaOH for silica, pH 2.9 with HCl for AC). In another bottle, the appropriate catalyst precursor was dissolved in 50 mL of DI water (PTA for silica, CPA for activated carbon). The two bottles were mixed together with stirring for 1 hour, followed by vacuum filtration to recover the catalyst. The catalyst was washed twice with 50 mL of DI water and left to dry overnight in air at room temperature. After loading, catalysts were dried at 110° C. and reduced in hydrogen flowing at 200 sccm for 2 hours at temperature. Due to the sensitivity of Pd dispersion with temperature, Pd catalysts were reduced at 125° C. while Pt, Rh, and Ru catalysts were reduced at 250° C.

For flow reactor studies, extruded activated carbon pellets (Norit Rx 3 Extra, Cabot Norit) were initially crushed and sieved between 80-100 mesh (150-180 μm) to allow for a moderate catalyst bed pressure drop (<5 psig) while still facilitating mass transfer. Rh was loaded onto the support by incipient wetness using ruthenium chloride hydrate (Sigma Aldrich), dried at 110° C., and reduced ex situ prior to use at 250° C. in flowing hydrogen.

Catalysts were characterized after synthesis and reduction to determine their virgin properties, as well as post-reaction for flow reactor experiments. X-ray diffraction (XRD) was used to assess catalyst metal crystallite size and bulk long-range order. Catalyst support surface area, pore volume, and average pore diameter were measured by BET nitrogen physisorption. Scanning electron microscopy, coupled to energy dispersive electron spectroscopy, was used to evaluate of metal crystallite distribution on the support. Chemisorption was used with to evaluate crystallite metal dispersion, defined as the percentage of metal surface sites compared to the total metal loaded.

Example 10: Catalyst Testing

For batch reactor activity studies, reactions were performed in using a Para 5000 Multi-reactor system (Parr Instruments). Commercial cis,cis-muconic acid in the amount of 200 mg (Sigma Aldrich) was dissolved in 19.8 g of 200 proof ethanol. The muconic acid solution and 15 mg of catalyst were then loaded into 75-mL vessels equipped with magnetic stirring. Hydrogenation reactions were performed at 24° C. with hydrogen supplied at a constant 24 bar and stirring at 1600 rpm. Duplication reactions were performed at minimum, with error bars indicating sample standard deviations. Samples were collected via an in situ sample port, syringe filtered, and analyzed by HPLC, as described below. After the reaction, the reactor contents were vacuum filtered (0.2-µm PES filter assembly, Nalgene) to remove catalyst particles, and subsequently the liquid filtrate was analyzed by ICP-OES to examine active metal leaching.

For flow reactor stability studies, reactions were performed using a Parr Tubular reactor system (Parr Instruments) operated in a down-flow trickle-bed configuration. The system was outfitted with a HPLC pump to deliver liquid phase reactants (Series III Scientific Instrument), pair of mass flow controllers to control inert and hydrogen gas delivery (Brooks), tube-in-tube heat exchanger for cooling the reactor effluent, high-pressure 1-L stainless steel knock-out pot with bottom sampling valve, and a solenoid-controlled backpressure regulator (Tescom) to maintain system pressure. Reactions were performed in trickle down flow configuration, with gas and liquid reagents fed to through the top of a 32" long, ¼" inner diameter stainless steel reaction tube. The tube temperature was monitored and controlled using an internal thermocouple centered in the catalyst bed and three furnace wall thermocouples. The tube was initially packed halfway with inert 1-mm glass beads (Sigma Aldrich) held in place with quartz wool (Quartz Scientific Inc.). The catalyst bed was then loaded at the tube midheight. Inert quartz sand (Quartz Scientific Inc.) sieved to <60 mesh (>250 µm) was placed at the base and top of the carbon catalyst packing to serve as a support. The remaining reactor tube void was then filled with inert glass beads and sealed with quartz wool.

Continuous hydrogenation reactions were performed with hydrogen supplied at 200 sccm and a system pressure maintained at 24 bar. Temperature was varied from 50-78° C., as indicated. The mobile phase consisted of biologically derived muconic acid purified with activated carbon, precipitated by temperature-pH shift crystallization, dissolved in 200-proof ethanol (8 g/L), and filtered (0.2-µm PES) to remove insoluble salts. Commercial succinic acid (Sigma Aldrich, ≥99.0% reagent purity) was added as an internal standard (0.8 g/L). The liquid flow rate was varied from 0.2-0.5 mL/min, as indicated. Liquid reactor effluent samples collected from the knockout pot were syringe-filtered, and analyzed by HPLC and GC-MS, as described below. Periodically, the liquid filtrate was analyzed by ICP-MS to detect catalyst metal leaching. After testing, the reactor was cooled to room temperature, depressurized, and 500 mL of ethanol was flushed through the catalyst bed, followed by drying under 200 sccm nitrogen. The catalyst bed packing solids were then sieved between 80-100 mesh (150-180 µm) to recover the catalyst granules for further analysis.

Nylon-6,6 Polymerization with Bio-Adipic Acid

Bio-adipic acid produced from muconic acid was then polymerized with 1,6-hexanediamine to form nylon-6,6 for comparative material testing to petrochemical adipic acid. Bench-scale condensation polymerizations were conducted using the nylon rope reaction shown in FIG. 24. After producing nylon fibers from both bio-adipic acid and commercial adipic acid, polymer materials were dried and characterized to determine their thermal and physicochemical properties.

Thermal analysis of both nylon materials by DSC showed comparable melting and glass transition temperatures, similar to values reported in literature for nylon-6,6, as shown in Table 5 below. Clean thermal traces were observed for nylon produced from biologically derived adipic acid, with a heat of fusion comparable (50.2 J/g) to literature values (51.3 J/g).

Measurement of the intrinsic viscosity by dilute solution viscometry showed similar values for the two nylon materials, and calculations of the viscosity average MW showed that polymerization had taken place to a comparable extent for bio-adipic acid (1,920±20 g/mol) and chemical adipic acid (2,230±40 g/mol). However, the limitation of the nylon rope trick was apparent for achieving industrially relevant nylon MW values (40,000-60,000 g/mol).

TABLE 5

Properties of nylon-6,6 produced using commercial adipic acid of chemical origin and bio-adipic acid generated in this work from the catalytic hydrogenation of muconic acid.

| Nylon-6,6 Properties | Adipic Acid Chemical | Adipic Acid Biological | Literature for Nylon-6,6 |
|---|---|---|---|
| Melting Temp (° C.) | 258 | 264 | 262 |
| Glass Transition (° C.)[a] | 55 | 46 | 50 |
| Heat of fusion (J/g) | 37.8 | 50.2 | 51.3 |
| Crystallinity (%) | 19.9 | 26.4 | 27.0 |
| Intrinsic Viscosity (mL/g)[b] | 26.5 ± 0.9 | 24.1 ± 0.6 | 79–174 |
| Viscosity Avg. MW (g/mol)[b] | 2,230 ± 40 | 1,920 ± 20 | 40,000–60,000 |

[a]$T_g$ determined from literature for 27% crystallinity and is known to vary.
[b]Standard deviation values reported for four solutions tested in triplicate.

FIG. 25 illustrates a process flow diagram of one example of a portion of a biorefinery, downstream of the biocatalytic bioreactor corresponding to the muconic acid separation/purification and upgrading portions. Thus, FIG. 25 summarizes one hypothetical process and these separation/purification and upgrading steps to convert culture broth from a bioreactor to adipic acid.

Referring to FIG. 25, Area 100 of the process model focuses on purification and recovery of muconic acid from the biological culture broth. Muconic acid broth may be purified over parallel activated carbon treatment beds to remove non-target aromatic impurities. Spent activated carbon from purification may be thermally regenerated onsite by kiln combustion due to the high boiling point of adsorbed organics. After purification, low pH and low temperature crystallization may be employed to recover muconic acid based on a solubility of 3.5 g/L at pH 2 and 10° C. Concentrated sulfuric acid may be used for pH adjustment, producing $Na_2SO_4$ (2 g of $Na_2SO_4$ per 1 g of muconic acid solid) that co-crystallizes at a solubility limit of 82.8 g/L at 10° C. Rotary filtration and rotary drying may then be employed to recover mixed solid crystals, with the filter broth effluent treated as wastewater. Mixed solid crystals may be added to ethanol in a heated stirred tank at 70° C. to dissolve muconic acid, while insoluble $Na_2SO_4$ may be separated by rotary filtration and treated as solid waste.

Area 200 shown in FIG. 25 focuses on the purification and catalytic conversion of muconic acid to adipic acid, with subsequent product recovery. Muconic acid in ethanol may be initially pressurized to 350 psig using a positive-displacement pump for feeding to the reactor. On site hydrogen may be supplied at ambient temperature and pressure, utilizing a 3-stage compression train with inter-stage cooling to deliver hydrogen at 350 psig. Muconic acid, ethanol, and hydrogen may then be mixed and introduced to a trickle bed reactor operating at 70° C. with a weight hour space velocity (WHSV), defined as the weight of liquid solution processed per hour divided by the weight of catalyst material, of 5 $h^{-1}$. Hydrogenation of muconic acid may be achieved utilizing a 2% Rh/C catalyst, to produce substantially pure adipic acid.

Following hydrogenation, adipic acid may be recovered from solution by ethanol evaporation and crystallization. The stream of adipic acid in ethanol exiting the reactor may be mixed with the crystallizer recycle stream and concentrated to 360 g/L at 82° C., below the adipic acid/ethanol solubility limit of 363 g/L at 60° C. The solution may then be cooled to 10° C. to partially crystallize adipic acid based on a solubility limit of ~67 g/L at 10° C., with the remaining solution recycled to the inlet of the evaporator. Rotary filtration and drying may then be employed to dry crystals, with an assumed net adipic acid recovery of about 98% post-hydro genation.

While a number of exemplary aspects and embodiments have been discussed above, those of skill in the art will recognize certain modifications, permutations, additions and sub combinations thereof. It is therefore intended that the following appended claims and claims hereafter introduced are interpreted to include all such modifications, permutations, additions and sub-combinations as are within their true spirit and scope.

What is claimed is:

1. A genetically modified prokaryotic microorganism comprising:
an exogenous genetic addition encoding at least a 3-dehydroshikimate dehydratase and a phenol monooxygenase, wherein said genetically modified prokaryotic microorganism is capable of producing cis, cis-muconic acid.

2. The genetically modified prokaryotic microorganism of claim 1, further comprising:
an endogenous gene deletion that ablates expression of at least one of a protocatechuic acid dioxygenase, a muconate lactonizing enzyme, or a muconolactone isomerase.

3. The genetically modified prokaryotic microorganism of claim 1, further comprising:
an exogenous genetic addition encoding a vanillic acid demethylase.

4. The genetically modified prokaryotic microorganism of claim 1, further comprising a deletion of an endogenous catabolite repression control gene.

5. The genetically modified prokaryotic microorganism of claim 1, further comprising an exogenous genetic addition encoding at least a protocatechuic acid decarboxylase.

6. The genetically modified prokaryotic microorganism of claim 5, wherein said protocatechuic acid decarboxylase comprises at least one of EcdB or EcdD.

7. The genetically modified prokaryotic microorganism of claim 1, wherein said 3-dehydroshikimate dehydratase is from *Bacillus cereus*.

8. The genetically modified prokaryotic microorganism of claim 7, wherein said 3-dehydroshikimate dehydratase comprises at least one of AroZ or AsbF.

9. The genetically modified prokaryotic microorganism of claim 1, wherein said phenol monooxygenase is from *Pseudomonas* sp. CF600.

10. The genetically modified prokaryotic microorganism of claim 9, wherein said phenol monooxygenase comprises at least one DmpKLMNOP or PheA.

11. The genetically modified prokaryotic microorganism of claim 2, wherein said protocatechuic acid dioxygenase comprises at least one of PcaH or PcaG.

12. The genetically modified prokaryotic microorganism of claim 2, wherein at least one of said muconate lactonizing enzyme or said muconolactone isomerase comprises at least one of CatB or CatC.

13. The genetically modified prokaryotic microorganism of claim 3, wherein said vanillic acid demethylase comprises at least one of VanA, VanB, or LigM.

14. The genetically modified prokaryotic microorganism of claim 1, wherein the genetically modified prokaryotic microorganism is from the genus *Pseudomonas*.

15. The genetically modified prokaryotic microorganism of claim 14, wherein the genetically modified prokaryotic microorganism is *P. putida*, *P. fluorescens*, or *P. stutzeri*.

16. The genetically modified prokaryotic microorganism of claim 15, wherein said genetically modified prokaryotic microorganism is *P. putida* KT2440.

17. The genetically modified prokaryotic microorganism of claim 10, wherein said DmpKLMNOP has an amino acid sequence that is at least 90% identical to the amino acid sequence set forth in SEQ ID Nos: 24, 26, 28, 30, 32, and 34.

18. The genetically modified prokaryotic microorganism of claim 10, wherein said PheA has an amino acid sequence that is at least 90% identical to the amino acid sequence set forth in SEQ ID NO: 36.

19. The genetically modified prokaryotic microorganism of claim 13, wherein said LigM has an amino acid sequence that is at least 90% identical to the amino acid sequence set forth in SEQ ID NO: 38.

20. The genetically modified prokaryotic microorganism of claim 11, wherein said PcaH has an amino acid sequence that is at least 90% identical to the amino acid sequence set forth in SEQ ID NO: 10.

21. The genetically modified prokaryotic microorganism of claim 11, wherein said PcaG has an amino acid sequence that is at least 90% identical to the amino acid sequence set forth in SEQ ID NO: 12.

22. The genetically modified prokaryotic microorganism of claim 12, wherein said CatB has an amino acid sequence that is at least 90% identical to the amino acid sequence set forth in SEQ ID NO: 2.

23. The genetically modified prokaryotic microorganism of claim 12, wherein said CatC has an amino acid sequence that is at least 90% identical to the amino acid sequence set forth in SEQ ID NO: 4.

24. A process comprising:
contacting a culture broth comprising a lignin depolymerization compound with a genetically modified prokaryotic microorganism comprising a first exogenous genetic addition encoding at least a 3-dehydroshikimate dehydratase and a phenol monooxygenase, wherein:
said genetically modified prokaryotic microorganism is capable of converting at least a portion of said lignin depolymerization compound to cis, cis-muconic acid.

25. The process of claim 24, wherein said lignin depolymerization compound comprises at least one of p-coumaric acid, ferulic acid, benzoic acid, phenol, coniferyl alcohol, caffeic acid, vanillin, or 4-hydroxybenzoic acid.

26. The process of claim 24, wherein:
said culture broth further comprises a polysaccharide depolymerization compound, and
said genetically modified prokaryotic microorganism is capable of converting at least a portion of said polysaccharide depolymerization compound to cis, cis-muconic acid.

27. The process of claim 24, wherein said polysaccharide depolymerization compound comprises at least one of glucose, xylose, arabinose, mannose, galactose, or rhamnose.

* * * * *

SEQUENCE LISTING

```
<160> NUMBER OF SEQ ID NOS: 56

<210> SEQ ID NO 1
<211> LENGTH: 1122
<212> TYPE: DNA
<213> ORGANISM: Pseudomonas putida
<220> FEATURE:
<221> NAME/KEY: CDS
<222> LOCATION: (1)..(1122)

<400> SEQUENCE: 1 atg aca agc gtg ctg att gaa cac ata gat gca att atc gtc gat ctc      48
Met Thr Ser Val Leu Ile Glu His Ile Asp Ala Ile Ile Val Asp Leu
1               5                   10                  15 ccg acc att cgc ccg cac aag ctg gcg atg cac acc atg cag cag cag      96
Pro Thr Ile Arg Pro His Lys Leu Ala Met His Thr Met Gln Gln Gln
            20                  25                  30 acc ctg gtg gta ttg cga ctg cgc tgc agc gat ggc gtg gaa ggc atc     144
Thr Leu Val Val Leu Arg Leu Arg Cys Ser Asp Gly Val Glu Gly Ile
        35                  40                  45 ggt gaa gcc acc acc atc ggt ggc ctg gcg tat ggc tac gaa agc ccc     192
Gly Glu Ala Thr Thr Ile Gly Gly Leu Ala Tyr Gly Tyr Glu Ser Pro
    50                  55                  60 gaa ggg atc aag gcc aac atc gac gcg tac ctc gcc cca gcg ttg att     240
Glu Gly Ile Lys Ala Asn Ile Asp Ala Tyr Leu Ala Pro Ala Leu Ile
65                  70                  75                  80 ggc ctg ccg gca gac aac atc aat gcc gcc atg ctc aag ctg gac aag     288
Gly Leu Pro Ala Asp Asn Ile Asn Ala Ala Met Leu Lys Leu Asp Lys
                85                  90                  95 ctg gcc aag ggc aac acc ttc gcc aag tcc ggc atc gaa agc gcc ttg     336
Leu Ala Lys Gly Asn Thr Phe Ala Lys Ser Gly Ile Glu Ser Ala Leu
            100                 105                 110 ctc gac gcc cag ggc aaa cgc ctg ggc ctg ccg gtc agc gaa ctg ctg     384
Leu Asp Ala Gln Gly Lys Arg Leu Gly Leu Pro Val Ser Glu Leu Leu
        115                 120                 125
```

```
ggt ggc cgc gtg cgt gac agc ctg gaa gtg gcc tgg acc ctg gcc agc      432
Gly Gly Arg Val Arg Asp Ser Leu Glu Val Ala Trp Thr Leu Ala Ser
130                 135                 140 ggc gac acc gcc cgc gac atc gcc gaa gca cag cac atg ctg gac att      480
Gly Asp Thr Ala Arg Asp Ile Ala Glu Ala Gln His Met Leu Asp Ile
145                 150                 155                 160 cgc cgg cac cgc gtg ttc aag ctg aaa atc ggc gcc aac ccg gtg gcg      528
Arg Arg His Arg Val Phe Lys Leu Lys Ile Gly Ala Asn Pro Val Ala
            165                 170                 175 cag gac ctc aag cac gtg gtc gcg atc aag cgc gag ctg ggt gac agc      576
Gln Asp Leu Lys His Val Val Ala Ile Lys Arg Glu Leu Gly Asp Ser
        180                 185                 190 gcc agc gtg cgg gtc gac gtc aac cag tac tgg gac gag tcc cag gcc      624
Ala Ser Val Arg Val Asp Val Asn Gln Tyr Trp Asp Glu Ser Gln Ala
    195                 200                 205 atc cgc gcc tgc cag gta ttg ggc gac aac ggc atc gac ctg atc gag      672
Ile Arg Ala Cys Gln Val Leu Gly Asp Asn Gly Ile Asp Leu Ile Glu
210                 215                 220 cag ccg att tcg cgc atc aac cgc gct ggc cag gtg cgc ctg aac cag      720
Gln Pro Ile Ser Arg Ile Asn Arg Ala Gly Gln Val Arg Leu Asn Gln
225                 230                 235                 240 cgc agt ccg gct ccg atc atg gcc gat gag tcg atc gaa agc gtc gag      768
Arg Ser Pro Ala Pro Ile Met Ala Asp Glu Ser Ile Glu Ser Val Glu
            245                 250                 255 gac gcc ttc agc ctg gcc gcc gac ggc gcc gcc agc atc ttc gcc ctg      816
Asp Ala Phe Ser Leu Ala Ala Asp Gly Ala Ala Ser Ile Phe Ala Leu
        260                 265                 270 aaa atc gcc aag aat ggt ggc ccg cgc gcg gtt ctg cgc act gca cag      864
Lys Ile Ala Lys Asn Gly Gly Pro Arg Ala Val Leu Arg Thr Ala Gln
    275                 280                 285 atc gcc gag gcc gct ggc atc gcc ttg tac ggc ggc acc atg ctc gaa      912
Ile Ala Glu Ala Ala Gly Ile Ala Leu Tyr Gly Gly Thr Met Leu Glu
290                 295                 300 ggt tcg atc ggc acc ctg gct tcg gct cat gca ttc ctc acc ctg cgc      960
Gly Ser Ile Gly Thr Leu Ala Ser Ala His Ala Phe Leu Thr Leu Arg
305                 310                 315                 320 cag ctc acc tgg ggt aca gag ctg ttc ggg ccg ctg ctg acc gag         1008
Gln Leu Thr Trp Gly Thr Glu Leu Phe Gly Pro Leu Leu Thr Glu
            325                 330                 335 gag atc gtc aac gag ccg ccg caa tac cgc gac ttc cag ctg cac atc    1056
Glu Ile Val Asn Glu Pro Pro Gln Tyr Arg Asp Phe Gln Leu His Ile
        340                 345                 350 ccc cac acc cca ggc ctg ggc ctg acg ttg gac gaa cag cgc ctg gcg    1104
Pro His Thr Pro Gly Leu Gly Leu Thr Leu Asp Glu Gln Arg Leu Ala
    355                 360                 365 cgc ttc gcc cgt cgc tga                                            1122
Arg Phe Ala Arg Arg
    370

<210> SEQ ID NO 2
<211> LENGTH: 373
<212> TYPE: PRT
<213> ORGANISM: Pseudomonas putida

<400> SEQUENCE: 2

Met Thr Ser Val Leu Ile Glu His Ile Asp Ala Ile Ile Val Asp Leu
1               5                   10                  15

Pro Thr Ile Arg Pro His Lys Leu Ala Met His Thr Met Gln Gln Gln
            20                  25                  30

Thr Leu Val Val Leu Arg Leu Arg Cys Ser Asp Gly Val Glu Gly Ile
```

```
                35                  40                  45
Gly Glu Ala Thr Thr Ile Gly Gly Leu Ala Tyr Gly Tyr Glu Ser Pro
 50                  55                  60

Glu Gly Ile Lys Ala Asn Ile Asp Ala Tyr Leu Ala Pro Ala Leu Ile
 65                  70                  75                  80

Gly Leu Pro Ala Asp Asn Ile Asn Ala Met Leu Lys Leu Asp Lys
                 85                  90                  95

Leu Ala Lys Gly Asn Thr Phe Ala Lys Ser Gly Ile Glu Ser Ala Leu
                100                 105                 110

Leu Asp Ala Gln Gly Lys Arg Leu Gly Leu Pro Val Ser Glu Leu Leu
                115                 120                 125

Gly Gly Arg Val Arg Asp Ser Leu Glu Val Ala Trp Thr Leu Ala Ser
130                 135                 140

Gly Asp Thr Ala Arg Asp Ile Ala Glu Ala Gln His Met Leu Asp Ile
145                 150                 155                 160

Arg Arg His Arg Val Phe Lys Leu Lys Ile Gly Ala Asn Pro Val Ala
                165                 170                 175

Gln Asp Leu Lys His Val Val Ala Ile Lys Arg Glu Leu Gly Asp Ser
                180                 185                 190

Ala Ser Val Arg Val Asp Val Asn Gln Tyr Trp Asp Glu Ser Gln Ala
                195                 200                 205

Ile Arg Ala Cys Gln Val Leu Gly Asp Asn Gly Ile Asp Leu Ile Glu
210                 215                 220

Gln Pro Ile Ser Arg Ile Asn Arg Ala Gly Gln Val Arg Leu Asn Gln
225                 230                 235                 240

Arg Ser Pro Ala Pro Ile Met Ala Asp Glu Ser Ile Glu Ser Val Glu
                245                 250                 255

Asp Ala Phe Ser Leu Ala Ala Asp Gly Ala Ala Ser Ile Phe Ala Leu
                260                 265                 270

Lys Ile Ala Lys Asn Gly Gly Pro Arg Ala Val Leu Arg Thr Ala Gln
                275                 280                 285

Ile Ala Glu Ala Ala Gly Ile Ala Leu Tyr Gly Gly Thr Met Leu Glu
290                 295                 300

Gly Ser Ile Gly Thr Leu Ala Ser Ala His Ala Phe Leu Thr Leu Arg
305                 310                 315                 320

Gln Leu Thr Trp Gly Thr Glu Leu Phe Gly Pro Leu Leu Leu Thr Glu
                325                 330                 335

Glu Ile Val Asn Glu Pro Pro Gln Tyr Arg Asp Phe Gln Leu His Ile
                340                 345                 350

Pro His Thr Pro Gly Leu Gly Leu Thr Leu Asp Glu Gln Arg Leu Ala
                355                 360                 365

Arg Phe Ala Arg Arg
    370

<210> SEQ ID NO 3
<211> LENGTH: 291
<212> TYPE: DNA
<213> ORGANISM: Pseudomonas putida
<220> FEATURE:
<221> NAME/KEY: CDS
<222> LOCATION: (1)..(291)

<400> SEQUENCE: 3 atg ttg ttc cac gtg aag atg acc gtg aag ctg ccg gtc gac atg gac    48
Met Leu Phe His Val Lys Met Thr Val Lys Leu Pro Val Asp Met Asp
 1               5                  10                  15
```

```
ccg gcc aag gcc gcc cag ctc aag gcc gac gaa aag gaa ctg gcc cag        96
Pro Ala Lys Ala Ala Gln Leu Lys Ala Asp Glu Lys Glu Leu Ala Gln
         20                  25                  30 cgc ctg cag cgc gaa ggc atc tgg cgt cac ctg tgg cgc att gcc ggg       144
Arg Leu Gln Arg Glu Gly Ile Trp Arg His Leu Trp Arg Ile Ala Gly
     35                  40                  45 cat tac gcc aac tac agc gtg ttc gat gtg ccc agc gtc gag gca ttg       192
His Tyr Ala Asn Tyr Ser Val Phe Asp Val Pro Ser Val Glu Ala Leu
 50                  55                  60 cat gac acg ctg atg cag ctg ccg ctg ttc ccg tac atg gat atc gag       240
His Asp Thr Leu Met Gln Leu Pro Leu Phe Pro Tyr Met Asp Ile Glu
 65                  70                  75                  80 gtc gac ggc ctg tgt cgg cat ccc tcg tct att cac agc gac gat cgc       288
Val Asp Gly Leu Cys Arg His Pro Ser Ser Ile His Ser Asp Asp Arg
                 85                  90                  95 tga                                                                   291

<210> SEQ ID NO 4
<211> LENGTH: 96
<212> TYPE: PRT
<213> ORGANISM: Pseudomonas putida

<400> SEQUENCE: 4

Met Leu Phe His Val Lys Met Thr Val Lys Leu Pro Val Asp Met Asp
 1               5                  10                  15

Pro Ala Lys Ala Ala Gln Leu Lys Ala Asp Glu Lys Glu Leu Ala Gln
         20                  25                  30

Arg Leu Gln Arg Glu Gly Ile Trp Arg His Leu Trp Arg Ile Ala Gly
     35                  40                  45

His Tyr Ala Asn Tyr Ser Val Phe Asp Val Pro Ser Val Glu Ala Leu
 50                  55                  60

His Asp Thr Leu Met Gln Leu Pro Leu Phe Pro Tyr Met Asp Ile Glu
 65                  70                  75                  80

Val Asp Gly Leu Cys Arg His Pro Ser Ser Ile His Ser Asp Asp Arg
                 85                  90                  95

<210> SEQ ID NO 5
<211> LENGTH: 1068
<212> TYPE: DNA
<213> ORGANISM: Pseudomonas putida
<220> FEATURE:
<221> NAME/KEY: CDS
<222> LOCATION: (1)..(1068)

<400> SEQUENCE: 5 atg tac ccc aaa aac acc tgg tac gtc gcc tgc acc ccc gat gag atc        48
Met Tyr Pro Lys Asn Thr Trp Tyr Val Ala Cys Thr Pro Asp Glu Ile
 1               5                  10                  15 gcc acc aaa ccc ctg ggc cgg cag atc tgc ggg gaa aaa atc gtg ttc        96
Ala Thr Lys Pro Leu Gly Arg Gln Ile Cys Gly Glu Lys Ile Val Phe
         20                  25                  30 tac cgc gcc cgc gag aac caa gta gcc gcc gtc gag gac ttc tgc ccg       144
Tyr Arg Ala Arg Glu Asn Gln Val Ala Ala Val Glu Asp Phe Cys Pro
     35                  40                  45 cac cgc ggc gca ccg ttg tcg ttg ggc tat gtc gag gac ggc aac ctg       192
His Arg Gly Ala Pro Leu Ser Leu Gly Tyr Val Glu Asp Gly Asn Leu
 50                  55                  60 gtg tgc ggc tac cac ggc ctg gtg atg ggt tgc gac ggc aag acc gtg       240
Val Cys Gly Tyr His Gly Leu Val Met Gly Cys Asp Gly Lys Thr Val
 65                  70                  75                  80
```

```
tcg atg ccg ggc caa cgg gtg cgt ggc ttc ccc tgc aac aag acc ttt    288
Ser Met Pro Gly Gln Arg Val Arg Gly Phe Pro Cys Asn Lys Thr Phe
            85                  90                  95 gcg gcc gtc gag cgc tat ggc ttc atc tgg gtc tgg ccc ggt gac cag    336
Ala Ala Val Glu Arg Tyr Gly Phe Ile Trp Val Trp Pro Gly Asp Gln
            100                 105                 110 gcg cag gcc gac ccg gcg ctg att ccg cat ctg gaa tgg gcg gtg agt    384
Ala Gln Ala Asp Pro Ala Leu Ile Pro His Leu Glu Trp Ala Val Ser
        115                 120                 125 gat gag tgg gcc tac ggc ggc ggg ctg ttc cac atc ggt tgc gac tac    432
Asp Glu Trp Ala Tyr Gly Gly Gly Leu Phe His Ile Gly Cys Asp Tyr
    130                 135                 140 cgc ctg atg atc gac aac ctc atg gac ctc acc cat gaa acc tat gtg    480
Arg Leu Met Ile Asp Asn Leu Met Asp Leu Thr His Glu Thr Tyr Val
145                 150                 155                 160 cac gcc tcc agc atc ggc cag aag gag atc gac gag gca ccg ccg gtc    528
His Ala Ser Ser Ile Gly Gln Lys Glu Ile Asp Glu Ala Pro Pro Val
            165                 170                 175 acc acc gtc acc ggc gac gaa gtg gtc acc gcc cgg cac atg gaa aac    576
Thr Thr Val Thr Gly Asp Glu Val Val Thr Ala Arg His Met Glu Asn
            180                 185                 190 atc atg gcg cca ccg ttc tgg cgc atg gcc ttg cgt ggc aat ggc ctg    624
Ile Met Ala Pro Pro Phe Trp Arg Met Ala Leu Arg Gly Asn Gly Leu
        195                 200                 205 gcc gac gat gta cca gtg gac cgc tgg cag atc tgc cgt ttc acc cca    672
Ala Asp Asp Val Pro Val Asp Arg Trp Gln Ile Cys Arg Phe Thr Pro
    210                 215                 220 cct agc cat gtg ctg atc gaa gtg ggt gta gcg cat gcc ggc aag ggc    720
Pro Ser His Val Leu Ile Glu Val Gly Val Ala His Ala Gly Lys Gly
225                 230                 235                 240 ggc tac cac gcc gag gca cag cat aag gcg tcg agc atc gtg gtc gac    768
Gly Tyr His Ala Glu Ala Gln His Lys Ala Ser Ser Ile Val Val Asp
            245                 250                 255 ttc atc acc cct gag agc gat acc tct atc tgg tac ttc tgg ggc atg    816
Phe Ile Thr Pro Glu Ser Asp Thr Ser Ile Trp Tyr Phe Trp Gly Met
            260                 265                 270 gcg cgc aac ttc gct gcg cac gac cag acc ctg acc gac aac att cgt    864
Ala Arg Asn Phe Ala Ala His Asp Gln Thr Leu Thr Asp Asn Ile Arg
        275                 280                 285 gag ggc cag ggc aag att ttc agc gaa gac ctg gaa atg ctc gaa cgc    912
Glu Gly Gln Gly Lys Ile Phe Ser Glu Asp Leu Glu Met Leu Glu Arg
    290                 295                 300 cag cag cag aac ctg ctg gcc cac ccc gag cgc aac ttg ctg aag ctg    960
Gln Gln Gln Asn Leu Leu Ala His Pro Glu Arg Asn Leu Leu Lys Leu
305                 310                 315                 320 aat atc gac gcc ggc ggc gtg cag tca cgc aaa gtg ctg gag cgg atc   1008
Asn Ile Asp Ala Gly Gly Val Gln Ser Arg Lys Val Leu Glu Arg Ile
            325                 330                 335 atc gcc caa gag cgt gcg ccg cag ccg caa ctg atc gcc acc agc gcc   1056
Ile Ala Gln Glu Arg Ala Pro Gln Pro Gln Leu Ile Ala Thr Ser Ala
            340                 345                 350 aac cct gcc tga                                                   1068
Asn Pro Ala
        355
```

<210> SEQ ID NO 6
<211> LENGTH: 355
<212> TYPE: PRT
<213> ORGANISM: Pseudomonas putida

<400> SEQUENCE: 6

| | | | | | | | | | | | | | | |
|---|---|---|---|---|---|---|---|---|---|---|---|---|---|---|
|Met|Tyr|Pro|Lys|Asn|Thr|Trp|Tyr|Val|Ala|Cys|Thr|Pro|Asp|Glu|Ile|
|1| | | |5| | | | |10| | | | |15|
|Ala|Thr|Lys|Pro|Leu|Gly|Arg|Gln|Ile|Cys|Gly|Glu|Lys|Ile|Val|Phe|
| | | |20| | | | |25| | | | |30| |
|Tyr|Arg|Ala|Arg|Glu|Asn|Gln|Val|Ala|Ala|Val|Glu|Asp|Phe|Cys|Pro|
| | |35| | | | |40| | | | |45| | |
|His|Arg|Gly|Ala|Pro|Leu|Ser|Leu|Gly|Tyr|Val|Glu|Asp|Gly|Asn|Leu|
| |50| | | | |55| | | | |60| | | |
|Val|Cys|Gly|Tyr|His|Gly|Leu|Val|Met|Gly|Cys|Asp|Gly|Lys|Thr|Val|
|65| | | | |70| | | | |75| | | | |80|
|Ser|Met|Pro|Gly|Gln|Arg|Val|Arg|Gly|Phe|Pro|Cys|Asn|Lys|Thr|Phe|
| | | | |85| | | | |90| | | | |95| |
|Ala|Ala|Val|Glu|Arg|Tyr|Gly|Phe|Ile|Trp|Val|Trp|Pro|Gly|Asp|Gln|
| | | |100| | | | |105| | | | |110| | |
|Ala|Gln|Ala|Asp|Pro|Ala|Leu|Ile|Pro|His|Leu|Glu|Trp|Ala|Val|Ser|
| | |115| | | | |120| | | | |125| | | |
|Asp|Glu|Trp|Ala|Tyr|Gly|Gly|Leu|Phe|His|Ile|Gly|Cys|Asp|Tyr|
| |130| | | | |135| | | | |140| | | |
|Arg|Leu|Met|Ile|Asp|Asn|Leu|Met|Asp|Leu|Thr|His|Glu|Thr|Tyr|Val|
|145| | | | |150| | | | |155| | | | |160|
|His|Ala|Ser|Ser|Ile|Gly|Gln|Lys|Glu|Ile|Asp|Glu|Ala|Pro|Pro|Val|
| | | | |165| | | | |170| | | | |175| |
|Thr|Thr|Val|Thr|Gly|Asp|Glu|Val|Val|Thr|Ala|Arg|His|Met|Glu|Asn|
| | | |180| | | | |185| | | | |190| | |
|Ile|Met|Ala|Pro|Pro|Phe|Trp|Arg|Met|Ala|Leu|Arg|Gly|Asn|Gly|Leu|
| | |195| | | | |200| | | | |205| | | |
|Ala|Asp|Asp|Val|Pro|Val|Asp|Arg|Trp|Gln|Ile|Cys|Arg|Phe|Thr|Pro|
| |210| | | | |215| | | | |220| | | | |
|Pro|Ser|His|Val|Leu|Ile|Glu|Val|Gly|Val|Ala|His|Ala|Gly|Lys|Gly|
|225| | | | |230| | | | |235| | | | |240|
|Gly|Tyr|His|Ala|Glu|Ala|Gln|His|Lys|Ala|Ser|Ser|Ile|Val|Val|Asp|
| | | | |245| | | | |250| | | | |255| |
|Phe|Ile|Thr|Pro|Glu|Ser|Asp|Thr|Ser|Ile|Trp|Tyr|Phe|Trp|Gly|Met|
| | | |260| | | | |265| | | | |270| | |
|Ala|Arg|Asn|Phe|Ala|Ala|His|Asp|Gln|Thr|Leu|Thr|Asp|Asn|Ile|Arg|
| | |275| | | | |280| | | | |285| | | |
|Glu|Gly|Gln|Gly|Lys|Ile|Phe|Ser|Gly|Asp|Leu|Glu|Met|Leu|Glu|Arg|
| |290| | | | |295| | | | |300| | | | |
|Gln|Gln|Gln|Asn|Leu|Leu|Ala|His|Pro|Glu|Arg|Asn|Leu|Leu|Lys|Leu|
|305| | | | |310| | | | |315| | | | |320|
|Asn|Ile|Asp|Ala|Gly|Gly|Val|Gln|Ser|Arg|Lys|Val|Leu|Glu|Arg|Ile|
| | | | |325| | | | |330| | | | |335| |
|Ile|Ala|Gln|Glu|Arg|Ala|Pro|Gln|Pro|Gln|Leu|Ile|Ala|Thr|Ser|Ala|
| | | |340| | | | |345| | | | |350| | |
|Asn|Pro|Ala| | | | | | | | | | | | | |
| | |355| | | | | | | | | | | | | |

```
<210> SEQ ID NO 7
<211> LENGTH: 951
<212> TYPE: DNA
<213> ORGANISM: Pseudomonas putida
<220> FEATURE:
<221> NAME/KEY: CDS
<222> LOCATION: (1)..(951)
```

<400> SEQUENCE: 7

```
atg atc gat gcc gta gtg gta tcc cgt aac gat gaa gcg cag ggt atc         48
Met Ile Asp Ala Val Val Val Ser Arg Asn Asp Glu Ala Gln Gly Ile
1               5                   10                  15 tgc agc ttc gag ctg gcc gcg gca gat ggc agc ctg ctg ccg gcg ttc         96
Cys Ser Phe Glu Leu Ala Ala Ala Asp Gly Ser Leu Leu Pro Ala Phe
            20                  25                  30 agc gcc ggc gcc cat atc gac gtg cac ctg ccc gac ggg ctg gtg cgc        144
Ser Ala Gly Ala His Ile Asp Val His Leu Pro Asp Gly Leu Val Arg
        35                  40                  45 cag tat tcg ctg tgc aac cac ccc gaa gaa cgc cat cgc tat ctg att        192
Gln Tyr Ser Leu Cys Asn His Pro Glu Glu Arg His Arg Tyr Leu Ile
    50                  55                  60 ggc gta ctc aac gac ccg gct tcg cgg ggc ggt tct cgt agc ctg cac        240
Gly Val Leu Asn Asp Pro Ala Ser Arg Gly Gly Ser Arg Ser Leu His
65                  70                  75                  80 gaa cag gtg caa gcc ggt gcc cgg ctg cgt atc agt gcg ccg cgc aac        288
Glu Gln Val Gln Ala Gly Ala Arg Leu Arg Ile Ser Ala Pro Arg Asn
                85                  90                  95 ctg ttc ccg ctg gcc gag ggt gcg cag cgc agt ttg ctg ttt gct ggc        336
Leu Phe Pro Leu Ala Glu Gly Ala Gln Arg Ser Leu Leu Phe Ala Gly
            100                 105                 110 ggt atc ggc att acc cca atc ctg tgc atg gcc gag cag ctg tcc gac        384
Gly Ile Gly Ile Thr Pro Ile Leu Cys Met Ala Glu Gln Leu Ser Asp
        115                 120                 125 agc ggc cag gcc ttc gag ctg cac tac tgt gcc cgc tcc agc gag cgt        432
Ser Gly Gln Ala Phe Glu Leu His Tyr Cys Ala Arg Ser Ser Glu Arg
    130                 135                 140 gcg gcg ttt gtc gag cgg atc cgc agc gcg ccg ttc gct gat cgg ctg        480
Ala Ala Phe Val Glu Arg Ile Arg Ser Ala Pro Phe Ala Asp Arg Leu
145                 150                 155                 160 ttc gtg cat ttt gac gag cag ccg gaa acg gcg ctg gac atc gcc cag        528
Phe Val His Phe Asp Glu Gln Pro Glu Thr Ala Leu Asp Ile Ala Gln
                165                 170                 175 gtg ctg ggc aac ccg caa gat gat gtg cac ctg tat gta tgc ggg ccc        576
Val Leu Gly Asn Pro Gln Asp Asp Val His Leu Tyr Val Cys Gly Pro
            180                 185                 190 ggc ggg ttc atg cag cat gtg ctg gac agc gcg aag ggg ctg ggc tgg        624
Gly Gly Phe Met Gln His Val Leu Asp Ser Ala Lys Gly Leu Gly Trp
        195                 200                 205 cag gag gcc aac ctg cac cgc gag tac ttc gcc gca gca ccg gtg gat        672
Gln Glu Ala Asn Leu His Arg Glu Tyr Phe Ala Ala Ala Pro Val Asp
    210                 215                 220 gcc agc aac gat ggc agt ttc gcg gtg cag gtg ggc agc acg gga cag        720
Ala Ser Asn Asp Gly Ser Phe Ala Val Gln Val Gly Ser Thr Gly Gln
225                 230                 235                 240 gtg ttc gag gtg cca gcc gac cgg acc gtg gtg cag gtg ctg gaa gag        768
Val Phe Glu Val Pro Ala Asp Arg Thr Val Val Gln Val Leu Glu Glu
                245                 250                 255 aat ggt atc gag atc gcc atg tcg tgc gag cag ggt att tgc ggc acc        816
Asn Gly Ile Glu Ile Ala Met Ser Cys Glu Gln Gly Ile Cys Gly Thr
            260                 265                 270 tgc ctg aca cgc gtg ctg cag ggc aca ccg gac cat cgc gat ctg ttt        864
Cys Leu Thr Arg Val Leu Gln Gly Thr Pro Asp His Arg Asp Leu Phe
        275                 280                 285 ctc acc gaa gag gaa cag gcc ctg aac gat cag ttc acg ccc tgc tgc        912
Leu Thr Glu Glu Glu Gln Ala Leu Asn Asp Gln Phe Thr Pro Cys Cys
    290                 295                 300
```

```
tcg cgc tcg aag acg ccg ctg ctg gtg ctg gac atc tga                951
Ser Arg Ser Lys Thr Pro Leu Leu Val Leu Asp Ile
305             310                 315

<210> SEQ ID NO 8
<211> LENGTH: 316
<212> TYPE: PRT
<213> ORGANISM: Pseudomonas putida

<400> SEQUENCE: 8

Met Ile Asp Ala Val Val Ser Arg Asn Asp Glu Ala Gln Gly Ile
1               5                   10                  15

Cys Ser Phe Glu Leu Ala Ala Ala Asp Gly Ser Leu Leu Pro Ala Phe
                20                  25                  30

Ser Ala Gly Ala His Ile Asp Val His Leu Pro Asp Gly Leu Val Arg
            35                  40                  45

Gln Tyr Ser Leu Cys Asn His Pro Glu Glu Arg His Arg Tyr Leu Ile
    50                  55                  60

Gly Val Leu Asn Asp Pro Ala Ser Arg Gly Gly Ser Arg Ser Leu His
65                  70                  75                  80

Glu Gln Val Gln Ala Gly Ala Arg Leu Arg Ile Ser Ala Pro Arg Asn
                85                  90                  95

Leu Phe Pro Leu Ala Glu Gly Ala Gln Arg Ser Leu Leu Phe Ala Gly
                100                 105                 110

Gly Ile Gly Ile Thr Pro Ile Leu Cys Met Ala Glu Gln Leu Ser Asp
            115                 120                 125

Ser Gly Gln Ala Phe Glu Leu His Tyr Cys Ala Arg Ser Ser Glu Arg
    130                 135                 140

Ala Ala Phe Val Glu Arg Ile Arg Ser Ala Pro Phe Ala Asp Arg Leu
145                 150                 155                 160

Phe Val His Phe Asp Glu Gln Pro Glu Thr Ala Leu Asp Ile Ala Gln
                165                 170                 175

Val Leu Gly Asn Pro Gln Asp Asp Val His Leu Tyr Val Cys Gly Pro
                180                 185                 190

Gly Gly Phe Met Gln His Val Leu Asp Ser Ala Lys Gly Leu Gly Trp
            195                 200                 205

Gln Glu Ala Asn Leu His Arg Glu Tyr Phe Ala Ala Pro Val Asp
    210                 215                 220

Ala Ser Asn Asp Gly Ser Phe Ala Val Gln Val Gly Ser Thr Gly Gln
225                 230                 235                 240

Val Phe Glu Val Pro Ala Asp Arg Thr Val Gln Val Leu Glu Glu
                245                 250                 255

Asn Gly Ile Glu Ile Ala Met Ser Cys Glu Gln Gly Ile Cys Gly Thr
                260                 265                 270

Cys Leu Thr Arg Val Leu Gln Gly Thr Pro Asp His Arg Asp Leu Phe
            275                 280                 285

Leu Thr Glu Glu Glu Gln Ala Leu Asn Asp Gln Phe Thr Pro Cys Cys
    290                 295                 300

Ser Arg Ser Lys Thr Pro Leu Leu Val Leu Asp Ile
305                 310                 315

<210> SEQ ID NO 9
<211> LENGTH: 720
<212> TYPE: DNA
<213> ORGANISM: Pseudomonas putida
<220> FEATURE:
<221> NAME/KEY: CDS
```

<222> LOCATION: (1)..(720)

<400> SEQUENCE: 9

```
atg ccc gcc cag gac aac agc cgc ttc gtg atc cgt gat cgc aac tgg      48
Met Pro Ala Gln Asp Asn Ser Arg Phe Val Ile Arg Asp Arg Asn Trp
1               5                   10                  15 cac cct aaa gcc ctt acg cct gac tac aag acc tcc gtt gcc cgc tcg      96
His Pro Lys Ala Leu Thr Pro Asp Tyr Lys Thr Ser Val Ala Arg Ser
            20                  25                  30 ccg cgc cag gca ctg gtc agc att ccg cag tcg atc agc gaa acc act     144
Pro Arg Gln Ala Leu Val Ser Ile Pro Gln Ser Ile Ser Glu Thr Thr
        35                  40                  45 ggt ccg gac ttt tcc cat ctg ggc ttc ggc gcc cac gac cat gac ctg     192
Gly Pro Asp Phe Ser His Leu Gly Phe Gly Ala His Asp His Asp Leu
    50                  55                  60 ctg ctg aac ttc aat aac ggt ggc ctg ccc att ggc gag cgc atc atc     240
Leu Leu Asn Phe Asn Asn Gly Gly Leu Pro Ile Gly Glu Arg Ile Ile
65                  70                  75                  80 gtc gcc ggc cgt gtc gtc gac cag tac ggc aag cct gtg ccg aac act     288
Val Ala Gly Arg Val Val Asp Gln Tyr Gly Lys Pro Val Pro Asn Thr
                85                  90                  95 ttg gtg gag atg tgg caa gcc aac gcc ggc ggc cgc tat cgc cac aag     336
Leu Val Glu Met Trp Gln Ala Asn Ala Gly Gly Arg Tyr Arg His Lys
            100                 105                 110 aac gat cgc tac ctg gcg ccc ctg gac ccg aac ttc ggt ggt gtt ggg     384
Asn Asp Arg Tyr Leu Ala Pro Leu Asp Pro Asn Phe Gly Gly Val Gly
        115                 120                 125 cgg tgt ctg acc gac cgt gac ggc tat tac agc ttc cgc acc atc aag     432
Arg Cys Leu Thr Asp Arg Asp Gly Tyr Tyr Ser Phe Arg Thr Ile Lys
    130                 135                 140 ccg ggc ccg tac cca tgg cgc aac ggc ccg aac gac tgg cgc ccg gcg     480
Pro Gly Pro Tyr Pro Trp Arg Asn Gly Pro Asn Asp Trp Arg Pro Ala
145                 150                 155                 160 cat atc cac ttc gcc atc agc ggc cca tcg atc gcc acc aag ctg atc     528
His Ile His Phe Ala Ile Ser Gly Pro Ser Ile Ala Thr Lys Leu Ile
                165                 170                 175 acc cag ttg tac ttc gaa ggt gac ccg ctg atc ccg atg tgc ccg atc     576
Thr Gln Leu Tyr Phe Glu Gly Asp Pro Leu Ile Pro Met Cys Pro Ile
            180                 185                 190 gtc aag tcg atc gcc aac ccg caa gcc gtg cag cag ttg atc gcc aag     624
Val Lys Ser Ile Ala Asn Pro Gln Ala Val Gln Gln Leu Ile Ala Lys
        195                 200                 205 ctc gac atg agc aac gcc aac ccg atg gac tgc ctg gcc tac cgc ttt     672
Leu Asp Met Ser Asn Ala Asn Pro Met Asp Cys Leu Ala Tyr Arg Phe
    210                 215                 220 gac atc gtg ctg cgc ggc cag cgc aag acc cac ttc gaa aac tgc tga     720
Asp Ile Val Leu Arg Gly Gln Arg Lys Thr His Phe Glu Asn Cys
225                 230                 235
```

<210> SEQ ID NO 10
<211> LENGTH: 239
<212> TYPE: PRT
<213> ORGANISM: Pseudomonas putida

<400> SEQUENCE: 10

```
Met Pro Ala Gln Asp Asn Ser Arg Phe Val Ile Arg Asp Arg Asn Trp
1               5                   10                  15

His Pro Lys Ala Leu Thr Pro Asp Tyr Lys Thr Ser Val Ala Arg Ser
            20                  25                  30

Pro Arg Gln Ala Leu Val Ser Ile Pro Gln Ser Ile Ser Glu Thr Thr
```

```
                35                  40                  45
Gly Pro Asp Phe Ser His Leu Gly Phe Gly Ala His Asp His Asp Leu
         50                  55                  60

Leu Leu Asn Phe Asn Asn Gly Gly Leu Pro Ile Gly Glu Arg Ile Ile
 65                  70                  75                  80

Val Ala Gly Arg Val Val Asp Gln Tyr Gly Lys Pro Val Pro Asn Thr
                 85                  90                  95

Leu Val Glu Met Trp Gln Ala Asn Ala Gly Gly Arg Tyr Arg His Lys
            100                 105                 110

Asn Asp Arg Tyr Leu Ala Pro Leu Asp Pro Asn Phe Gly Gly Val Gly
        115                 120                 125

Arg Cys Leu Thr Asp Arg Asp Gly Tyr Tyr Ser Phe Arg Thr Ile Lys
    130                 135                 140

Pro Gly Pro Tyr Pro Trp Arg Asn Gly Pro Asn Asp Trp Arg Pro Ala
145                 150                 155                 160

His Ile His Phe Ala Ile Ser Gly Pro Ser Ile Ala Thr Lys Leu Ile
                165                 170                 175

Thr Gln Leu Tyr Phe Glu Gly Asp Pro Leu Ile Pro Met Cys Pro Ile
            180                 185                 190

Val Lys Ser Ile Ala Asn Pro Gln Ala Val Gln Leu Ile Ala Lys
        195                 200                 205

Leu Asp Met Ser Asn Ala Asn Pro Met Asp Cys Leu Ala Tyr Arg Phe
    210                 215                 220

Asp Ile Val Leu Arg Gly Gln Arg Lys Thr His Phe Glu Asn Cys
225                 230                 235

<210> SEQ ID NO 11
<211> LENGTH: 720
<212> TYPE: DNA
<213> ORGANISM: Pseudomonas putida
<220> FEATURE:
<221> NAME/KEY: CDS
<222> LOCATION: (1)..(720)

<400> SEQUENCE: 11 atg ccc gcc cag gac aac agc cgc ttc gtg atc cgt gat cgc aac tgg      48
Met Pro Ala Gln Asp Asn Ser Arg Phe Val Ile Arg Asp Arg Asn Trp
  1               5                  10                  15 cac cct aaa gcc ctt acg cct gac tac aag acc tcc gtt gcc cgc tcg      96
His Pro Lys Ala Leu Thr Pro Asp Tyr Lys Thr Ser Val Ala Arg Ser
             20                  25                  30 ccg cgc cag gca ctg gtc agc att ccg cag tcg atc agc gaa acc act     144
Pro Arg Gln Ala Leu Val Ser Ile Pro Gln Ser Ile Ser Glu Thr Thr
         35                  40                  45 ggt ccg gac ttt tcc cat ctg ggc ttc ggc gcc cac gac cat gac ctg     192
Gly Pro Asp Phe Ser His Leu Gly Phe Gly Ala His Asp His Asp Leu
     50                  55                  60 ctg ctg aac ttc aat aac ggt ggc ctg ccc att ggc gag cgc atc atc     240
Leu Leu Asn Phe Asn Asn Gly Gly Leu Pro Ile Gly Glu Arg Ile Ile
 65                  70                  75                  80 gtc gcc ggc cgt gtc gtc gac cag tac ggc aag cct gtg ccg aac act     288
Val Ala Gly Arg Val Val Asp Gln Tyr Gly Lys Pro Val Pro Asn Thr
                 85                  90                  95 ttg gtg gag atg tgg caa gcc aac gcc ggc ggc cgt tat cgc cac aag     336
Leu Val Glu Met Trp Gln Ala Asn Ala Gly Gly Arg Tyr Arg His Lys
            100                 105                 110 aac gat cgc tac ctg gcg ccc ctg gac ccg aac ttc ggt ggt gtt ggg     384
Asn Asp Arg Tyr Leu Ala Pro Leu Asp Pro Asn Phe Gly Gly Val Gly
```

```
                   115                 120                 125
cgg tgt ctg acc gac cgt gac ggc tat tac agc ttc cgc acc atc aag    432
Arg Cys Leu Thr Asp Arg Asp Gly Tyr Tyr Ser Phe Arg Thr Ile Lys
    130                 135                 140 ccg ggc ccg tac cca tgg cgc aac ggc ccg aac gac tgg cgc ccg gcg    480
Pro Gly Pro Tyr Pro Trp Arg Asn Gly Pro Asn Asp Trp Arg Pro Ala
145                 150                 155                 160 cat atc cac ttc gcc atc agc ggc cca tcg atc gcc acc aag ctg atc    528
His Ile His Phe Ala Ile Ser Gly Pro Ser Ile Ala Thr Lys Leu Ile
                165                 170                 175 acc cag ttg tac ttc gaa ggt gac ccg ctg atc ccg atg tgc ccg atc    576
Thr Gln Leu Tyr Phe Glu Gly Asp Pro Leu Ile Pro Met Cys Pro Ile
            180                 185                 190 gtc aag tcg atc gcc aac ccg caa gcc gtg cag cag ttg atc gcc aag    624
Val Lys Ser Ile Ala Asn Pro Gln Ala Val Gln Gln Leu Ile Ala Lys
        195                 200                 205 ctc gac atg agc aac gcc aac ccg atg gac tgc ctg gcc tac cgc ttt    672
Leu Asp Met Ser Asn Ala Asn Pro Met Asp Cys Leu Ala Tyr Arg Phe
    210                 215                 220 gac atc gtg ctg cgc ggc cag cgc aag acc cac ttc gaa aac tgc tga    720
Asp Ile Val Leu Arg Gly Gln Arg Lys Thr His Phe Glu Asn Cys
225                 230                 235

<210> SEQ ID NO 12
<211> LENGTH: 239
<212> TYPE: PRT
<213> ORGANISM: Pseudomonas putida

<400> SEQUENCE: 12

Met Pro Ala Gln Asp Asn Ser Arg Phe Val Ile Arg Asp Arg Asn Trp
1               5                   10                  15

His Pro Lys Ala Leu Thr Pro Asp Tyr Lys Thr Ser Val Ala Arg Ser
            20                  25                  30

Pro Arg Gln Ala Leu Val Ser Ile Pro Gln Ser Ile Ser Glu Thr Thr
        35                  40                  45

Gly Pro Asp Phe Ser His Leu Gly Phe Gly Ala His Asp His Asp Leu
    50                  55                  60

Leu Leu Asn Phe Asn Asn Gly Gly Leu Pro Ile Gly Glu Arg Ile Ile
65                  70                  75                  80

Val Ala Gly Arg Val Asp Gln Tyr Gly Lys Pro Val Pro Asn Thr
                85                  90                  95

Leu Val Glu Met Trp Gln Ala Asn Ala Gly Gly Arg Tyr Arg His Lys
            100                 105                 110

Asn Asp Arg Tyr Leu Ala Pro Leu Asp Pro Asn Phe Gly Gly Val Gly
        115                 120                 125

Arg Cys Leu Thr Asp Arg Asp Gly Tyr Tyr Ser Phe Arg Thr Ile Lys
    130                 135                 140

Pro Gly Pro Tyr Pro Trp Arg Asn Gly Pro Asn Asp Trp Arg Pro Ala
145                 150                 155                 160

His Ile His Phe Ala Ile Ser Gly Pro Ser Ile Ala Thr Lys Leu Ile
                165                 170                 175

Thr Gln Leu Tyr Phe Glu Gly Asp Pro Leu Ile Pro Met Cys Pro Ile
            180                 185                 190

Val Lys Ser Ile Ala Asn Pro Gln Ala Val Gln Gln Leu Ile Ala Lys
        195                 200                 205

Leu Asp Met Ser Asn Ala Asn Pro Met Asp Cys Leu Ala Tyr Arg Phe
    210                 215                 220
```

```
Asp Ile Val Leu Arg Gly Gln Arg Lys Thr His Phe Glu Asn Cys
225                 230                 235
```

<210> SEQ ID NO 13
<211> LENGTH: 780
<212> TYPE: DNA
<213> ORGANISM: Pseudomonas putida
<220> FEATURE:
<221> NAME/KEY: CDS
<222> LOCATION: (1)..(780)

<400> SEQUENCE: 13

```
atg cgg atc atc agt gtg aac gta aat ggc att cag gct gcg gcc gag      48
Met Arg Ile Ile Ser Val Asn Val Asn Gly Ile Gln Ala Ala Ala Glu
1               5                   10                  15 cgt ggt ttg ctc agc tgg ctg caa gcc cag aat gcc gac gtc atc tgc      96
Arg Gly Leu Leu Ser Trp Leu Gln Ala Gln Asn Ala Asp Val Ile Cys
                20                  25                  30 ctt cag gat acc cgc gcc tcg gcc ttt gaa ctc gac gac cca gct ttc     144
Leu Gln Asp Thr Arg Ala Ser Ala Phe Glu Leu Asp Asp Pro Ala Phe
            35                  40                  45 cag ctc gat ggc tat ttc ctt tat gcc tgc gac gcg gag gtg cct gcc     192
Gln Leu Asp Gly Tyr Phe Leu Tyr Ala Cys Asp Ala Glu Val Pro Ala
        50                  55                  60 caa ggt ggt gtg gcc ctt tac tcg cgc atg cag ccc aag gca gtc atc     240
Gln Gly Gly Val Ala Leu Tyr Ser Arg Met Gln Pro Lys Ala Val Ile
65                  70                  75                  80 acc ggc ctg ggc ttc gag aca gcc gac cgc tac ggg cgt tac ctg caa     288
Thr Gly Leu Gly Phe Glu Thr Ala Asp Arg Tyr Gly Arg Tyr Leu Gln
                85                  90                  95 gca gat ttc gac aaa gtc agt att gcc agc ctg ctg ctg cct tcg ggc     336
Ala Asp Phe Asp Lys Val Ser Ile Ala Ser Leu Leu Leu Pro Ser Gly
            100                 105                 110 atg aac ggc gac gaa gac ttg aat cag aaa ttc aag ttg atg gac gac     384
Met Asn Gly Asp Glu Asp Leu Asn Gln Lys Phe Lys Leu Met Asp Asp
        115                 120                 125 ttc gcc aag tac ctg gac aag cag cgt cgc aag cgt gcc gaa tac atc     432
Phe Ala Lys Tyr Leu Asp Lys Gln Arg Arg Lys Arg Arg Glu Tyr Ile
    130                 135                 140 tat tgc ggc tcg ttc tac gtg gcg cag cag aag ctc gac atc aag aat     480
Tyr Cys Gly Ser Phe Tyr Val Ala Gln Gln Lys Leu Asp Ile Lys Asn
145                 150                 155                 160 tgg cgt gac agc cag cag tcg ccg ggc ttc ctg gcg cca gaa cgc gcc     528
Trp Arg Asp Ser Gln Gln Ser Pro Gly Phe Leu Ala Pro Glu Arg Ala
                165                 170                 175 tgg atg gat gcg atc act ggc gag atg ggg tat gtc gat gcc ttg cgc     576
Trp Met Asp Ala Ile Thr Gly Glu Met Gly Tyr Val Asp Ala Leu Arg
            180                 185                 190 gaa gtc agc cgt gaa ggc gac cag tac agc tgg tgg ccg gac aac gag     624
Glu Val Ser Arg Glu Gly Asp Gln Tyr Ser Trp Trp Pro Asp Asn Glu
        195                 200                 205 cag gcc gag atg ctc aac ctg ggg tat cgg ttc gac tac cag atc ctc     672
Gln Ala Glu Met Leu Asn Leu Gly Tyr Arg Phe Asp Tyr Gln Ile Leu
    210                 215                 220 acc ccg ggc ctg cgc cgc ttc gtg cgc aac gct cgc ctg ccg cgt cag     720
Thr Pro Gly Leu Arg Arg Phe Val Arg Asn Ala Arg Leu Pro Arg Gln
225                 230                 235                 240 cca cgc ttc tcc cag cat gca ccg ctg atc gtc gac tat gac tgg acg     768
Pro Arg Phe Ser Gln His Ala Pro Leu Ile Val Asp Tyr Asp Trp Thr
                245                 250                 255
```

```
ctg acc atc taa                                                          780
Leu Thr Ile
```

<210> SEQ ID NO 14
<211> LENGTH: 259
<212> TYPE: PRT
<213> ORGANISM: Pseudomonas putida

<400> SEQUENCE: 14

```
Met Arg Ile Ile Ser Val Asn Val Asn Gly Ile Gln Ala Ala Ala Glu
1               5                   10                  15

Arg Gly Leu Leu Ser Trp Leu Gln Ala Gln Asn Ala Asp Val Ile Cys
            20                  25                  30

Leu Gln Asp Thr Arg Ala Ser Ala Phe Glu Leu Asp Asp Pro Ala Phe
        35                  40                  45

Gln Leu Asp Gly Tyr Phe Leu Tyr Ala Cys Asp Ala Glu Val Pro Ala
    50                  55                  60

Gln Gly Gly Val Ala Leu Tyr Ser Arg Met Gln Pro Lys Ala Val Ile
65                  70                  75                  80

Thr Gly Leu Gly Phe Glu Thr Ala Asp Arg Tyr Gly Arg Tyr Leu Gln
                85                  90                  95

Ala Asp Phe Asp Lys Val Ser Ile Ala Ser Leu Leu Leu Pro Ser Gly
            100                 105                 110

Met Asn Gly Asp Glu Asp Leu Asn Gln Lys Phe Lys Leu Met Asp Asp
        115                 120                 125

Phe Ala Lys Tyr Leu Asp Lys Gln Arg Arg Lys Arg Arg Glu Tyr Ile
    130                 135                 140

Tyr Cys Gly Ser Phe Tyr Val Ala Gln Gln Lys Leu Asp Ile Lys Asn
145                 150                 155                 160

Trp Arg Asp Ser Gln Gln Ser Pro Gly Phe Leu Ala Pro Glu Arg Ala
                165                 170                 175

Trp Met Asp Ala Ile Thr Gly Glu Met Gly Tyr Val Asp Ala Leu Arg
            180                 185                 190

Glu Val Ser Arg Glu Gly Asp Gln Tyr Ser Trp Trp Pro Asp Asn Glu
        195                 200                 205

Gln Ala Glu Met Leu Asn Leu Gly Tyr Arg Phe Asp Tyr Gln Ile Leu
    210                 215                 220

Thr Pro Gly Leu Arg Arg Phe Val Arg Asn Ala Arg Leu Pro Arg Gln
225                 230                 235                 240

Pro Arg Phe Ser Gln His Ala Pro Leu Ile Val Asp Tyr Asp Trp Thr
                245                 250                 255

Leu Thr Ile
```

<210> SEQ ID NO 15
<211> LENGTH: 720
<212> TYPE: DNA
<213> ORGANISM: Bacillus cereus
<220> FEATURE:
<221> NAME/

```
ccg cgc cag gca ctg gtc agc att ccg cag tcg atc agc gaa acc act    144
Pro Arg Gln Ala Leu Val Ser Ile Pro Gln Ser Ile Ser Glu Thr Thr
         35                  40                  45 ggt ccg gac ttt tcc cat ctg ggc ttc ggc gcc cac gac cat gac ctg    192
Gly Pro Asp Phe Ser His Leu Gly Phe Gly Ala His Asp His Asp Leu
 50                  55                  60 ctg ctg aac ttc aat aac ggt ggc ctg ccc att ggc gag cgc atc atc    240
Leu Leu Asn Phe Asn Asn Gly Gly Leu Pro Ile Gly Glu Arg Ile Ile
65                  70                  75                  80 gtc gcc ggc cgt gtc gtc gac cag tac ggc aag cct gtg ccg aac act    288
Val Ala Gly Arg Val Val Asp Gln Tyr Gly Lys Pro Val Pro Asn Thr
                 85                  90                  95 ttg gtg gag atg tgg caa gcc aac gcc ggc ggc cgt tat cgc cac aag    336
Leu Val Glu Met Trp Gln Ala Asn Ala Gly Gly Arg Tyr Arg His Lys
            100                 105                 110 aac gat cgc tac ctg gcg ccc ctg gac ccg aac ttc ggt ggt gtt ggg    384
Asn Asp Arg Tyr Leu Ala Pro Leu Asp Pro Asn Phe Gly Gly Val Gly
        115                 120                 125 cgg tgt ctg acc gac cgt gac ggc tat tac agc ttc cgc acc atc aag    432
Arg Cys Leu Thr Asp Arg Asp Gly Tyr Tyr Ser Phe Arg Thr Ile Lys
    130                 135                 140 ccg ggc ccg tac cca tgg cgc aac ggc ccg aac gac tgg cgc ccg gcg    480
Pro Gly Pro Tyr Pro Trp Arg Asn Gly Pro Asn Asp Trp Arg Pro Ala
145                 150                 155                 160 cat atc cac ttc gcc atc agc ggc cca tcg atc gcc acc aag ctg atc    528
His Ile His Phe Ala Ile Ser Gly Pro Ser Ile Ala Thr Lys Leu Ile
                165                 170                 175 acc cag ttg tac ttc gaa ggt gac ccg ctg atc ccg atg tgc ccg atc    576
Thr Gln Leu Tyr Phe Glu Gly Asp Pro Leu Ile Pro Met Cys Pro Ile
            180                 185                 190 gtc aag tcg atc gcc aac ccg caa gcc gtg cag cag ttg atc gcc aag    624
Val Lys Ser Ile Ala Asn Pro Gln Ala Val Gln Gln Leu Ile Ala Lys
        195                 200                 205 ctc gac atg agc aac gcc aac ccg atg gac tgc ctg gcc tac cgc ttt    672
Leu Asp Met Ser Asn Ala Asn Pro Met Asp Cys Leu Ala Tyr Arg Phe
210                 215                 220 gac atc gtg ctg cgc ggc cag cgc aag acc cac ttc gaa aac tgc tga    720
Asp Ile Val Leu Arg Gly Gln Arg Lys Thr His Phe Glu Asn Cys
225                 230                 235
```

<210> SEQ ID NO 16
<211> LENGTH: 239
<212> TYPE: PRT
<213> ORGANISM: Bacillus cereus

<400> S

```
Leu Val Glu Met Trp Gln Ala Asn Ala Gly Gly Arg Tyr Arg His Lys
            100                 105                 110

Asn Asp Arg Tyr Leu Ala Pro Leu Asp Pro Asn Phe Gly Gly Val Gly
        115                 120                 125

Arg Cys Leu Thr Asp Arg Asp Gly Tyr Tyr Ser Phe Arg Thr Ile Lys
    130                 135                 140

Pro Gly Pro Tyr Pro Trp Arg Asn Gly Pro Asn Asp Trp Arg Pro Ala
145                 150                 155                 160

His Ile His Phe Ala Ile Ser Gly Pro Ser Ile Ala Thr Lys Leu Ile
                165                 170                 175

Thr Gln Leu Tyr Phe Glu Gly Asp Pro Leu Ile Pro Met Cys Pro Ile
            180                 185                 190

Val Lys Ser Ile Ala Asn Pro Gln Ala Val Gln Gln Leu Ile Ala Lys
        195                 200                 205

Leu Asp Met Ser Asn Ala Asn Pro Met Asp Cys Leu Ala Tyr Arg Phe
    210                 215                 220

Asp Ile Val Leu Arg Gly Gln Arg Lys Thr His Phe Glu Asn Cys
225                 230                 235

<210> SEQ ID NO 17
<211> LENGTH: 1488
<212> TYPE: DNA
<213> ORGANISM: Enterobacter cloacae
<220> FEATURE:
<221> NAME/KEY: CDS
<222> LOCATION: (1)..(1488)

<400> SEQUENCE: 17 atg cag aac ccg atc aac gac ctg cgc tcc gcg atc gcg ctg ctg caa      48
Met Gln Asn Pro Ile Asn Asp Leu Arg Ser Ala Ile Ala Leu Leu Gln
1               5                   10                  15 cgc cat ccg ggt cac tac atc gaa acc gac cac ccg gtc gac ccg aac      96
Arg His Pro Gly His Tyr Ile Glu Thr Asp His Pro Val Asp Pro Asn
            20                  25                  30 gcc gaa ctg gcc ggt gtg tac cgc cac atc ggt gcg ggt ggc acc gtg     144
Ala Glu Leu Ala Gly Val Tyr Arg His Ile Gly Ala Gly Gly Thr Val
        35                  40                  45 aaa cgt ccg acc cgc acc ggt cca gcc atg atg ttc aac agc gtg aag     192
Lys Arg Pro Thr Arg Thr Gly Pro Ala Met Met Phe Asn Ser Val Lys
    50                  55                  60 ggc tac cca ggc agc cgc atc ctg gtg ggc atg cac gcc agc cgt gaa     240
Gly Tyr Pro Gly Ser Arg Ile Leu Val Gly Met His Ala Ser Arg Glu
65                  70                  75                  80 cgt gcc gcc ctg ctg ctg ggc tgc gtg cca agc aaa ctg gcg cag cac     288
Arg Ala Ala Leu Leu Leu Gly Cys Val Pro Ser Lys Leu Ala Gln His
                85                  90                  95 gtg ggc cag gcc gtg aag aac ccg gtg gcc cca gtg gtg gtg cca gcc     336
Val Gly Gln Ala Val Lys Asn Pro Val Ala Pro Val Val Val Pro Ala
            100                 105                 110 agc caa gcc cca tgc caa gaa cag gtg ttc tac gcc gac gac ccg gac     384
Ser Gln Ala Pro Cys Gln Glu Gln Val Phe Tyr Ala Asp Asp Pro Asp
        115                 120                 125 ttc gac ctg cgc aag ctg ctg cca gcc cca acc aac acc ccg atc gat     432
Phe Asp Leu Arg Lys Leu Leu Pro Ala Pro Thr Asn Thr Pro Ile Asp
    130                 135                 140 gcc ggt ccg ttc ttc tgc ctg ggc ctg gtg ctg gcg agc gac ccg gaa     480
Ala Gly Pro Phe Phe Cys Leu Gly Leu Val Leu Ala Ser Asp Pro Glu
145                 150                 155                 160 gat acc agc ctg acc gac gtg acc atc cac cgc ctg tgc gtg caa gag     528
```

```
            Asp Thr Ser Leu Thr Asp Val Thr Ile His Arg Leu Cys Val Gln Glu
                    165                 170                 175 cgc gac gag ctg agc atg ttc ctg gcc gcc ggt cgc cac atc gag gtg        576
Arg Asp Glu Leu Ser Met Phe Leu Ala Ala Gly Arg His Ile Glu Val
            180                 185                 190 ttc cgc aag aag gcc gaa gcc gcc ggt aag ccg ctg ccg gtg acc atc        624
Phe Arg Lys Lys Ala Glu Ala Ala Gly Lys Pro Leu Pro Val Thr Ile
        195                 200                 205 aac atg ggc ctg gac cca gcc atc tac atc ggt gcc tgc ttc gaa gcg        672
Asn Met Gly Leu Asp Pro Ala Ile Tyr Ile Gly Ala Cys Phe Glu Ala
    210                 215                 220 cca acc acc ccg ttc ggc tac aac gag ctg ggt gtg gcc ggt gcc ctg        720
Pro Thr Thr Pro Phe Gly Tyr Asn Glu Leu Gly Val Ala Gly Ala Leu
225                 230                 235                 240 cgt cag caa ccg gtg gaa ctg gtg cag ggc gtg gcc gtg aaa gag aag        768
Arg Gln Gln Pro Val Glu Leu Val Gln Gly Val Ala Val Lys Glu Lys
                245                 250                 255 gcg atc gcg cgt gcc gag atc atc atc gag ggc gaa ctg ctg cca ggc        816
Ala Ile Ala Arg Ala Glu Ile Ile Ile Glu Gly Glu Leu Leu Pro Gly
            260                 265                 270 gtg cgc gtg cgc gaa gat cag cac acc aac acc ggt cac gcc atg ccg        864
Val Arg Val Arg Glu Asp Gln His Thr Asn Thr Gly His Ala Met Pro
        275                 280                 285 gaa ttc cca ggc tac tgc ggt gag gcc aac ccg agc ctg ccg gtg atc        912
Glu Phe Pro Gly Tyr Cys Gly Glu Ala Asn Pro Ser Leu Pro Val Ile
    290                 295                 300 aag gtg aag gcc gtg acc atg cgc aac cac gcc atc ctg cag acc ctg        960
Lys Val Lys Ala Val Thr Met Arg Asn His Ala Ile Leu Gln Thr Leu
305                 310                 315                 320 gtg ggt ccg ggt gag gaa cac acc acc ctg gcg ggt ctg ccg acc gaa       1008
Val Gly Pro Gly Glu Glu His Thr Thr Leu Ala Gly Leu Pro Thr Glu
                325                 330                 335 gcc agc atc cgc aac gcc gtg gaa gag gcg atc cca ggc ttc ctg cag       1056
Ala Ser Ile Arg Asn Ala Val Glu Glu Ala Ile Pro Gly Phe Leu Gln
            340                 345                 350 aac gtg tac gcc cac acc gcc ggt ggc ggt aag ttc ctg ggc atc ctg       1104
Asn Val Tyr Ala His Thr Ala Gly Gly Gly Lys Phe Leu Gly Ile Leu
        355                 360                 365 cag gtc aag aag cgc cag ccg agc gac gaa ggc cgt cag ggc caa gcc       1152
Gln Val Lys Lys Arg Gln Pro Ser Asp Glu Gly Arg Gln Gly Gln Ala
    370                 375                 380 gcc ctg atc gcc ctg gcc acc tac agc gag ctg aag aac atc atc ctg       1200
Ala Leu Ile Ala Leu Ala Thr Tyr Ser Glu Leu Lys Asn Ile Ile Leu
385                 390                 395                 400 gtg gac gag gac gtg gac atc ttc gac agc gac gac atc ctg tgg gcc       1248
Val Asp Glu Asp Val Asp Ile Phe Asp Ser Asp Asp Ile Leu Trp Ala
                405                 410                 415 atg acc acc cgc atg cag ggc gac gtg agc atc acc acc ctg cca ggc       1296
Met Thr Thr Arg Met Gln Gly Asp Val Ser Ile Thr Thr Leu Pro Gly
            420                 425                 430 atc cgt ggc cat cag ctg gac ccg agc cag agc cca gac tac agc acc       1344
Ile Arg Gly His Gln Leu Asp Pro Ser Gln Ser Pro Asp Tyr Ser Thr
        435                 440                 445 agc atc cgt ggc aac ggc atc agc tgc aag acc atc ttc gac tgc acc       1392
Ser Ile Arg Gly Asn Gly Ile Ser Cys Lys Thr Ile Phe Asp Cys Thr
    450                 455                 460 gtg ccg tgg gcc ctg aaa gcc cgt ttc gag cgt gcc cca ttc atg gaa       1440
Val Pro Trp Ala Leu Lys Ala Arg Phe Glu Arg Ala Pro Phe Met Glu
465                 470                 475                 480
```

```
gtg gac ccg acc ccg tgg gcc cca gag ctg ttc agc gac aag aag tga      1488
Val Asp Pro Thr Pro Trp Ala Pro Glu Leu Phe Ser Asp Lys Lys
                485                 490                 495

<210> SEQ ID NO 18
<211> LENGTH: 495
<212> TYPE: PRT
<213> ORGANISM: Enterobacter cloacae

<400> SEQUENCE: 18

Met Gln Asn Pro Ile Asn Asp Leu Arg Ser Ala Ile Ala Leu Leu Gln
 1               5                  10                  15

Arg His Pro Gly His Tyr Ile Glu Thr Asp His Pro Val Asp Pro Asn
            20                  25                  30

Ala Glu Leu Ala Gly Val Tyr Arg His Ile Gly Ala Gly Gly Thr Val
        35                  40                  45

Lys Arg Pro Thr Arg Thr Gly Pro Ala Met Met Phe Asn Ser Val Lys
    50                  55                  60

Gly Tyr Pro Gly Ser Arg Ile Leu Val Gly Met His Ala Ser Arg Glu
65                  70                  75                  80

Arg Ala Ala Leu Leu Leu Gly Cys Val Pro Ser Lys Leu Ala Gln His
                85                  90                  95

Val Gly Gln Ala Val Lys Asn Pro Val Ala Pro Val Val Pro Ala
            100                 105                 110

Ser Gln Ala Pro Cys Gln Glu Gln Val Phe Tyr Ala Asp Asp Pro Asp
        115                 120                 125

Phe Asp Leu Arg Lys Leu Leu Pro Ala Pro Thr Asn Thr Pro Ile Asp
    130                 135                 140

Ala Gly Pro Phe Phe Cys Leu Gly Leu Val Leu Ala Ser Asp Pro Glu
145                 150                 155                 160

Asp Thr Ser Leu Thr Asp Val Thr Ile His Arg Leu Cys Val Gln Glu
                165                 170                 175

Arg Asp Glu Leu Ser Met Phe Leu Ala Ala Gly Arg His Ile Glu Val
            180                 185                 190

Phe Arg Lys Lys Ala Glu Ala Ala Gly Lys Pro Leu Pro Val Thr Ile
        195                 200                 205

Asn Met Gly Leu Asp Pro Ala Ile Tyr Ile Gly Ala Cys Phe Glu Ala
    210                 215                 220

Pro Thr Thr Pro Phe Gly Tyr Asn Glu Leu Gly Val Ala Gly Ala Leu
225                 230                 235                 240

Arg Gln Gln Pro Val Glu Leu Val Gln Gly Val Ala Val Lys Glu Lys
                245                 250                 255

Ala Ile Ala Arg Ala Glu Ile Ile Ile Glu Gly Glu Leu Leu Pro Gly
            260                 265                 270

Val Arg Val Arg Glu Asp Gln His Thr Asn Thr Gly His Ala Met Pro
        275                 280                 285

Glu Phe Pro Gly Tyr Cys Gly Glu Ala Asn Pro Ser Leu Pro Val Ile
    290                 295                 300

Lys Val Lys Ala Val Thr Met Arg Asn His Ala Ile Leu Gln Thr Leu
305                 310                 315                 320

Val Gly Pro Gly Glu Glu His Thr Thr Leu Ala Gly Leu Pro Thr Glu
                325                 330                 335

Ala Ser Ile Arg Asn Ala Val Glu Glu Ala Ile Pro Gly Phe Leu Gln
            340                 345                 350

Asn Val Tyr Ala His Thr Ala Gly Gly Gly Lys Phe Leu Gly Ile Leu
```

```
                355                 360                 365
Gln Val Lys Lys Arg Gln Pro Ser Asp Glu Gly Arg Gln Gly Gln Ala
        370                 375                 380

Ala Leu Ile Ala Leu Ala Thr Tyr Ser Glu Leu Lys Asn Ile Ile Leu
385                 390                 395                 400

Val Asp Glu Asp Val Asp Ile Phe Asp Ser Asp Ile Leu Trp Ala
                405                 410                 415

Met Thr Thr Arg Met Gln Gly Asp Val Ser Ile Thr Thr Leu Pro Gly
                420                 425                 430

Ile Arg Gly His Gln Leu Asp Pro Ser Gln Ser Pro Asp Tyr Ser Thr
            435                 440                 445

Ser Ile Arg Gly Asn Gly Ile Ser Cys Lys Thr Ile Phe Asp Cys Thr
        450                 455                 460

Val Pro Trp Ala Leu Lys Ala Arg Phe Glu Arg Ala Pro Phe Met Glu
465                 470                 475                 480

Val Asp Pro Thr Pro Trp Ala Pro Glu Leu Phe Ser Asp Lys Lys
                485                 490                 495

<210> SEQ ID NO 19
<211> LENGTH: 603
<212> TYPE: DNA
<213> ORGANISM: Enterobacter cloacae
<220> FEATURE:
<221> NAME/KEY: CDS
<222> LOCATION: (1)..(603)

<400> SEQUENCE: 19 atg cgc ctg atc gtg ggc atg acc ggt gcg acc ggt gcg cca ctg ggc      48
Met Arg Leu Ile Val Gly Met Thr Gly Ala Thr Gly Ala Pro Leu Gly
1               5                  10                  15 gtg gcc ctg ctg cag gcc ctg cgt gat atg ccg gaa gtg gaa acc cac      96
Val Ala Leu Leu Gln Ala Leu Arg Asp Met Pro Glu Val Glu Thr His
            20                  25                  30 ctg gtg atg agc aag tgg gcc aag acc acc atc gag ctg gaa acc ccg     144
Leu Val Met Ser Lys Trp Ala Lys Thr Thr Ile Glu Leu Glu Thr Pro
        35                  40                  45 tac acc gcc cag gac gtg gcc gcc ctg gcc gat gtg gtg cat agc cca     192
Tyr Thr Ala Gln Asp Val Ala Ala Leu Ala Asp Val Val His Ser Pro
    50                  55                  60 gcc gat caa gcc gcc acc atc agc agc ggc agc ttc cgc acc gac ggc     240
Ala Asp Gln Ala Ala Thr Ile Ser Ser Gly Ser Phe Arg Thr Asp Gly
65                  70                  75                  80 atg atc gtg atc ccg tgc agc atg aaa acc ctg gcc ggt atc cgt gcc     288
Met Ile Val Ile Pro Cys Ser Met Lys Thr Leu Ala Gly Ile Arg Ala
                85                  90                  95 ggt tac gcc gaa ggc ctg gtg ggt cgt gcc gcc gac gtg gtg ctg aaa     336
Gly Tyr Ala Glu Gly Leu Val Gly Arg Ala Ala Asp Val Val Leu Lys
            100                 105                 110 gag ggt cgc aag ctg gtc ctg gtg cca cgc gaa acc cca ctg agc acc     384
Glu Gly Arg Lys Leu Val Leu Val Pro Arg Glu Thr Pro Leu Ser Thr
        115                 120                 125 atc cac ctg gaa aac atg ctg gcc ctg agc cgc atg ggc gtg gcc atg     432
Ile His Leu Glu Asn Met Leu Ala Leu Ser Arg Met Gly Val Ala Met
    130                 135                 140 gtc cca ccg atg cca gcc tac tac aac cac ccg cag acc gcc gac gac     480
Val Pro Pro Met Pro Ala Tyr Tyr Asn His Pro Gln Thr Ala Asp Asp
145                 150                 155                 160 atc acc cag cac atc gtg acc cgt gtg ctg gac cag ttc ggc ctg gaa     528
Ile Thr Gln His Ile Val Thr Arg Val Leu Asp Gln Phe Gly Leu Glu
```

```
                       165                 170                 175
cac aag aaa gcc cgt cgc tgg aac ggc ctg caa gcc gcc aag cac ttc      576
His Lys Lys Ala Arg Arg Trp Asn Gly Leu Gln Ala Ala Lys His Phe
            180                 185                 190 agc caa gag aac aac gac ggc atc tga                                  603
Ser Gln Glu Asn Asn Asp Gly Ile
        195                 200
```

<210> SEQ ID NO 20
<211> LENGTH: 200
<212> TYPE: PRT
<213> ORGANISM: Enterobacter cloacae

<400> SEQUENCE: 20

```
Met Arg Leu Ile Val Gly Met Thr Gly Ala Thr Gly Ala Pro Leu Gly
1               5                   10                  15

Val Ala Leu Leu Gln Ala Leu Arg Asp Met Pro Glu Val Glu Thr His
            20                  25                  30

Leu Val Met Ser Lys Trp Ala Lys Thr Thr Ile Glu Leu Glu Thr Pro
        35                  40                  45

Tyr Thr Ala Gln Asp Val Ala Ala Leu Ala Asp Val Val His Ser Pro
    50                  55                  60

Ala Asp Gln Ala Ala Thr Ile Ser Ser Gly Ser Phe Arg Thr Asp Gly
65                  70                  75                  80

Met Ile Val Ile Pro Cys Ser Met Lys Thr Leu Ala Gly Ile Arg Ala
                85                  90                  95

Gly Tyr Ala Glu Gly Leu Val Gly Arg Ala Ala Asp Val Val Leu Lys
            100                 105                 110

Glu Gly Arg Lys Leu Val Leu Val Pro Arg Glu Thr Pro Leu Ser Thr
        115                 120                 125

Ile His Leu Glu Asn Met Leu Ala Leu Ser Arg Met Gly Val Ala Met
    130                 135                 140

Val Pro Pro Met Pro Ala Tyr Tyr Asn His Pro Gln Thr Ala Asp Asp
145                 150                 155                 160

Ile Thr Gln His Ile Val Thr Arg Val Leu Asp Gln Phe Gly Leu Glu
                165                 170                 175

His Lys Lys Ala Arg Arg Trp Asn Gly Leu Gln Ala Ala Lys His Phe
            180                 185                 190

Ser Gln Glu Asn Asn Asp Gly Ile
        195                 200
```

<210> SEQ ID NO 21
<211> LENGTH: 222
<212> TYPE: DNA
<213> ORGANISM: Enterobacter cloacae
<220> FEATURE:
<221> NAME/KEY: CDS
<222> LOCATION: (1)..(222)

<400> SEQUENCE: 21

```
atg atc tgc cca cgc tgc gcc gac gag cag atc gag gtg atg gcc acc      48
Met Ile Cys Pro Arg Cys Ala Asp Glu Gln Ile Glu Val Met Ala Thr
1               5                   10                  15 tcg cca gtg aag ggc atc tgg acc gtg tac cag tgc cag cac tgc ctg      96
Ser Pro Val Lys Gly Ile Trp Thr Val Tyr Gln Cys Gln His Cys Leu
            20                  25                  30 tac acc tgg cgt gac acc gag ccg ctg cgt cgc acc agc cgt gag cat     144
Tyr Thr Trp Arg Asp Thr Glu Pro Leu Arg Arg Thr Ser Arg Glu His
        35                  40                  45
```

```
tac ccg gaa gcc ttc cgc atg acc cag aag gac atc gac gaa gcc cca      192
Tyr Pro Glu Ala Phe Arg Met Thr Gln Lys Asp Ile Asp Glu Ala Pro
    50                  55                  60 cag gtg ccg acc atc cca ccg ctg ctg tga                              222
Gln Val Pro Thr Ile Pro Pro Leu Leu
65                  70

<210> SEQ ID NO 22
<211> LENGTH: 73
<212> TYPE: PRT
<213> ORGANISM: Enterobacter cloacae

<400> SEQUENCE: 22

Met Ile Cys Pro Arg Cys Ala Asp Glu Gln Ile Glu Val Met Ala Thr
1               5                  10                  15

Ser Pro Val Lys Gly Ile Trp Thr Val Tyr Gln Cys Gln His Cys Leu
                20                  25                  30

Tyr Thr Trp Arg Asp Thr Glu Pro Leu Arg Arg Thr Ser Arg Glu His
            35                  40                  45

Tyr Pro Glu Ala Phe Arg Met Thr Gln Lys Asp Ile Asp Glu Ala Pro
    50                  55                  60

Gln Val Pro Thr Ile Pro Pro Leu Leu
65                  70

<210> SEQ ID NO 23
<211> LENGTH: 279
<212> TYPE: DNA
<213> ORGANISM: Enterobacter cloacae
<220> FEATURE:
<221> NAME/KEY: CDS
<222> LOCATION: (1)..(279)

<400> SEQUENCE: 23 atg acc gtg acc aat acc ccc aca ccg act ttc gat cag ctc act cgt      48
Met Thr Val Thr Asn Thr Pro Thr Pro Thr Phe Asp Gln Leu Thr Arg
1               5                  10                  15 tac atc cgt gtg cgc agc gaa cca gaa gcc aag ttc gtc gag ttc gat      96
Tyr Ile Arg Val Arg Ser Glu Pro Glu Ala Lys Phe Val Glu Phe Asp
                20                  25                  30 ttc gcc att ggt cat ccg gag ctg ttc gtc gag ttg gtg ctg ccg caa      144
Phe Ala Ile Gly His Pro Glu Leu Phe Val Glu Leu Val Leu Pro Gln
            35                  40                  45 gac gcc ttc gtg aag ttt tgc cag cac aac cgc gtg gtg gca atg gac      192
Asp Ala Phe Val Lys Phe Cys Gln His Asn Arg Val Val Ala Met Asp
    50                  55                  60 gaa gcg atg gcc aag gcg gtg gac gac gac atg gtc aag tgg cgc ttc      240
Glu Ala Met Ala Lys Ala Val Asp Asp Asp Met Val Lys Trp Arg Phe
65                  70                  75                  80 ggc gat gtc ggt cgc cgc ttg ccg aaa gac ccg ggc tga                  279
Gly Asp Val Gly Arg Arg Leu Pro Lys Asp Pro Gly
                85                  90

<210> SEQ ID NO 24
<211> LENGTH: 92
<212> TYPE: PRT
<213> ORGANISM: Enterobacter cloacae

<400> SEQUENCE: 24

Met Thr Val Thr Asn Thr Pro Thr Pro Thr Phe Asp Gln Leu Thr Arg
1               5                  10                  15

Tyr Ile Arg Val Arg Ser Glu Pro Glu Ala Lys Phe Val Glu Phe Asp
```

```
                   20                  25                  30
Phe Ala Ile Gly His Pro Glu Leu Phe Val Glu Leu Val Leu Pro Gln
                35                  40                  45

Asp Ala Phe Val Lys Phe Cys Gln His Asn Arg Val Val Ala Met Asp
         50                  55                  60

Glu Ala Met Ala Lys Ala Val Asp Asp Met Val Lys Trp Arg Phe
 65                  70                  75                  80

Gly Asp Val Gly Arg Arg Leu Pro Lys Asp Pro Gly
                85                  90

<210> SEQ ID NO 25
<211> LENGTH: 996
<212> TYPE: DNA
<213> ORGANISM: Pseudomonas putida
<220> FEATURE:
<221> NAME/KEY: CDS
<222> LOCATION: (1)..(996)

<400> SEQUENCE: 25 atg agc gta gag ata aag acc aat acg gtg gat ccg atc cgc cag acc       48
Met Ser Val Glu Ile Lys Thr Asn Thr Val Asp Pro Ile Arg Gln Thr
 1               5                  10                  15 tac ggc aac ctg caa cgg cgc ttc ggc gac aag ccg gct agc cgt tat       96
Tyr Gly Asn Leu Gln Arg Arg Phe Gly Asp Lys Pro Ala Ser Arg Tyr
                20                  25                  30 cag gaa gcc agc tac gac atc gaa gcg gtc acc aac ttt cac tat cgc      144
Gln Glu Ala Ser Tyr Asp Ile Glu Ala Val Thr Asn Phe His Tyr Arg
            35                  40                  45 ccg ctg tgg gac ccg cag cac gag ctg cac gat ccg acc cgc acg gcg      192
Pro Leu Trp Asp Pro Gln His Glu Leu His Asp Pro Thr Arg Thr Ala
        50                  55                  60 atc cgc atg acc gat tgg cac aag gtc acc gac ccc cgc caa ttc tac      240
Ile Arg Met Thr Asp Trp His Lys Val Thr Asp Pro Arg Gln Phe Tyr
 65                  70                  75                  80 tac ggc gcc tat gtg cag acc cgc gcg cgg atg cag gaa gcc acc gaa      288
Tyr Gly Ala Tyr Val Gln Thr Arg Ala Arg Met Gln Glu Ala Thr Glu
                85                  90                  95 cac gcc tat ggc ttc tgc gaa aag cgt gag ctg ctg agc cgt ctg ccg      336
His Ala Tyr Gly Phe Cys Glu Lys Arg Glu Leu Leu Ser Arg Leu Pro
            100                 105                 110 gcc gag ttg cag gcc aag ctg ctg cgc tgc ctg gtg ccg ctg cgg cat      384
Ala Glu Leu Gln Ala Lys Leu Leu Arg Cys Leu Val Pro Leu Arg His
        115                 120                 125 gcc gag ctg ggc gcc aac atg aat aac agc agc atc gcc ggc gac agc      432
Ala Glu Leu Gly Ala Asn Met Asn Asn Ser Ser Ile Ala Gly Asp Ser
    130                 135                 140 atc gcc gcc acc gtg acc cag atg cac atc tac cag gcg atg gac cgc      480
Ile Ala Ala Thr Val Thr Gln Met His Ile Tyr Gln Ala Met Asp Arg
145                 150                 155                 160 ctg ggc atg ggc cag tac ctc tcg cgc atc ggc ctg ctc gat ggc           528
Leu Gly Met Gly Gln Tyr Leu Ser Arg Ile Gly Leu Leu Asp Gly
                165                 170                 175 ggc acc ggc gag gcg ttg gat caa gcc aag gcc tat tgg ctc gac gac      576
Gly Thr Gly Glu Ala Leu Asp Gln Ala Lys Ala Tyr Trp Leu Asp Asp
            180                 185                 190 ccg atc tgg cag ggc ctg cgt cgc tac gtc gaa gac agc ttc gtg atc      624
Pro Ile Trp Gln Gly Leu Arg Arg Tyr Val Glu Asp Ser Phe Val Ile
        195                 200                 205 cgc gac tgg ttc gag ttg ggc ctg gcg cag aac ctg gtg ctc gac ggc      672
Arg Asp Trp Phe Glu Leu Gly Leu Ala Gln Asn Leu Val Leu Asp Gly
```

```
                210                 215                 220
ttg ctg cag ccg ctg atg tac cag cgc ttc gac caa tgg ctc aca gag      720
Leu Leu Gln Pro Leu Met Tyr Gln Arg Phe Asp Gln Trp Leu Thr Glu
225                 230                 235                 240 aac ggt ggc agc gat gtg gcc atg ctc acc gag ttc atg cgc gac tgg      768
Asn Gly Gly Ser Asp Val Ala Met Leu Thr Glu Phe Met Arg Asp Trp
                245                 250                 255 tac ggc gaa agc acg cgc tgg gtc gac gcc atg ttc aag acc gtg ctt      816
Tyr Gly Glu Ser Thr Arg Trp Val Asp Ala Met Phe Lys Thr Val Leu
            260                 265                 270 gcc gaa aat gac gct aac cgt gag cag gtg cag gcc tgg ctg gag gtc      864
Ala Glu Asn Asp Ala Asn Arg Glu Gln Val Gln Ala Trp Leu Glu Val
        275                 280                 285 tgg gag ccg cgt gcc tac gag gca ttg ttg ccc ctg gcc gag gaa gcc      912
Trp Glu Pro Arg Ala Tyr Glu Ala Leu Leu Pro Leu Ala Glu Glu Ala
290                 295                 300 acc ggt atc gcc gcg ctg gat gaa gtc cgc agc gcc ttc gct act cgc      960
Thr Gly Ile Ala Ala Leu Asp Glu Val Arg Ser Ala Phe Ala Thr Arg
305                 310                 315                 320 ctg cag aaa atc ggc ctg aaa agc cgc gag gaa taa                      996
Leu Gln Lys Ile Gly Leu Lys Ser Arg Glu Glu
                325                 330
```

<210> SEQ ID NO 26
<211> LENGTH: 331
<212> TYPE: PRT
<213> ORGANISM: Pseudomonas putida

<400> SEQUENCE: 26

```
Met Ser Val Glu Ile Lys Thr Asn Thr Val Asp Pro Ile Arg Gln Thr
1               5                   10                  15

Tyr Gly Asn Leu Gln Arg Arg Phe Gly Asp Lys Pro Ala Ser Arg Tyr
            20                  25                  30

Gln Glu Ala Ser Tyr Asp Ile Glu Ala Val Thr Asn Phe His Tyr Arg
        35                  40                  45

Pro Leu Trp Asp Pro Gln His Glu Leu His Asp Pro Thr Arg Thr Ala
    50                  55                  60

Ile Arg Met Thr Asp Trp His Lys Val Thr Asp Pro Arg Gln Phe Tyr
65                  70                  75                  80

Tyr Gly Ala Tyr Val Gln Thr Arg Ala Arg Met Gln Glu Ala Thr Glu
                85                  90                  95

His Ala Tyr Gly Phe Cys Glu Lys Arg Glu Leu Leu Ser Arg Leu Pro
            100                 105                 110

Ala Glu Leu Gln Ala Lys Leu Leu Arg Cys Leu Val Pro Leu Arg His
        115                 120                 125

Ala Glu Leu Gly Ala Asn Met Asn Asn Ser Ser Ile Ala Gly Asp Ser
    130                 135                 140

Ile Ala Ala Thr Val Thr Gln Met His Ile Tyr Gln Ala Met Asp Arg
145                 150                 155                 160

Leu Gly Met Gly Gln Tyr Leu Ser Arg Ile Gly Leu Leu Asp Gly
                165                 170                 175

Gly Thr Gly Glu Ala Leu Asp Gln Ala Lys Ala Tyr Trp Leu Asp Asp
            180                 185                 190

Pro Ile Trp Gln Gly Leu Arg Arg Tyr Val Glu Asp Ser Phe Val Ile
        195                 200                 205

Arg Asp Trp Phe Glu Leu Gly Leu Ala Gln Asn Leu Val Leu Asp Gly
    210                 215                 220
```

```
Leu Leu Gln Pro Leu Met Tyr Gln Arg Phe Asp Gln Trp Leu Thr Glu
225                 230                 235                 240

Asn Gly Gly Ser Asp Val Ala Met Leu Thr Glu Phe Met Arg Asp Trp
            245                 250                 255

Tyr Gly Glu Ser Thr Arg Trp Val Asp Ala Met Phe Lys Thr Val Leu
        260                 265                 270

Ala Glu Asn Asp Ala Asn Arg Glu Gln Val Gln Ala Trp Leu Glu Val
    275                 280                 285

Trp Glu Pro Arg Ala Tyr Glu Ala Leu Leu Pro Leu Ala Glu Glu Ala
    290                 295                 300

Thr Gly Ile Ala Ala Leu Asp Glu Val Arg Ser Ala Phe Ala Thr Arg
305                 310                 315                 320

Leu Gln Lys Ile Gly Leu Lys Ser Arg Glu Glu
                325                 330
```

<210> SEQ ID NO 27
<211> LENGTH: 273
<212> TYPE: DNA
<213> ORGANISM: Pseudomonas putida
<220> FEATURE:
<221> NAME/KEY: CDS
<222> LOCATION: (1)..(273)

<400> SEQUENCE: 27

```
atg tca tca ctc gtc tac atc gcc ttc cag gat aac gac aac gcg cgt      48
Met Ser Ser Leu Val Tyr Ile Ala Phe Gln Asp Asn Asp Asn Ala Arg
1               5                   10                  15 tac gtg gtg gaa gcg atc atc cag gac aac ccc cac gcc gtc gtc cag      96
Tyr Val Val Glu Ala Ile Ile Gln Asp Asn Pro His Ala Val Val Gln
            20                  25                  30 cac cac ccg gcg atg atc cgt atc gag gcc gag aag cgc ctg gag atc     144
His His Pro Ala Met Ile Arg Ile Glu Ala Glu Lys Arg Leu Glu Ile
        35                  40                  45 cgc agg gaa acc gtg gaa gag aac ctc ggc cgc gcc tgg gac gtc cag     192
Arg Arg Glu Thr Val Glu Glu Asn Leu Gly Arg Ala Trp Asp Val Gln
    50                  55                  60 gaa atg ctg gtg gac gta atc acc atc ggc ggc aac gtc gac gag gac     240
Glu Met Leu Val Asp Val Ile Thr Ile Gly Gly Asn Val Asp Glu Asp
65                  70                  75                  80 gat gac cgc ttc gtc ctc gag tgg aag aac tag                          273
Asp Asp Arg Phe Val Leu Glu Trp Lys Asn
                85                  90
```

<210> SEQ ID NO 28
<211> LENGTH: 90
<212> TYPE: PRT
<213> ORGANISM: Pseudomonas putida

<400> SEQUENCE: 28

```
Met Ser Ser Leu Val Tyr Ile Ala Phe Gln Asp Asn Asp Asn Ala Arg
1               5                   10                  15

Tyr Val Val Glu Ala Ile Ile Gln Asp Asn Pro His Ala Val Val Gln
            20                  25                  30

His His Pro Ala Met Ile Arg Ile Glu Ala Glu Lys Arg Leu Glu Ile
        35                  40                  45

Arg Arg Glu Thr Val Glu Glu Asn Leu Gly Arg Ala Trp Asp Val Gln
    50                  55                  60

Glu Met Leu Val Asp Val Ile Thr Ile Gly Gly Asn Val Asp Glu Asp
65                  70                  75                  80
```

```
                  Asp Asp Arg Phe Val Leu Glu Trp Lys Asn
                                   85                  90

<210> SEQ ID NO 29
<211> LENGTH: 1554
<212> TYPE: DNA
<213> ORGANISM: Pseudomonas putida
<220> FEATURE:
<221> NAME/KEY: CDS
<222> LOCATION: (1)..(1554)

<400> SEQUENCE: 29 atg gct acc cac aac aag aaa cgc ctc aac ctg aaa gac aaa tac cgc      48
Met Ala Thr His Asn Lys Lys Arg Leu Asn Leu Lys Asp Lys Tyr Arg
1               5                   10                  15 tac ctg acc cgc gat ctg gcc tgg gaa acg acc tac cag aag aaa gaa      96
Tyr Leu Thr Arg Asp Leu Ala Trp Glu Thr Thr Tyr Gln Lys Lys Glu
            20                  25                  30 gac gtg ttc ccg ctg gag cac ttc gag ggc atc aag atc acc gac tgg     144
Asp Val Phe Pro Leu Glu His Phe Glu Gly Ile Lys Ile Thr Asp Trp
        35                  40                  45 gac aag tgg gaa gac ccc ttc cgc ctg acc atg gac acc tac tgg aaa     192
Asp Lys Trp Glu Asp Pro Phe Arg Leu Thr Met Asp Thr Tyr Trp Lys
    50                  55                  60 tac cag gcg gag aaa gag aag aag ctc tac gcg atc ttc gac gcc ttt     240
Tyr Gln Ala Glu Lys Glu Lys Lys Leu Tyr Ala Ile Phe Asp Ala Phe
65                  70                  75                  80 gcc cag aac aat ggt cat cag aac att tcc gat gcg cgc tac gtc aac     288
Ala Gln Asn Asn Gly His Gln Asn Ile Ser Asp Ala Arg Tyr Val Asn
                85                  90                  95 gcc ctg aag ctg ttc ctc acc gcc gtt tca ccg ctg gaa tac cag gcc     336
Ala Leu Lys Leu Phe Leu Thr Ala Val Ser Pro Leu Glu Tyr Gln Ala
            100                 105                 110 ttc cag ggc ttc tcg cgg gtt ggc cgg cag ttc agt ggc gcc ggt gcg     384
Phe Gln Gly Phe Ser Arg Val Gly Arg Gln Phe Ser Gly Ala Gly Ala
        115                 120                 125 cgg gtc gcc tgt cag atg cag gcg atc gac gag ctg cgc cat gtg cag     432
Arg Val Ala Cys Gln Met Gln Ala Ile Asp Glu Leu Arg His Val Gln
    130                 135                 140 acg caa gtc cac gcc atg agc cat tac aac aag cac ttc gat ggt ttg     480
Thr Gln Val His Ala Met Ser His Tyr Asn Lys His Phe Asp Gly Leu
145                 150                 155                 160 cat gac ttc gcc cac atg tac gac cgg gtc tgg tac ctc tcg gta ccc     528
His Asp Phe Ala His Met Tyr Asp Arg Val Trp Tyr Leu Ser Val Pro
                165                 170                 175 aag tcc tat atg gac gat gcg cgg acc gcc ggt ccg ttc gag ttc ctc     576
Lys Ser Tyr Met Asp Asp Ala Arg Thr Ala Gly Pro Phe Glu Phe Leu
            180                 185                 190 acc gcc gtc tcg ttc tcc ttc gag tac gtg ctg acc aac ctg ttg ttc     624
Thr Ala Val Ser Phe Ser Phe Glu Tyr Val Leu Thr Asn Leu Leu Phe
        195                 200                 205 gta ccc ttc atg tcc ggt gcc gcc tac aac ggc gat atg gcc acg gtc     672
Val Pro Phe Met Ser Gly Ala Ala Tyr Asn Gly Asp Met Ala Thr Val
    210                 215                 220 acc ttc ggt ttc tcc gcg cag tcg gac gag gcg cgg cac atg acc ctg     720
Thr Phe Gly Phe Ser Ala Gln Ser Asp Glu Ala Arg His Met Thr Leu
225                 230                 235                 240 ggt ctg gaa gtg atc aag ttc atg ctc gaa cag cat gaa gac aac gtg     768
Gly Leu Glu Val Ile Lys Phe Met Leu Glu Gln His Glu Asp Asn Val
                245                 250                 255
```

```
ccc atc atc cag cgc tgg atc gat aag tgg ttc tgg cgc ggt tac cgc      816
Pro Ile Ile Gln Arg Trp Ile Asp Lys Trp Phe Trp Arg Gly Tyr Arg
        260                 265                 270 ctg ctg acc ctg atc ggc atg atg atg gac tac atg ctg ccg aac aaa      864
Leu Leu Thr Leu Ile Gly Met Met Met Asp Tyr Met Leu Pro Asn Lys
            275                 280                 285 gtg atg tcc tgg tct gag gcc tgg ggg gtc tac ttc gag cag gcc ggt      912
Val Met Ser Trp Ser Glu Ala Trp Gly Val Tyr Phe Glu Gln Ala Gly
    290                 295                 300 ggc gcg ctg ttc aag gat ctg gag cgc tat ggc atc cgg ccg ccg aaa      960
Gly Ala Leu Phe Lys Asp Leu Glu Arg Tyr Gly Ile Arg Pro Pro Lys
305                 310                 315                 320 tac gtc gag cag acc acc atc ggc aag gag cac atc acc cac cag gtg     1008
Tyr Val Glu Gln Thr Thr Ile Gly Lys Glu His Ile Thr His Gln Val
                325                 330                 335 tgg ggg gcc tta tat caa tac agc aag gcc acc agc ttc cat acc tgg     1056
Trp Gly Ala Leu Tyr Gln Tyr Ser Lys Ala Thr Ser Phe His Thr Trp
            340                 345                 350 ata ccc ggc gac gag gaa ctg aac tgg ctg tcg gag aaa tac ccg gac     1104
Ile Pro Gly Asp Glu Glu Leu Asn Trp Leu Ser Glu Lys Tyr Pro Asp
        355                 360                 365 acc ttc gac aaa tac tac cgc ccg cgc ttc gag ttc tgg cgt gag cag     1152
Thr Phe Asp Lys Tyr Tyr Arg Pro Arg Phe Glu Phe Trp Arg Glu Gln
370                 375                 380 cag gcc aag ggt gag cgc ttc tac aac gac acc ctg ccg cac ctc tgc     1200
Gln Ala Lys Gly Glu Arg Phe Tyr Asn Asp Thr Leu Pro His Leu Cys
385                 390                 395                 400 cag gtg tgc cag tta ccg gtg att ttc acc gag ccg gac gat ccg acc     1248
Gln Val Cys Gln Leu Pro Val Ile Phe Thr Glu Pro Asp Asp Pro Thr
                405                 410                 415 aag ctc agc ctg cgc agc ctg gtg cac gag ggg gag cgc tat caa ttc     1296
Lys Leu Ser Leu Arg Ser Leu Val His Glu Gly Glu Arg Tyr Gln Phe
            420                 425                 430 tgc tcg gat ggc tgc tgc gac atc ttc aag aac gag ccg gtg aag tac     1344
Cys Ser Asp Gly Cys Cys Asp Ile Phe Lys Asn Glu Pro Val Lys Tyr
        435                 440                 445 atc cag gcc tgg ctg ccg gtg cac cag atc tac cag ggc aac tgc gaa     1392
Ile Gln Ala Trp Leu Pro Val His Gln Ile Tyr Gln Gly Asn Cys Glu
450                 455                 460 ggc ggg gat gtc gaa acg gtg gtg cag aag tac tac cac atc aaa agc     1440
Gly Gly Asp Val Glu Thr Val Val Gln Lys Tyr Tyr His Ile Lys Ser
                465                 470                 475                 480 ggc gtg gac aat ttg gag tac ctg ggc tcg ccc gag cac cag cgc tgg     1488
Gly Val Asp Asn Leu Glu Tyr Leu Gly Ser Pro Glu His Gln Arg Trp
            485                 490                 495 ctg gcc ctg aaa ggt cag acc cca cca act gcc gcc ccg gcg gac aag     1536
Leu Ala Leu Lys Gly Gln Thr Pro Pro Thr Ala Ala Pro Ala Asp Lys
        500                 505                 510 agc ctg ggc gcc gcc tga                                              1554
Ser Leu Gly Ala Ala
            515

<210> SEQ ID NO 30
<211> LENGTH: 517
<212> TYPE: PRT
<213> ORGANISM: Pseudomonas putida

<400> SEQUENCE: 30

Met Ala Thr His Asn Lys Lys Arg Leu Asn Leu Lys Asp Lys Tyr Arg
1               5                   10                  15
```

Tyr Leu Thr Arg Asp Leu Ala Trp Glu Thr Thr Tyr Gln Lys Lys Glu
              20                  25                  30

Asp Val Phe Pro Leu Glu His Phe Glu Gly Ile Lys Ile Thr Asp Trp
             35                  40                  45

Asp Lys Trp Glu Asp Pro Phe Arg Leu Thr Met Asp Thr Tyr Trp Lys
 50                  55                  60

Tyr Gln Ala Glu Lys Glu Lys Lys Leu Tyr Ala Ile Phe Asp Ala Phe
 65                  70                  75                  80

Ala Gln Asn Asn Gly His Gln Asn Ile Ser Asp Ala Arg Tyr Val Asn
                 85                  90                  95

Ala Leu Lys Leu Phe Leu Thr Ala Val Ser Pro Leu Glu Tyr Gln Ala
             100                 105                 110

Phe Gln Gly Phe Ser Arg Val Gly Arg Gln Phe Ser Gly Ala Gly Ala
             115                 120                 125

Arg Val Ala Cys Gln Met Gln Ala Ile Asp Glu Leu Arg His Val Gln
 130                 135                 140

Thr Gln Val His Ala Met Ser His Tyr Asn Lys His Phe Asp Gly Leu
145                 150                 155                 160

His Asp Phe Ala His Met Tyr Asp Arg Val Trp Tyr Leu Ser Val Pro
                165                 170                 175

Lys Ser Tyr Met Asp Asp Ala Arg Thr Ala Gly Pro Phe Glu Phe Leu
            180                 185                 190

Thr Ala Val Ser Phe Ser Phe Glu Tyr Val Leu Thr Asn Leu Leu Phe
            195                 200                 205

Val Pro Phe Met Ser Gly Ala Ala Tyr Asn Gly Asp Met Ala Thr Val
210                 215                 220

Thr Phe Gly Phe Ser Ala Gln Ser Asp Glu Ala Arg His Met Thr Leu
225                 230                 235                 240

Gly Leu Glu Val Ile Lys Phe Met Leu Glu Gln His Glu Asp Asn Val
                245                 250                 255

Pro Ile Ile Gln Arg Trp Ile Asp Lys Trp Phe Trp Arg Gly Tyr Arg
            260                 265                 270

Leu Leu Thr Leu Ile Gly Met Met Met Asp Tyr Met Leu Pro Asn Lys
            275                 280                 285

Val Met Ser Trp Ser Glu Ala Trp Gly Val Tyr Phe Glu Gln Ala Gly
290                 295                 300

Gly Ala Leu Phe Lys Asp Leu Glu Arg Tyr Gly Ile Arg Pro Pro Lys
305                 310                 315                 320

Tyr Val Glu Gln Thr Thr Ile Gly Lys Glu His Ile Thr His Gln Val
                325                 330                 335

Trp Gly Ala Leu Tyr Gln Tyr Ser Lys Ala Thr Ser Phe His Thr Trp
            340                 345                 350

Ile Pro Gly Asp Glu Glu Leu Asn Trp Leu Ser Glu Lys Tyr Pro Asp
            355                 360                 365

Thr Phe Asp Lys Tyr Tyr Arg Pro Arg Phe Glu Phe Trp Arg Glu Gln
370                 375                 380

Gln Ala Lys Gly Glu Arg Phe Tyr Asn Asp Thr Leu Pro His Leu Cys
385                 390                 395                 400

Gln Val Cys Gln Leu Pro Val Ile Phe Thr Glu Pro Asp Asp Pro Thr
                405                 410                 415

Lys Leu Ser Leu Arg Ser Leu Val His Glu Gly Glu Arg Tyr Gln Phe
            420                 425                 430

Cys Ser Asp Gly Cys Cys Asp Ile Phe Lys Asn Glu Pro Val Lys Tyr

```
                 435                 440                 445
Ile Gln Ala Trp Leu Pro Val His Gln Ile Tyr Gln Gly Asn Cys Glu
    450                 455                 460

Gly Gly Asp Val Glu Thr Val Gln Lys Tyr Tyr His Ile Lys Ser
465                 470                 475                 480

Gly Val Asp Asn Leu Glu Tyr Leu Gly Ser Pro Glu His Gln Arg Trp
                485                 490                 495

Leu Ala Leu Lys Gly Gln Thr Pro Pro Thr Ala Ala Pro Ala Asp Lys
                500                 505                 510

Ser Leu Gly Ala Ala
        515

<210> SEQ ID NO 31
<211> LENGTH: 1554
<212> TYPE: DNA
<213> ORGANISM: Pseudomonas putida
<220> FEATURE:
<221> NAME/KEY: CDS
<222> LOCATION: (1)..(1554)

<400> SEQUENCE: 31 atg gct acc cac aac aag aaa cgc ctc aac ctg aaa gac aaa tac cgc      48
Met Ala Thr His Asn Lys Lys Arg Leu Asn Leu Lys Asp Lys Tyr Arg
1               5                   10                  15 tac ctg acc cgc gat ctg gcc tgg gaa acg acc tac cag aag aaa gaa      96
Tyr Leu Thr Arg Asp Leu Ala Trp Glu Thr Thr Tyr Gln Lys Lys Glu
            20                  25                  30 gac gtg ttc ccg ctg gag cac ttc gag ggc atc aag atc acc gac tgg     144
Asp Val Phe Pro Leu Glu His Phe Glu Gly Ile Lys Ile Thr Asp Trp
        35                  40                  45 gac aag tgg gaa gac ccc ttc cgc ctg acc atg gac acc tac tgg aaa     192
Asp Lys Trp Glu Asp Pro Phe Arg Leu Thr Met Asp Thr Tyr Trp Lys
    50                  55                  60 tac cag gcg gag aaa gag aag aag ctc tac gcg atc ttc gac gcc ttt     240
Tyr Gln Ala Glu Lys Glu Lys Lys Leu Tyr Ala Ile Phe Asp Ala Phe
65                  70                  75                  80 gcc cag aac aat ggt cat cag aac att tcc gat gcg cgc tac gtc aac     288
Ala Gln Asn Asn Gly His Gln Asn Ile Ser Asp Ala Arg Tyr Val Asn
                85                  90                  95 gcc ctg aag ctg ttc ctc acc gcc gtt tca ccg ctg gaa tac cag gcc     336
Ala Leu Lys Leu Phe Leu Thr Ala Val Ser Pro Leu Glu Tyr Gln Ala
            100                 105                 110 ttc cag ggc ttc tcg cgg gtt ggc cgg cag ttc agt ggc gcc ggt gcg     384
Phe Gln Gly Phe Ser Arg Val Gly Arg Gln Phe Ser Gly Ala Gly Ala
        115                 120                 125 cgg gtc gcc tgt cag atg cag gcg atc gac gag ctg cgc cat gtg cag     432
Arg Val Ala Cys Gln Met Gln Ala Ile Asp Glu Leu Arg His Val Gln
    130                 135                 140 acg caa gtc cac gcc atg agc cat tac aac aag cac ttc gat ggt ttg     480
Thr Gln Val His Ala Met Ser His Tyr Asn Lys His Phe Asp Gly Leu
145                 150                 155                 160 cat gac ttc gcc cac atg tac gac cgg gtc tgg tac ctc tcg gta ccc     528
His Asp Phe Ala His Met Tyr Asp Arg Val Trp Tyr Leu Ser Val Pro
                165                 170                 175 aag tcc tat atg gac gat gcg cgg acc gcc ggt ccg ttc gag ttc ctc     576
Lys Ser Tyr Met Asp Asp Ala Arg Thr Ala Gly Pro Phe Glu Phe Leu
            180                 185                 190 acc gcc gtc tcg ttc tcc ttc gag tac gtg ctg acc aac ctg ttg ttc     624
Thr Ala Val Ser Phe Ser Phe Glu Tyr Val Leu Thr Asn Leu Leu Phe
        195                 200                 205
```

```
gta ccc ttc atg tcc ggt gcc gcc tac aac ggc gat atg gcc acg gtc      672
Val Pro Phe Met Ser Gly Ala Ala Tyr Asn Gly Asp Met Ala Thr Val
    210                 215                 220 acc ttc ggt ttc tcc gcg cag tcg gac gag gcg cgg cac atg acc ctg      720
Thr Phe Gly Phe Ser Ala Gln Ser Asp Glu Ala Arg His Met Thr Leu
225                 230                 235                 240 ggt ctg gaa gtg atc aag ttc atg ctc gaa cag cat gaa gac aac gtg      768
Gly Leu Glu Val Ile Lys Phe Met Leu Glu Gln His Glu Asp Asn Val
                    245                 250                 255 ccc atc atc cag cgc tgg atc gat aag tgg ttc tgg cgc ggt tac cgc      816
Pro Ile Ile Gln Arg Trp Ile Asp Lys Trp Phe Trp Arg Gly Tyr Arg
                260                 265                 270 ctg ctg acc ctg atc ggc atg atg atg gac tac atg ctg ccg aac aaa      864
Leu Leu Thr Leu Ile Gly Met Met Met Asp Tyr Met Leu Pro Asn Lys
            275                 280                 285 gtg atg tcc tgg tct gag gcc tgg ggg gtc tac ttc gag cag gcc ggt      912
Val Met Ser Trp Ser Glu Ala Trp Gly Val Tyr Phe Glu Gln Ala Gly
        290                 295                 300 ggc gcg ctg ttc aag gat ctg gag cgc tat ggc atc cgg ccg ccg aaa      960
Gly Ala Leu Phe Lys Asp Leu Glu Arg Tyr Gly Ile Arg Pro Pro Lys
305                 310                 315                 320 tac gtc gag cag acc acc atc ggc aag gag cac atc acc cac cag gtg     1008
Tyr Val Glu Gln Thr Thr Ile Gly Lys Glu His Ile Thr His Gln Val
                    325                 330                 335 tgg ggg gcc tta tat caa tac agc aag gcc acc agc ttc cat acc tgg     1056
Trp Gly Ala Leu Tyr Gln Tyr Ser Lys Ala Thr Ser Phe His Thr Trp
                340                 345                 350 ata ccc ggc gac gag gaa ctg aac tgg ctg tcg gag aaa tac ccg gac     1104
Ile Pro Gly Asp Glu Glu Leu Asn Trp Leu Ser Glu Lys Tyr Pro Asp
            355                 360                 365 acc ttc gac aaa tac tac cgc ccg cgc ttc gag ttc tgg cgt gag cag     1152
Thr Phe Asp Lys Tyr Tyr Arg Pro Arg Phe Glu Phe Trp Arg Glu Gln
        370                 375                 380 cag gcc aag ggt gag cgc ttc tac aac gac acc ctg ccg cac ctc tgc     1200
Gln Ala Lys Gly Glu Arg Phe Tyr Asn Asp Thr Leu Pro His Leu Cys
385                 390                 395                 400 cag gtg tgc cag tta ccg gtg att ttc acc gag ccg gac gat ccg acc     1248
Gln Val Cys Gln Leu Pro Val Ile Phe Thr Glu Pro Asp Asp Pro Thr
                    405                 410                 415 aag ctc agc ctg cgc agc ctg gtg cac gag ggg gag cgc tat caa ttc     1296
Lys Leu Ser Leu Arg Ser Leu Val His Glu Gly Glu Arg Tyr Gln Phe
                420                 425                 430 tgc tcg gat ggc tgc tgc gac atc ttc aag aac gag ccg gtg aag tac     1344
Cys Ser Asp Gly Cys Cys Asp Ile Phe Lys Asn Glu Pro Val Lys Tyr
            435                 440                 445 atc cag gcc tgg ctg ccg gtg cac cag atc tac cag ggc aac tgc gaa     1392
Ile Gln Ala Trp Leu Pro Val His Gln Ile Tyr Gln Gly Asn Cys Glu
        450                 455                 460 ggc ggg gat gtc gaa acg gtg gtg cag aag tac tac cac atc aaa agc     1440
Gly Gly Asp Val Glu Thr Val Val Gln Lys Tyr Tyr His Ile Lys Ser
465                 470                 475                 480 ggc gtg gac aat ttg gag tac ctg ggc tcg ccc gag cac cag cgc tgg     1488
Gly Val Asp Asn Leu Glu Tyr Leu Gly Ser Pro Glu His Gln Arg Trp
                    485                 490                 495 ctg gcc ctg aaa ggt cag acc cca cca act gcc gcc ccg gcg gac aag     1536
Leu Ala Leu Lys Gly Gln Thr Pro Pro Thr Ala Ala Pro Ala Asp Lys
                500                 505                 510 agc ctg ggc gcc gcc tga                                             1554
Ser Leu Gly Ala Ala
```

-continued

515

<210> SEQ ID NO 32
<211> LENGTH: 517
<212> TYPE: PRT
<213> ORGANISM: Pseudomonas putida

<400> SEQUENCE: 32

```
Met Ala Thr His Asn Lys Lys Arg Leu Asn Leu Lys Asp Lys Tyr Arg
1               5                   10                  15

Tyr Leu Thr Arg Asp Leu Ala Trp Glu Thr Thr Tyr Gln Lys Lys Glu
            20                  25                  30

Asp Val Phe Pro Leu Glu His Phe Glu Gly Ile Lys Ile Thr Asp Trp
        35                  40                  45

Asp Lys Trp Glu Asp Pro Phe Arg Leu Thr Met Asp Thr Tyr Trp Lys
    50                  55                  60

Tyr Gln Ala Glu Lys Glu Lys Lys Leu Tyr Ala Ile Phe Asp Ala Phe
65                  70                  75                  80

Ala Gln Asn Asn Gly His Gln Asn Ile Ser Asp Ala Arg Tyr Val Asn
                85                  90                  95

Ala Leu Lys Leu Phe Leu Thr Ala Val Ser Pro Leu Glu Tyr Gln Ala
            100                 105                 110

Phe Gln Gly Phe Ser Arg Val Gly Arg Gln Phe Ser Gly Ala Gly Ala
        115                 120                 125

Arg Val Ala Cys Gln Met Gln Ala Ile Asp Glu Leu Arg His Val Gln
    130                 135                 140

Thr Gln Val His Ala Met Ser His Tyr Asn Lys His Phe Asp Gly Leu
145                 150                 155                 160

His Asp Phe Ala His Met Tyr Asp Arg Val Trp Tyr Leu Ser Val Pro
                165                 170                 175

Lys Ser Tyr Met Asp Asp Ala Arg Thr Ala Gly Pro Phe Glu Phe Leu
            180                 185                 190

Thr Ala Val Ser Phe Ser Phe Glu Tyr Val Leu Thr Asn Leu Leu Phe
        195                 200                 205

Val Pro Phe Met Ser Gly Ala Ala Tyr Asn Gly Asp Met Ala Thr Val
    210                 215                 220

Thr Phe Gly Phe Ser Ala Gln Ser Asp Glu Ala Arg His Met Thr Leu
225                 230                 235                 240

Gly Leu Glu Val Ile Lys Phe Met Leu Glu Gln His Glu Asp Asn Val
                245                 250                 255

Pro Ile Ile Gln Arg Trp Ile Asp Lys Trp Phe Trp Arg Gly Tyr Arg
            260                 265                 270

Leu Leu Thr Leu Ile Gly Met Met Met Asp Tyr Met Leu Pro Asn Lys
        275                 280                 285

Val Met Ser Trp Ser Glu Ala Trp Gly Val Tyr Phe Glu Gln Ala Gly
    290                 295                 300

Gly Ala Leu Phe Lys Asp Leu Glu Arg Tyr Gly Ile Arg Pro Pro Lys
305                 310                 315                 320

Tyr Val Glu Gln Thr Thr Ile Gly Lys Glu His Ile Thr His Gln Val
                325                 330                 335

Trp Gly Ala Leu Tyr Gln Tyr Ser Lys Ala Thr Ser Phe His Thr Trp
            340                 345                 350

Ile Pro Gly Asp Glu Glu Leu Asn Trp Leu Ser Glu Lys Tyr Pro Asp
        355                 360                 365
```

```
Thr Phe Asp Lys Tyr Tyr Arg Pro Arg Phe Glu Phe Trp Arg Glu Gln
    370             375                 380

Gln Ala Lys Gly Glu Arg Phe Tyr Asn Asp Thr Leu Pro His Leu Cys
385             390                 395                 400

Gln Val Cys Gln Leu Pro Val Ile Phe Thr Glu Pro Asp Asp Pro Thr
                405                 410                 415

Lys Leu Ser Leu Arg Ser Leu Val His Glu Gly Glu Arg Tyr Gln Phe
            420                 425                 430

Cys Ser Asp Gly Cys Cys Asp Ile Phe Lys Asn Glu Pro Val Lys Tyr
            435                 440                 445

Ile Gln Ala Trp Leu Pro Val His Gln Ile Tyr Gln Gly Asn Cys Glu
450                 455                 460

Gly Gly Asp Val Glu Thr Val Val Gln Lys Tyr Tyr His Ile Lys Ser
465                 470                 475                 480

Gly Val Asp Asn Leu Glu Tyr Leu Gly Ser Pro Glu His Gln Arg Trp
                485                 490                 495

Leu Ala Leu Lys Gly Gln Thr Pro Pro Thr Ala Ala Pro Ala Asp Lys
            500                 505                 510

Ser Leu Gly Ala Ala
        515

<210> SEQ ID NO 33
<211> LENGTH: 1062
<212> TYPE: DNA
<213> ORGANISM: Pseudomonas putida
<220> FEATURE:
<221> NAME/KEY: CDS
<222> LOCATION: (1)..(1062)

<400> SEQUENCE: 33 atg agt tac aac gtc acc att gaa ccg acc ggc gaa gtg atc gaa gtg      48
Met Ser Tyr Asn Val Thr Ile Glu Pro Thr Gly Glu Val Ile Glu Val
1               5                   10                  15 gag gac ggc cag acc atc ctc cag gcc gct ctg cgc cag ggc gtc tgg      96
Glu Asp Gly Gln Thr Ile Leu Gln Ala Ala Leu Arg Gln Gly Val Trp
            20                  25                  30 ctg ccg ttc gcc tgc ggc cac ggc acc tgc gcc acc tgc aag gtg cag     144
Leu Pro Phe Ala Cys Gly His Gly Thr Cys Ala Thr Cys Lys Val Gln
        35                  40                  45 gtg gtc gag ggc gaa gtg gat atc ggc gaa gcc tcg ccg ttc gcc ctg     192
Val Val Glu Gly Glu Val Asp Ile Gly Glu Ala Ser Pro Phe Ala Leu
    50                  55                  60 atg gac atc gag cgc gac gag cgc aag gtg ctg gcc tgc tgc gcc att     240
Met Asp Ile Glu Arg Asp Glu Arg Lys Val Leu Ala Cys Cys Ala Ile
65                  70                  75                  80 ccg ctg tcc gac ctg gtg atc gaa gcc gac gtc gat gcc gac ccg gac     288
Pro Leu Ser Asp Leu Val Ile Glu Ala Asp Val Asp Ala Asp Pro Asp
                85                  90                  95 ttc ctc ggc cat ccg gtg gag gat tac cgg ggg gtg gtc agc gcc ctg     336
Phe Leu Gly His Pro Val Glu Asp Tyr Arg Gly Val Val Ser Ala Leu
            100                 105                 110 gtt gac ctg tcg ccg acc atc aag ggc ctg cac atc aag ctg gat cgg     384
Val Asp Leu Ser Pro Thr Ile Lys Gly Leu His Ile Lys Leu Asp Arg
        115                 120                 125 ccc atg ccg ttc cag gcc ggg cag tac gtc aac ctg gca ttg ccg ggc     432
Pro Met Pro Phe Gln Ala Gly Gln Tyr Val Asn Leu Ala Leu Pro Gly
    130                 135                 140 atc gac ggc acc cgc gcc ttc tcg ctg gcc aac ccg ccg agc cgg aac     480
Ile Asp Gly Thr Arg Ala Phe Ser Leu Ala Asn Pro Pro Ser Arg Asn
```

```
                 145                 150                 155                 160
gac gaa gtc gag ttg cac gtg cgc ctg gtc gag ggt gcg gcc acc       528
Asp Glu Val Glu Leu His Val Arg Leu Val Glu Gly Ala Ala Thr
                 165                 170                 175 ggc ttt atc cac aag caa ctg aaa gtc ggc gac gcg gtg gag ctg tcc   576
Gly Phe Ile His Lys Gln Leu Lys Val Gly Asp Ala Val Glu Leu Ser
             180                 185                 190 ggg cct tat ggg cag ttc ttc gtg cgc gat tcg cag gcc ggc gac ctg   624
Gly Pro Tyr Gly Gln Phe Phe Val Arg Asp Ser Gln Ala Gly Asp Leu
         195                 200                 205 atc ttc atc gcc ggc ggc tcg ggc tta tcg agc ccg cag tcg atg atc   672
Ile Phe Ile Ala Gly Gly Ser Gly Leu Ser Ser Pro Gln Ser Met Ile
     210                 215                 220 ctc gat ctg ctt gaa cgc ggc gat acg cgg cgg atc acc ctg ttc cag   720
Leu Asp Leu Leu Glu Arg Gly Asp Thr Arg Arg Ile Thr Leu Phe Gln
225                 230                 235                 240 ggc gcg cgc aac cgc gcc gag ctg tac aac tgc gaa ctg ttc gag gaa   768
Gly Ala Arg Asn Arg Ala Glu Leu Tyr Asn Cys Glu Leu Phe Glu Glu
                 245                 250                 255 ctg gcc gcg cgc cac ccc aac ttc agt tac gtg ccg gca ctc aac cag   816
Leu Ala Ala Arg His Pro Asn Phe Ser Tyr Val Pro Ala Leu Asn Gln
             260                 265                 270 gcc aac gac gat ccc gaa tgg cag ggt ttc aag ggc ttc gtc cac gac   864
Ala Asn Asp Asp Pro Glu Trp Gln Gly Phe Lys Gly Phe Val His Asp
         275                 280                 285 gcc gcc aag gcg cat ttc gac ggc cgc ttc ggc ggg cag aaa gcc tac   912
Ala Ala Lys Ala His Phe Asp Gly Arg Phe Gly Gly Gln Lys Ala Tyr
     290                 295                 300 ctg tgc ggc cca ccg ccg atg atc gac gcg gcc atc acc acc ctg atg   960
Leu Cys Gly Pro Pro Pro Met Ile Asp Ala Ala Ile Thr Thr Leu Met
305                 310                 315                 320 caa ggt cgc ttg ttc gag cgc gac atc ttt atg gag cgc ttc tac acc  1008
Gln Gly Arg Leu Phe Glu Arg Asp Ile Phe Met Glu Arg Phe Tyr Thr
                 325                 330                 335 gcc gcc gat ggg gcc ggc gag agc agc cgt tcg gcc ctg ttc aag cgc  1056
Ala Ala Asp Gly Ala Gly Glu Ser Ser Arg Ser Ala Leu Phe Lys Arg
             340                 345                 350 atc tga                                                           1062
Ile

<210> SEQ ID NO 34
<211> LENGTH: 353
<212> TYPE: PRT
<213> ORGANISM: Pseudomonas putida

<400> SEQUENCE: 34

Met Ser Tyr Asn Val Thr Ile Glu Pro Thr Gly Glu Val Ile Glu Val
1               5                   10                  15

Glu Asp Gly Gln Thr Ile Leu Gln Ala Ala Leu Arg Gln Gly Val Trp
            20                  25                  30

Leu Pro Phe Ala Cys Gly His Gly Thr Cys Ala Thr Cys Lys Val Gln
        35                  40                  45

Val Val Glu Gly Glu Val Asp Ile Gly Glu Ala Ser Pro Phe Ala Leu
    50                  55                  60

Met Asp Ile Glu Arg Asp Glu Arg Lys Val Leu Ala Cys Cys Ala Ile
65                  70                  75                  80

Pro Leu Ser Asp Leu Val Ile Glu Ala Asp Val Asp Ala Asp Pro Asp
                85                  90                  95
```

```
Phe Leu Gly His Pro Val Glu Asp Tyr Arg Gly Val Val Ser Ala Leu
                100                 105                 110

Val Asp Leu Ser Pro Thr Ile Lys Gly Leu His Ile Lys Leu Asp Arg
            115                 120                 125

Pro Met Pro Phe Gln Ala Gly Gln Tyr Val Asn Leu Ala Leu Pro Gly
        130                 135                 140

Ile Asp Gly Thr Arg Ala Phe Ser Leu Ala Asn Pro Pro Ser Arg Asn
145                 150                 155                 160

Asp Glu Val Glu Leu His Val Arg Leu Val Glu Gly Gly Ala Ala Thr
                165                 170                 175

Gly Phe Ile His Lys Gln Leu Lys Val Gly Asp Ala Val Glu Leu Ser
            180                 185                 190

Gly Pro Tyr Gly Gln Phe Phe Val Arg Asp Ser Gln Ala Gly Asp Leu
        195                 200                 205

Ile Phe Ile Ala Gly Gly Ser Gly Leu Ser Ser Pro Gln Ser Met Ile
210                 215                 220

Leu Asp Leu Leu Glu Arg Gly Asp Thr Arg Arg Ile Thr Leu Phe Gln
225                 230                 235                 240

Gly Ala Arg Asn Arg Ala Glu Leu Tyr Asn Cys Glu Leu Phe Glu Glu
                245                 250                 255

Leu Ala Ala Arg His Pro Asn Phe Ser Tyr Val Pro Ala Leu Asn Gln
            260                 265                 270

Ala Asn Asp Asp Pro Glu Trp Gln Gly Phe Lys Gly Phe Val His Asp
        275                 280                 285

Ala Ala Lys Ala His Phe Asp Gly Arg Phe Gly Gly Gln Lys Ala Tyr
        290                 295                 300

Leu Cys Gly Pro Pro Pro Met Ile Asp Ala Ala Ile Thr Thr Leu Met
305                 310                 315                 320

Gln Gly Arg Leu Phe Glu Arg Asp Ile Phe Met Glu Arg Phe Tyr Thr
                325                 330                 335

Ala Ala Asp Gly Ala Gly Glu Ser Ser Arg Ser Ala Leu Phe Lys Arg
            340                 345                 350

Ile

<210> SEQ ID NO 35
<211> LENGTH: 1833
<212> TYPE: DNA
<213> ORGANISM: Pseudomonas sp. EST1001
<220> FEATURE:
<221> NAME/KEY: CDS
<222> LOCATION: (1)..(1833)

<400> SEQUENCE: 35 atg acc acc cag cgc aac gac aac ctg gaa caa ccg ggt cgc agc gtg     48
Met Thr Thr Gln Arg Asn Asp Asn Leu Glu Gln Pro Gly Arg Ser Val
1               5                   10                  15 atc ttc gac gac ggc ctg agc gcc acc gac acc ccg aac gaa acc aac     96
Ile Phe Asp Asp Gly Leu Ser Ala Thr Asp Thr Pro Asn Glu Thr Asn
            20                  25                  30 gtg gtg gaa acc gag gtg ctg atc gtg ggc agc ggt cca gcc ggt agc    144
Val Val Glu Thr Glu Val Leu Ile Val Gly Ser Gly Pro Ala Gly Ser
        35                  40                  45 agc gcc gcc atg ttc ctg agc acc cag ggc atc agc aac atc atg atc    192
Ser Ala Ala Met Phe Leu Ser Thr Gln Gly Ile Ser Asn Ile Met Ile
    50                  55                  60 acc aag tac cgc tgg acc gcc aac acc cca cgt gcc cac atc acc aac    240
Thr Lys Tyr Arg Trp Thr Ala Asn Thr Pro Arg Ala His Ile Thr Asn
```

```
              65                  70                  75                  80
cag cgc acc atg gaa atc ctg cgt gat gcc ggt atc gag gac cag gtg           288
Gln Arg Thr Met Glu Ile Leu Arg Asp Ala Gly Ile Glu Asp Gln Val
             85                  90                  95 ctg gcc gaa gcc gtg ccg cac gaa ctg atg ggc gac acc gtg tac tgc           336
Leu Ala Glu Ala Val Pro His Glu Leu Met Gly Asp Thr Val Tyr Cys
            100                 105                 110 gag agc atg gcc ggt gag gaa atc ggt cgc cgt ccg acc tgg ggc acc           384
Glu Ser Met Ala Gly Glu Glu Ile Gly Arg Arg Pro Thr Trp Gly Thr
            115                 120                 125 cgt ccg gat cgt cgt gcc gac tac gaa ctg gcc agc cca gcc atg ccg           432
Arg Pro Asp Arg Arg Ala Asp Tyr Glu Leu Ala Ser Pro Ala Met Pro
        130                 135                 140 tgc gac atc ccg cag acc ctg ctg gaa ccg atc atg ctg aag aac gcc           480
Cys Asp Ile Pro Gln Thr Leu Leu Glu Pro Ile Met Leu Lys Asn Ala
145                 150                 155                 160 acc atg cgt ggc acc cag acc cag ttc agc acc gag tac ctg agc cac           528
Thr Met Arg Gly Thr Gln Thr Gln Phe Ser Thr Glu Tyr Leu Ser His
                165                 170                 175 acc cag gac gac aag ggc gtg agc gtg cag gtc ctg aac cgc ctg acc           576
Thr Gln Asp Asp Lys Gly Val Ser Val Gln Val Leu Asn Arg Leu Thr
            180                 185                 190 ggt caa gag tac acc atc cgt gcc aag tac ctg atc ggt gcc gac ggt           624
Gly Gln Glu Tyr Thr Ile Arg Ala Lys Tyr Leu Ile Gly Ala Asp Gly
            195                 200                 205 gcc cgt agc aag gtg gcc gcc gat atc ggt ggc agc atg aac atc acc           672
Ala Arg Ser Lys Val Ala Ala Asp Ile Gly Gly Ser Met Asn Ile Thr
        210                 215                 220 ttc aag gcc gac ctg agc cac tgg cgt ccg agc gcc ctg gat cca gtg           720
Phe Lys Ala Asp Leu Ser His Trp Arg Pro Ser Ala Leu Asp Pro Val
225                 230                 235                 240 ctg ggt ctg cca ccg cgt atc gag tac cgc tgg cca cgc cgt tgg ttc           768
Leu Gly Leu Pro Pro Arg Ile Glu Tyr Arg Trp Pro Arg Arg Trp Phe
                245                 250                 255 gac cgc atg gtg cgt ccg tgg aac gag tgg ctg gtc gtg tgg ggc ttc           816
Asp Arg Met Val Arg Pro Trp Asn Glu Trp Leu Val Val Trp Gly Phe
            260                 265                 270 gac atc aac caa gag cca ccg aag ctg aac gac gac gag gcc atc cag           864
Asp Ile Asn Gln Glu Pro Pro Lys Leu Asn Asp Asp Glu Ala Ile Gln
            275                 280                 285 atc gtg cgc aac ctg gtg ggc atc gag gac ctg gac gtg gaa atc ctg           912
Ile Val Arg Asn Leu Val Gly Ile Glu Asp Leu Asp Val Glu Ile Leu
        290                 295                 300 ggc tac agc ctg tgg ggc aac aac gac cag tac gcc acc cat ctg cag           960
Gly Tyr Ser Leu Trp Gly Asn Asn Asp Gln Tyr Ala Thr His Leu Gln
305                 310                 315                 320 aaa ggc cgt gtg tgc tgc gcc ggt gac gcc atc cac aag cac cca ccg          1008
Lys Gly Arg Val Cys Cys Ala Gly Asp Ala Ile His Lys His Pro Pro
                325                 330                 335 agc cat ggc ctg ggc agc aac acc agc atc cag gac agc tac aac ctg          1056
Ser His Gly Leu Gly Ser Asn Thr Ser Ile Gln Asp Ser Tyr Asn Leu
            340                 345                 350 tgc tgg aag ctg gcc tgc gtg ctg aag ggc caa gcc ggt ccg gaa ctg          1104
Cys Trp Lys Leu Ala Cys Val Leu Lys Gly Gln Ala Gly Pro Glu Leu
            355                 360                 365 ctg gaa acc tac agc acc gag cgt gcc cca atc gcc aag cag atc gtg          1152
Leu Glu Thr Tyr Ser Thr Glu Arg Ala Pro Ile Ala Lys Gln Ile Val
        370                 375                 380 acc cgt gcc aac ggc agc agc agc gag tac aag ccg atc ttc gac gcc          1200
```

```
Thr Arg Ala Asn Gly Ser Ser Glu Tyr Lys Pro Ile Phe Asp Ala
385                 390                 395                 400 ctg ggc gtg acc gac gcc acc acc aac gac gag ttc gtg gaa aag ctg        1248
Leu Gly Val Thr Asp Ala Thr Thr Asn Asp Glu Phe Val Glu Lys Leu
                    405                 410                 415 gcc ctg cgc aaa gag aac agc cca gag ggg gca cgt cgt cgt gca gcc        1296
Ala Leu Arg Lys Glu Asn Ser Pro Glu Gly Ala Arg Arg Arg Ala Ala
            420                 425                 430 ctg cgt gcc gcg ctg gac aac aag gac tac gag ttc aac gcc cag ggc        1344
Leu Arg Ala Ala Leu Asp Asn Lys Asp Tyr Glu Phe Asn Ala Gln Gly
                435                 440                 445 acc gag atc ggt cag ttc tac gac agc agc gcc gtg atc acc gac ggc        1392
Thr Glu Ile Gly Gln Phe Tyr Asp Ser Ser Ala Val Ile Thr Asp Gly
450                 455                 460 cag aaa cgc cca gcc atg acc gag gac ccg atg ctg cac cac cag aag        1440
Gln Lys Arg Pro Ala Met Thr Glu Asp Pro Met Leu His His Gln Lys
465                 470                 475                 480 tcg acc ttc cca ggc ctg cgc ctg ccg cat gcc tgg ctg ggt gac gcc        1488
Ser Thr Phe Pro Gly Leu Arg Leu Pro His Ala Trp Leu Gly Asp Ala
                485                 490                 495 aaa gag aag tac agc acc cac gat atc gcc gag ggc acc cgc ttc acc        1536
Lys Glu Lys Tyr Ser Thr His Asp Ile Ala Glu Gly Thr Arg Phe Thr
                500                 505                 510 atc ttc acc ggc atc acc ggt cag gcc tgg gcc gat gcc gca gtg cgc        1584
Ile Phe Thr Gly Ile Thr Gly Gln Ala Trp Ala Asp Ala Ala Val Arg
            515                 520                 525 gtg gcc gaa cgt ctg ggc atc gat ctg aag gcc gtg gtg atc ggc gag        1632
Val Ala Glu Arg Leu Gly Ile Asp Leu Lys Ala Val Val Ile Gly Glu
530                 535                 540 ggc cag ccg gtg cag gac ctg tac ggt gat tgg ctg cgc cag cgc gag        1680
Gly Gln Pro Val Gln Asp Leu Tyr Gly Asp Trp Leu Arg Gln Arg Glu
545                 550                 555                 560 gtg gac gag gac ggt gtg atc ctg gtg cgt ccg gac aag cac atc ggc        1728
Val Asp Glu Asp Gly Val Ile Leu Val Arg Pro Asp Lys His Ile Gly
                565                 570                 575 tgg cgt gcc cag agc atg gtg gcc gat cca gaa acc gcc ctg ttc gac        1776
Trp Arg Ala Gln Ser Met Val Ala Asp Pro Glu Thr Ala Leu Phe Asp
                580                 585                 590 gtg ctg agc gcc ctg ctg cac acc aag cag acc ggc agc agc cat ctg        1824
Val Leu Ser Ala Leu Leu His Thr Lys Gln Thr Gly Ser Ser His Leu
            595                 600                 605 cgc gtg tga                                                            1833
Arg Val
    610

<210> SEQ ID NO 36
<211> LENGTH: 610
<212> TYPE: PRT
<213> ORGANISM: Pseudomonas sp. EST1001

<400> SEQUENCE: 36

Met Thr Thr Gln Arg Asn Asp Asn Leu Glu Gln Pro Gly Arg Ser Val
1               5                   10                  15

Ile Phe Asp Asp Gly Leu Ser Ala Thr Asp Thr Pro Asn Glu Thr Asn
            20                  25                  30

Val Val Glu Thr Glu Val Leu Ile Val Gly Ser Gly Pro Ala Gly Ser
        35                  40                  45

Ser Ala Ala Met Phe Leu Ser Thr Gln Gly Ile Ser Asn Ile Met Ile
    50                  55                  60
```

```
Thr Lys Tyr Arg Trp Thr Ala Asn Thr Pro Arg Ala His Ile Thr Asn
 65                  70                  75                  80

Gln Arg Thr Met Glu Ile Leu Arg Asp Ala Gly Ile Glu Asp Gln Val
                 85                  90                  95

Leu Ala Glu Ala Val Pro His Glu Leu Met Gly Asp Thr Val Tyr Cys
            100                 105                 110

Glu Ser Met Ala Gly Glu Ile Gly Arg Arg Pro Thr Trp Gly Thr
        115                 120                 125

Arg Pro Asp Arg Arg Ala Asp Tyr Glu Leu Ala Ser Pro Ala Met Pro
    130                 135                 140

Cys Asp Ile Pro Gln Thr Leu Leu Glu Pro Ile Met Leu Lys Asn Ala
145                 150                 155                 160

Thr Met Arg Gly Thr Gln Thr Gln Phe Ser Thr Glu Tyr Leu Ser His
                165                 170                 175

Thr Gln Asp Asp Lys Gly Val Ser Val Gln Val Leu Asn Arg Leu Thr
            180                 185                 190

Gly Gln Glu Tyr Thr Ile Arg Ala Lys Tyr Leu Ile Gly Ala Asp Gly
        195                 200                 205

Ala Arg Ser Lys Val Ala Ala Asp Ile Gly Gly Ser Met Asn Ile Thr
    210                 215                 220

Phe Lys Ala Asp Leu Ser His Trp Arg Pro Ser Ala Leu Asp Pro Val
225                 230                 235                 240

Leu Gly Leu Pro Pro Arg Ile Glu Tyr Arg Trp Pro Arg Arg Trp Phe
                245                 250                 255

Asp Arg Met Val Arg Pro Trp Asn Glu Trp Leu Val Val Trp Gly Phe
            260                 265                 270

Asp Ile Asn Gln Glu Pro Pro Lys Leu Asn Asp Asp Glu Ala Ile Gln
        275                 280                 285

Ile Val Arg Asn Leu Val Gly Ile Glu Asp Leu Asp Val Glu Ile Leu
    290                 295                 300

Gly Tyr Ser Leu Trp Gly Asn Asn Asp Gln Tyr Ala Thr His Leu Gln
305                 310                 315                 320

Lys Gly Arg Val Cys Cys Ala Gly Asp Ala Ile His Lys His Pro Pro
                325                 330                 335

Ser His Gly Leu Gly Ser Asn Thr Ser Ile Gln Asp Ser Tyr Asn Leu
            340                 345                 350

Cys Trp Lys Leu Ala Cys Val Leu Lys Gly Gln Ala Gly Pro Glu Leu
        355                 360                 365

Leu Glu Thr Tyr Ser Thr Glu Arg Ala Pro Ile Ala Lys Gln Ile Val
    370                 375                 380

Thr Arg Ala Asn Gly Ser Ser Ser Glu Tyr Lys Pro Ile Phe Asp Ala
385                 390                 395                 400

Leu Gly Val Thr Asp Ala Thr Thr Asn Asp Glu Phe Val Glu Lys Leu
                405                 410                 415

Ala Leu Arg Lys Glu Asn Ser Pro Glu Gly Ala Arg Arg Ala Ala
            420                 425                 430

Leu Arg Ala Ala Leu Asp Asn Lys Asp Tyr Glu Phe Asn Ala Gln Gly
        435                 440                 445

Thr Glu Ile Gly Gln Phe Tyr Asp Ser Ser Ala Val Ile Thr Asp Gly
    450                 455                 460

Gln Lys Arg Pro Ala Met Thr Glu Asp Pro Met Leu His Gln Lys
465                 470                 475                 480

Ser Thr Phe Pro Gly Leu Arg Leu Pro His Ala Trp Leu Gly Asp Ala
```

```
                485             490             495
Lys Glu Lys Tyr Ser Thr His Asp Ile Ala Glu Gly Thr Arg Phe Thr
            500                 505                 510

Ile Phe Thr Gly Ile Thr Gly Gln Ala Trp Ala Asp Ala Ala Val Arg
            515                 520                 525

Val Ala Glu Arg Leu Gly Ile Asp Leu Lys Ala Val Ile Gly Glu
            530                 535                 540

Gly Gln Pro Val Gln Asp Leu Tyr Gly Asp Trp Leu Arg Gln Arg Glu
545                 550                 555                 560

Val Asp Glu Asp Gly Val Ile Leu Val Arg Pro Asp Lys His Ile Gly
                565                 570                 575

Trp Arg Ala Gln Ser Met Val Ala Asp Pro Glu Thr Ala Leu Phe Asp
            580                 585                 590

Val Leu Ser Ala Leu Leu His Thr Lys Gln Thr Gly Ser Ser His Leu
            595                 600                 605

Arg Val
    610

<210> SEQ ID NO 37
<211> LENGTH: 1416
<212> TYPE: DNA
<213> ORGANISM: Sphinogbium sp. SYK-6
<220> FEATURE:
<221> NAME/KEY: CDS
<222> LOCATION: (1)..(1416)

<400> SEQUENCE: 37 atg agc acc ccg acc aac ctt gag cag gtg ttg gca gca ggc ggc aat      48
Met Ser Thr Pro Thr Asn Leu Glu Gln Val Leu Ala Ala Gly Gly Asn
1               5                   10                  15 acc gtg gag atg ctg cgt aac agc cag atc ggc gcc tac gtg tat ccg      96
Thr Val Glu Met Leu Arg Asn Ser Gln Ile Gly Ala Tyr Val Tyr Pro
            20                  25                  30 gtg gta gcc ccg gag ttc agc aac tgg cgt acc gaa caa tgg gcc tgg     144
Val Val Ala Pro Glu Phe Ser Asn Trp Arg Thr Glu Gln Trp Ala Trp
        35                  40                  45 cgc aat agc gca gtg ctg ttc gat cag acc cac cac atg gtg gac ctg     192
Arg Asn Ser Ala Val Leu Phe Asp Gln Thr His His Met Val Asp Leu
    50                  55                  60 tac atc cgc ggc aag gat gcc ctg aag ctg ctg agt gac acc atg atc     240
Tyr Ile Arg Gly Lys Asp Ala Leu Lys Leu Leu Ser Asp Thr Met Ile
65                  70                  75                  80 aac agc ccg aag ggc tgg gag ccg aac aaa gcc aag cag tat gtg ccg     288
Asn Ser Pro Lys Gly Trp Glu Pro Asn Lys Ala Lys Gln Tyr Val Pro
                85                  90                  95 gtg acc ccg tat ggc cac gtg att ggt gac ggc atc atc ttc tac ctg     336
Val Thr Pro Tyr Gly His Val Ile Gly Asp Gly Ile Ile Phe Tyr Leu
            100                 105                 110 gcc gag gag gag ttc gtg tac gtg ggt aga gca cca gcc gcc aat tgg     384
Ala Glu Glu Glu Phe Val Tyr Val Gly Arg Ala Pro Ala Ala Asn Trp
        115                 120                 125 ctg atg tac cat gcc cag acc ggc ggc tac aac gtg gat atc gtg cac     432
Leu Met Tyr His Ala Gln Thr Gly Gly Tyr Asn Val Asp Ile Val His
    130                 135                 140 gac gac cgc agc cca agt cgt cca atg ggt aaa ccg gtg cag cgc atc     480
Asp Asp Arg Ser Pro Ser Arg Pro Met Gly Lys Pro Val Gln Arg Ile
145                 150                 155                 160 agc tgg cgt ttc caa atc cag ggc ccg aaa gcc tgg gac gtg atc gaa     528
Ser Trp Arg Phe Gln Ile Gln Gly Pro Lys Ala Trp Asp Val Ile Glu
```

|  |  |
|---|---|
| aag ctg cac ggt ggc acc ctg gag aag ctg aag ttc ttc aac atg gcc<br>Lys Leu His Gly Gly Thr Leu Glu Lys Leu Lys Phe Phe Asn Met Ala<br>180 185 190 | 576 |
| gag atg aac atc gcc ggc atg aag atc cgc acc ctg cgt cat ggt atg<br>Glu Met Asn Ile Ala Gly Met Lys Ile Arg Thr Leu Arg His Gly Met<br>195 200 205 | 624 |
| gcc ggt gca cca ggt ctg gag att tgg ggt ccg tac gag acc cag gag<br>Ala Gly Ala Pro Gly Leu Glu Ile Trp Gly Pro Tyr Glu Thr Gln Glu<br>210 215 220 | 672 |
| aaa gcc cgt aac gcc atc ctg gaa gcc ggc aaa gag ttc ggc ctg atc<br>Lys Ala Arg Asn Ala Ile Leu Glu Ala Gly Lys Glu Phe Gly Leu Ile<br>225 230 235 240 | 720 |
| cca gtg ggt agc cgt gcc tat ccg agc aat acc ctg gaa agc ggc tgg<br>Pro Val Gly Ser Arg Ala Tyr Pro Ser Asn Thr Leu Glu Ser Gly Trp<br>245 250 255 | 768 |
| att ccg agc cca ttg cca gcc atc tac acc ggc gac aag ctg aag gcc<br>Ile Pro Ser Pro Leu Pro Ala Ile Tyr Thr Gly Asp Lys Leu Lys Ala<br>260 265 270 | 816 |
| tac cgc gaa tgg ttg ccg gcc aac agc tac gaa gcc agt ggt gcc atc<br>Tyr Arg Glu Trp Leu Pro Ala Asn Ser Tyr Glu Ala Ser Gly Ala Ile<br>275 280 285 | 864 |
| ggt ggc agc ttt gtg agc agc aac atc gag gac tac tac gtg aac ccg<br>Gly Gly Ser Phe Val Ser Ser Asn Ile Glu Asp Tyr Tyr Val Asn Pro<br>290 295 300 | 912 |
| tac gag atc ggc tac ggc cca ttc gtg aag ttc gac cac gac ttc atc<br>Tyr Glu Ile Gly Tyr Gly Pro Phe Val Lys Phe Asp His Asp Phe Ile<br>305 310 315 320 | 960 |
| ggc cgc gat gcc ttg gaa gcc atc gat cca gcc acc cag cgc aag aaa<br>Gly Arg Asp Ala Leu Glu Ala Ile Asp Pro Ala Thr Gln Arg Lys Lys<br>325 330 335 | 1008 |
| gtg acc ttg gcc tgg aac ggc gac gac atg gcc aag atc tac gcc agc<br>Val Thr Leu Ala Trp Asn Gly Asp Asp Met Ala Lys Ile Tyr Ala Ser<br>340 345 350 | 1056 |
| ctg ttc gac acc gag gca gat gcc cac tac aag ttc ttc gac ctg ccg<br>Leu Phe Asp Thr Glu Ala Asp Ala His Tyr Lys Phe Phe Asp Leu Pro<br>355 360 365 | 1104 |
| ctg gcc aac tac gcc aac acc aat gca gac gcc gtg ctg gat gcc gcc<br>Leu Ala Asn Tyr Ala Asn Thr Asn Ala Asp Ala Val Leu Asp Ala Ala<br>370 375 380 | 1152 |
| ggt aat gta gtg ggc atg agc atg ttc acc ggc tac agc tac aac gag<br>Gly Asn Val Val Gly Met Ser Met Phe Thr Gly Tyr Ser Tyr Asn Glu<br>385 390 395 400 | 1200 |
| aag cgc gca ctg agc ctg gcc acc atc gac cat gaa atc ccg gtg ggc<br>Lys Arg Ala Leu Ser Leu Ala Thr Ile Asp His Glu Ile Pro Val Gly<br>405 410 415 | 1248 |
| acc gag ttg acc gtg tta tgg ggc gag gag aac ggc ggt acc cgc aaa<br>Thr Glu Leu Thr Val Leu Trp Gly Glu Glu Asn Gly Gly Thr Arg Lys<br>420 425 430 | 1296 |
| acc acc gtg gaa ccg cac aag cag atg gca gtg cgt gca gtg gtg agc<br>Thr Thr Val Glu Pro His Lys Gln Met Ala Val Arg Ala Val Val Ser<br>435 440 445 | 1344 |
| cca gtg cca tat agc gtg acc gcc cgt gag acc tac gaa ggt ggt tgg<br>Pro Val Pro Tyr Ser Val Thr Ala Arg Glu Thr Tyr Glu Gly Gly Trp<br>450 455 460 | 1392 |
| cgt aaa gcc gcc gtg acc gca taa<br>Arg Lys Ala Ala Val Thr Ala<br>465 470 | 1416 |

<210> SEQ ID NO 38
<211> LENGTH: 471
<212> TYPE: PRT
<213> ORGANISM: Sphinogbium sp. SYK-6

<400> SEQUENCE: 38

| Met | Ser | Thr | Pro | Thr | Asn | Leu | Glu | Gln | Val | Leu | Ala | Ala | Gly | Gly | Asn |
|---|---|---|---|---|---|---|---|---|---|---|---|---|---|---|---|
| 1 | | | | 5 | | | | | 10 | | | | | 15 | |

| Thr | Val | Glu | Met | Leu | Arg | Asn | Ser | Gln | Ile | Gly | Ala | Tyr | Val | Tyr | Pro |
| | | | 20 | | | | | 25 | | | | | 30 | | |

| Val | Val | Ala | Pro | Glu | Phe | Ser | Asn | Trp | Arg | Thr | Glu | Gln | Trp | Ala | Trp |
| | | 35 | | | | | 40 | | | | | 45 | | | |

| Arg | Asn | Ser | Ala | Val | Leu | Phe | Asp | Gln | Thr | His | His | Met | Val | Asp | Leu |
| | 50 | | | | | 55 | | | | | 60 | | | | |

| Tyr | Ile | Arg | Gly | Lys | Asp | Ala | Leu | Lys | Leu | Leu | Ser | Asp | Thr | Met | Ile |
| 65 | | | | | 70 | | | | | 75 | | | | | 80 |

| Asn | Ser | Pro | Lys | Gly | Trp | Glu | Pro | Asn | Lys | Ala | Lys | Gln | Tyr | Val | Pro |
| | | | | 85 | | | | | 90 | | | | | 95 | |

| Val | Thr | Pro | Tyr | Gly | His | Val | Ile | Gly | Asp | Gly | Ile | Ile | Phe | Tyr | Leu |
| | | | | 100 | | | | | 105 | | | | | 110 | |

| Ala | Glu | Glu | Phe | Val | Tyr | Val | Gly | Arg | Ala | Pro | Ala | Ala | Asn | Trp |
| | | 115 | | | | | 120 | | | | | 125 | | |

| Leu | Met | Tyr | His | Ala | Gln | Thr | Gly | Gly | Tyr | Asn | Val | Asp | Ile | Val | His |
| | 130 | | | | | 135 | | | | | 140 | | | | |

| Asp | Asp | Arg | Ser | Pro | Ser | Arg | Pro | Met | Gly | Lys | Pro | Val | Gln | Arg | Ile |
| 145 | | | | | 150 | | | | | 155 | | | | | 160 |

| Ser | Trp | Arg | Phe | Gln | Ile | Gln | Gly | Pro | Lys | Ala | Trp | Asp | Val | Ile | Glu |
| | | | | 165 | | | | | 170 | | | | | 175 | |

| Lys | Leu | His | Gly | Gly | Thr | Leu | Glu | Lys | Leu | Lys | Phe | Phe | Asn | Met | Ala |
| | | | | 180 | | | | | 185 | | | | | 190 | |

| Glu | Met | Asn | Ile | Ala | Gly | Met | Lys | Ile | Arg | Thr | Leu | Arg | His | Gly | Met |
| | | 195 | | | | | 200 | | | | | 205 | | | |

| Ala | Gly | Ala | Pro | Gly | Leu | Glu | Ile | Trp | Gly | Pro | Tyr | Glu | Thr | Gln | Glu |
| | 210 | | | | | 215 | | | | | 220 | | | | |

| Lys | Ala | Arg | Asn | Ala | Ile | Leu | Glu | Ala | Gly | Lys | Glu | Phe | Gly | Leu | Ile |
| 225 | | | | | 230 | | | | | 235 | | | | | 240 |

| Pro | Val | Gly | Ser | Arg | Ala | Tyr | Pro | Ser | Asn | Thr | Leu | Glu | Ser | Gly | Trp |
| | | | | 245 | | | | | 250 | | | | | 255 | |

| Ile | Pro | Ser | Pro | Leu | Pro | Ala | Ile | Tyr | Thr | Gly | Asp | Lys | Leu | Lys | Ala |
| | | | 260 | | | | | 265 | | | | | 270 | | |

| Tyr | Arg | Glu | Trp | Leu | Pro | Ala | Asn | Ser | Tyr | Glu | Ala | Ser | Gly | Ala | Ile |
| | | 275 | | | | | 280 | | | | | 285 | | | |

| Gly | Gly | Ser | Phe | Val | Ser | Ser | Asn | Ile | Glu | Asp | Tyr | Tyr | Val | Asn | Pro |
| | 290 | | | | | 295 | | | | | 300 | | | | |

| Tyr | Glu | Ile | Gly | Tyr | Gly | Pro | Phe | Val | Lys | Phe | Asp | His | Asp | Phe | Ile |
| 305 | | | | | 310 | | | | | 315 | | | | | 320 |

| Gly | Arg | Asp | Ala | Leu | Glu | Ala | Ile | Asp | Pro | Ala | Thr | Gln | Arg | Lys | Lys |
| | | | | 325 | | | | | 330 | | | | | 335 | |

| Val | Thr | Leu | Ala | Trp | Asn | Gly | Asp | Asp | Met | Ala | Lys | Ile | Tyr | Ala | Ser |
| | | | | 340 | | | | | 345 | | | | | 350 | |

| Leu | Phe | Asp | Thr | Glu | Ala | Asp | Ala | His | Tyr | Lys | Phe | Phe | Asp | Leu | Pro |
| | | | 355 | | | | | 360 | | | | | 365 | | |

| Leu | Ala | Asn | Tyr | Ala | Asn | Thr | Asn | Ala | Asp | Ala | Val | Leu | Asp | Ala | Ala |
| | | 370 | | | | | 375 | | | | | 380 | | | |

```
Gly Asn Val Val Gly Met Ser Met Phe Thr Gly Tyr Ser Tyr Asn Glu
385                 390                 395                 400

Lys Arg Ala Leu Ser Leu Ala Thr Ile Asp His Glu Ile Pro Val Gly
            405                 410                 415

Thr Glu Leu Thr Val Leu Trp Gly Glu Glu Asn Gly Gly Thr Arg Lys
        420                 425                 430

Thr Thr Val Glu Pro His Lys Gln Met Ala Val Arg Ala Val Val Ser
    435                 440                 445

Pro Val Pro Tyr Ser Val Thr Ala Arg Glu Thr Tyr Glu Gly Gly Trp
    450                 455                 460

Arg Lys Ala Ala Val Thr Ala
465                 470
```

<210> SEQ ID NO 39
<211> LENGTH: 32
<212> TYPE: DNA
<213> ORGANISM: Artificial Sequence
<220> FEATURE:
<223> OTHER INFORMATION: PCR Primer

<400> SEQUENCE: 39
gcgacacgaa gctgtatagc cctgccctat tg                             32

<210> SEQ ID NO 40
<211> LENGTH: 28
<212> TYPE: DNA
<213> ORGANISM: Artificial Sequence
<220> FEATURE:
<223> OTHER INFORMATION: PCR Primer

<400> SEQUENCE: 40
gctatacagc ttcgtgtcgc tcaaggcg                                  28

<210> SEQ ID NO 41
<211> LENGTH: 33
<212> TYPE: DNA
<213> ORGANISM: Artificial Sequence
<220> FEATURE:
<223> OTHER INFORMATION: PCR Primer

<400> SEQUENCE: 41
acctcgtatt gtgtgaaatt gttatccgct cac                            33

<210> SEQ ID NO 42
<211> LENGTH: 30
<212> TYPE: DNA
<213> ORGANISM: Artificial Sequence
<220> FEATURE:
<223> OTHER INFORMATION: PCR Primer

<400> SEQUENCE: 42
aatttcacac aatacgaggt aagcacgatg                                30

<210> SEQ ID NO 43
<211> LENGTH: 28
<212> TYPE: DNA
<213> ORGANISM: Artificial Sequence
<220> FEATURE:
<223> OTHER INFORMATION: PCR Primer

<400> SEQUENCE: 43
ccgcggccgc catcattgag accgcgcg                                  28

<210> SEQ ID NO 44
<211> LENGTH: 31
<212> TYPE: DNA
<213> ORGANISM: Artificial Sequence
<220> FEATURE:
<223> OTHER INFORMATION: PCR Primer

<400> SEQUENCE: 44
ccgcggccgc gtgacataac ctcgaactca g                          31

<210> SEQ ID NO 45
<211> LENGTH: 28
<212> TYPE: DNA
<213> ORGANISM: Artificial Sequence
<220> FEATURE:
<223> OTHER INFORMATION: PCR Primer

<400> SEQUENCE: 45
caggacatca tcagccctcc tgcaacgc                              28

<210> SEQ ID NO 46
<211> LENGTH: 28
<212> TYPE: DNA
<213> ORGANISM: Artificial Sequence
<220> FEATURE:
<223> OTHER INFORMATION: PCR Primer

<400> SEQUENCE: 46
ggagggctga tgatgtcctg cgcaagcc                              28

<210> SEQ ID NO 47
<211> LENGTH: 29
<212> TYPE: DNA
<213> ORGANISM: Artificial Sequence
<220> FEATURE:
<223> OTHER INFORMATION: PCR Primer

<400> SEQUENCE: 47
aacctcgaac tcagatgcgc ttgaacagg                             29

<210> SEQ ID NO 48
<211> LENGTH: 37
<212> TYPE: DNA
<213> ORGANISM: Artificial Sequence
<220> FEATURE:
<223> OTHER INFORMATION: PCR Primer

<400> SEQUENCE: 48
gcgcatctga gttcgaggtt atgtcactgt gattttg                    37

<210> SEQ ID NO 49
<211> LENGTH: 50
<212> TYPE: DNA
<213> ORGANISM: Artificial Sequence
<220> FEATURE:
<223> OTHER INFORMATION: PCR Primer

<400> SEQUENCE: 49
atccccgggt accgagctcg aattcatgac cgtgaaaatt tcccacactg      50

<210> SEQ ID NO 50
<211> LENGTH: 43
<212> TYPE: DNA
<213> ORGANISM: Artificial Sequence
<220> FEATURE:
<223> OTHER INFORMATION: PCR Primer

```
<400> SEQUENCE: 50
cagctatgac catgattacg aattcttgaa tgccggcaac ccg          43

<210> SEQ ID NO 51
<211> LENGTH: 38
<212> TYPE: DNA
<213> ORGANISM: Artificial Sequence
<220> FEATURE:
<223> OTHER INFORMATION: PCR Primer

<400> SEQUENCE: 51
ccgaaaagtg ccacctgacg tcggccttgc tgctgcag               38

<210> SEQ ID NO 52
<211> LENGTH: 37
<212> TYPE: DNA
<213> ORGANISM: Artificial Sequence
<220> FEATURE:
<223> OTHER INFORMATION: PCR Primer

<400> SEQUENCE: 52
gccgcagctc gagatctgga attgtgagaa cgcctgg                37

<210> SEQ ID NO 53
<211> LENGTH: 36
<212> TYPE: DNA
<213> ORGANISM: Artificial Sequence
<220> FEATURE:
<223> OTHER INFORMATION: PCR Primer

<400> SEQUENCE: 53
agatctcgag ctgcggccgc ggtgaagctt ggggcc                 36

<210> SEQ ID NO 54
<211> LENGTH: 40
<212> TYPE: DNA
<213> ORGANISM: Artificial Sequence
<220> FEATURE:
<223> OTHER INFORMATION: PCR Primer

<400> SEQUENCE: 54
gctggatcct ctagtgagct cacgatttcc ccattgccag             40

<210> SEQ ID NO 55
<211> LENGTH: 27
<212> TYPE: DNA
<213> ORGANISM: Artificial Sequence
<220> FEATURE:
<223> OTHER INFORMATION: PCR Primer

<400> SEQUENCE: 55
ccaggcgttc tcacaattcc agatctg                           27

<210> SEQ ID NO 56
<211> LENGTH: 55
<212> TYPE: DNA
<213> ORGANISM: Artificial Sequence
<220> FEATURE:
<223> OTHER INFORMATION: PCR Primer

<400> SEQUENCE: 56
gagcggcccc aagcttcacc gcggccgctc acttcttgtc gctgaacagc tctgg    55
```